(12) United States Patent
Hsieh et al.

(10) Patent No.: US 12,378,201 B2
(45) Date of Patent: Aug. 5, 2025

(54) HISTONE DEMETHYLASE INHIBITORS FOR TREATING CANCERS

(71) Applicant: The Board of Regents of the University of Texas System, Austin, TX (US)

(72) Inventors: Jer-Tsong Hsieh, Plano, TX (US); Jung-Mo Ahn, Plano, TX (US); Zhi-Ping Liu, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 778 days.

(21) Appl. No.: 17/596,816

(22) PCT Filed: Jun. 20, 2020

(86) PCT No.: PCT/US2020/038843
§ 371 (c)(1),
(2) Date: Dec. 17, 2021

(87) PCT Pub. No.: WO2020/257733
PCT Pub. Date: Dec. 24, 2020

(65) Prior Publication Data
US 2022/0306584 A1  Sep. 29, 2022

Related U.S. Application Data

(60) Provisional application No. 62/864,210, filed on Jun. 20, 2019.

(51) Int. Cl.
*C07D 215/26* (2006.01)
*A61P 35/00* (2006.01)
*C07D 401/12* (2006.01)
*C07D 401/14* (2006.01)
*C07D 405/14* (2006.01)

(52) U.S. Cl.
CPC ............ *C07D 215/26* (2013.01); *A61P 35/00* (2018.01); *C07D 401/12* (2013.01); *C07D 401/14* (2013.01); *C07D 405/14* (2013.01)

(58) Field of Classification Search
CPC ...... A61P 35/00; C07D 401/12; C07D 215/26
See application file for complete search history.

(56) References Cited

U.S. PATENT DOCUMENTS

| 8,871,789 | B2 | 10/2014 | Kristie et al. | |
|---|---|---|---|---|
| 2013/0123344 | A1* | 5/2013 | Kristie | A61K 31/166 544/333 |
| 2016/0303095 | A1 | 10/2016 | Aguayo et al. | |
| 2019/0133980 | A1 | 5/2019 | Bindra et al. | |

OTHER PUBLICATIONS

He et al., Targeting Signaling Pathway Networks in Several Malignant Tumors: Progresses and Challenges, Front. Pharmacol., 2021, vol. 12(675675), pp. 1-17 (Year: 2021).*
Thinnes et al., Targeting histone lysine demethylases—Progress, challenges, and the future, Biochimica et Biophysica Acta, 2014, vol. 1839, pp. 1416-1432 (Year: 2014).*
Li et al., Exploring the potential of histone demethylase inhibition in multi-therapeutic approaches for cancer treatment, European Journal of Medicinal Chemistry, 2024, vol. 264, article 115999, pp. 1-28 (Year: 2024).*
Fukagawa, Tatsuo, "Critical histone post-translational modifications for centromere function and propagation," Cell Cycle, vol. 16, No. 13 (2017), pp. 1259-1265.
Nadal, Simon, et al., "Synthetic post-translational modification of histones," Current Opinion in Chemical Biology, vol. 45 (2018), pp. 35-47.
Lin, Hongzhi, et al., "Small molecule KDM4s inhibitors as anticancer agents," Journal of Enzyme Inhibition and Medicinal Chemistry, vol. 33, No. 1 (2018), pp. 777-793.
Kaniskan, H. Ümit, et al., "Inhibitors of Protein Methyltransferases and Demethylases," Chem. Rev. vol. 118 (2018), pp. 989-1068.
Binda, Claudia, et al., "Biochemical, Structural, and Biological Evaluation of Tranylcypromine Derivatives as Inhibitors of Histone Demethylases LSD1 and LSD2," J. Am. Chem. Soc., vol. 132 (2010), pp. 6827-6833.
Markolovic, Suzana, et al., "Structure-function relationships of human JmjC oxygenases—demethylases versus hydroxylases," Current Opinion in Structural Biology, vol. 41 (2016), pp. 62-72.
Guerra-Calderas, Lissania, et al., "The role of the histone demethylase KDM4A in cancer," Cancer Genetics, vol. 208 (2015), pp. 215-224.
Berry, William L., et al., "KDM4/JMJD2 Histone Demethylases: Epigenetic Regulators in Cancer Cells," Cancer Res. vol. 73, No. 10 (2013), pp. 2936-2942.
Chu, Chia-Han, et al., "KDM4B as a Target for Prostate Cancer: Structural Analysis and Selective Inhibition by a Novel Inhibitor," J. Med. Chem. No. 51 (2014), pp. 5975-5985.
Kawazu, Masahito, et al., "Histone Demethylase JMJD2B Functions as a Co-Factor of Estogen Receptor in Breast Cancer Proliferation and Mammary Gland Development," PLoS One, vol. 6, Issue 3 (2011) (13 pages).
Berry, William A., et al., "Oncogenic features of the JMJD2A histone demethylase in breast cancer," International Journal of Oncology, vol. 41 (2012), pp. 1701-1706.
King, Oliver N.F., et al., "Quantitative High-Throughput Screening Identifies 8-Hydroxyquinolines as Cell-Active Histone Demethylase Inhibitors," PLoS One, vol. 5, Issue 11 (2010) (12 pages).

(Continued)

*Primary Examiner* — Jeffrey H Murray
*Assistant Examiner* — Rilla Marie Samsell
(74) *Attorney, Agent, or Firm* — Thomas | Horstemeyer, LLP

(57) ABSTRACT

The present disclosure provides a new series of 8-hydroxyquinoline derivatives/analogs that are potent KDM4 inhibitors with high activity and selectivity against KDM4 enzymes. Also disclosed are the pharmaceutical compositions comprising such 8-hydroxyquinoline-based potent KDM4 inhibitors, or a pharmaceutically acceptable salt thereof, and method of use thereof, for treating cancer and neoplastic diseases and the like.

19 Claims, 17 Drawing Sheets

(56) References Cited

OTHER PUBLICATIONS

Hopkinson, Richard J., et al., "5-Carboxy-8-hydroxyquinoline is a Broad Spectrum 2-Oxoglutarate Oxygenase Inhibitor which Causes Iron Translocation," Chem. Sci. vol. 4 (2013) (15 pages).

Schiller, Rachel, et al., "A Cell-Permeable Ester Derivative of the JmjC Histone Demethylase Inhibitor IOX1," ChemMedChem vol. 9 (2014), pp. 566-571.

Carter, David M., et al., "Identification of a Novel Benzimidazole Pyrazolone Scaffold That Inhibits KDM4 Lysine Demethylases and Reduces Proliferation of Prostrate Cancer Cells," SLAS Discovery vol. 22, No. 7 (2017), pp. 801-812.

Wang, Lei, et al., "A small molecule modulates Jumonji histone demethylase activity and selectively inhibits cancer growth," Nature Communications, vol. 4 (2013) (13 pages).

Roatsch, Martin, et al., "Susbtituted 2-(aminopyrimidin-4-yl) pyridine-4-carboxylates as potent inhibitors of JumonjiC domain-containing histone demethylases," Future Med. Chem., vol. 8, No. 13 (2016), pp. 1553-1571.

England, Katherine S., et al., "Optimisation of a triazolopyridine based histone demethylase inhibitor yields a potent and selective KDM2A (FBXL11) inhibitor," Med. Chem. Commun., vol. 5 (2014) pp. 1879-1886.

Bavetsias, Vassilios, et al., "8-Substituted Pyrido[3,4-d]pyrimidin-4(3H)-one Derivatives As Potent, Cell Permeable, KDM4 (JMJD2) and KDM5 (JARID1) Histone Lysine Demethylase Inhibitors," J. Med. Chem., vol. 59 (2016), pp. 1388-1409.

Westaway, Susan M., et al., "Cell Penetrant Inhibitors of the KDM4 and KDM5 Families of Histone Lysine Demethylases. 1. 3-Amino-4-pyridine Carboxylate Derivatives," J. Med. Chem., vol. 59 (2016) pp. 1357-1369.

Westaway, Susan M., et al., "Cell Penetrant Inhibitors of the KDM4 and KDM5 Families of Histone Lysine Demethylases. 2. Pyrido[3,4-d]pyrimidin-4(3H)-one Derivatives," J. Med. Chem., vol. 59 (2016) pp. 1370-1387.

Fang, Zhen, et al., "Disovery of pyrazolo[1,5-a]pyrimidine-3-carbonitrile derivatives as a new class of histone lysine demethylase 4D (KDM4D) inhibitors," Bioorganic & Medical Chemistry Letters, vol. 17 (2017) pp. 3201-3204.

Chen, Young K., et al., "Design of KDM4 Inhibitors with Antiproliferative Effects in Cancer Models," ACS Med. Chem. Lett., vol. 8 (2017) pp. 869-874.

Metzger, Eric, et al., "KDM4 Inhibition Targets Breast Cancer Stem-like Cells," Cancer Res., vol. 77, No. 21 (2017) pp. 5900-5912.

Duan, Lingling, et al., "KDM4/JMJD2 Histone Demethylase Inhibitors Block Prostate Tumor Grown by Suppressing the Expression of AR and BMYB-Regulated Genes," Chemistry & Biology, vol. 22 (2015) pp. 1185-1196.

Duan, Lingling, et al., "Histone lysine demethylase KDM4B regulates the alternative splicing of the androgen receptor in response to androgen deprivation," Nucleic Acids Research, vol. 47, No. 22 (2019), pp. 11623-11636.

International Search Report and Written Opinion, PCT/US2020/038843, mailed Sep. 25, 2020 (14 pages).

\* cited by examiner

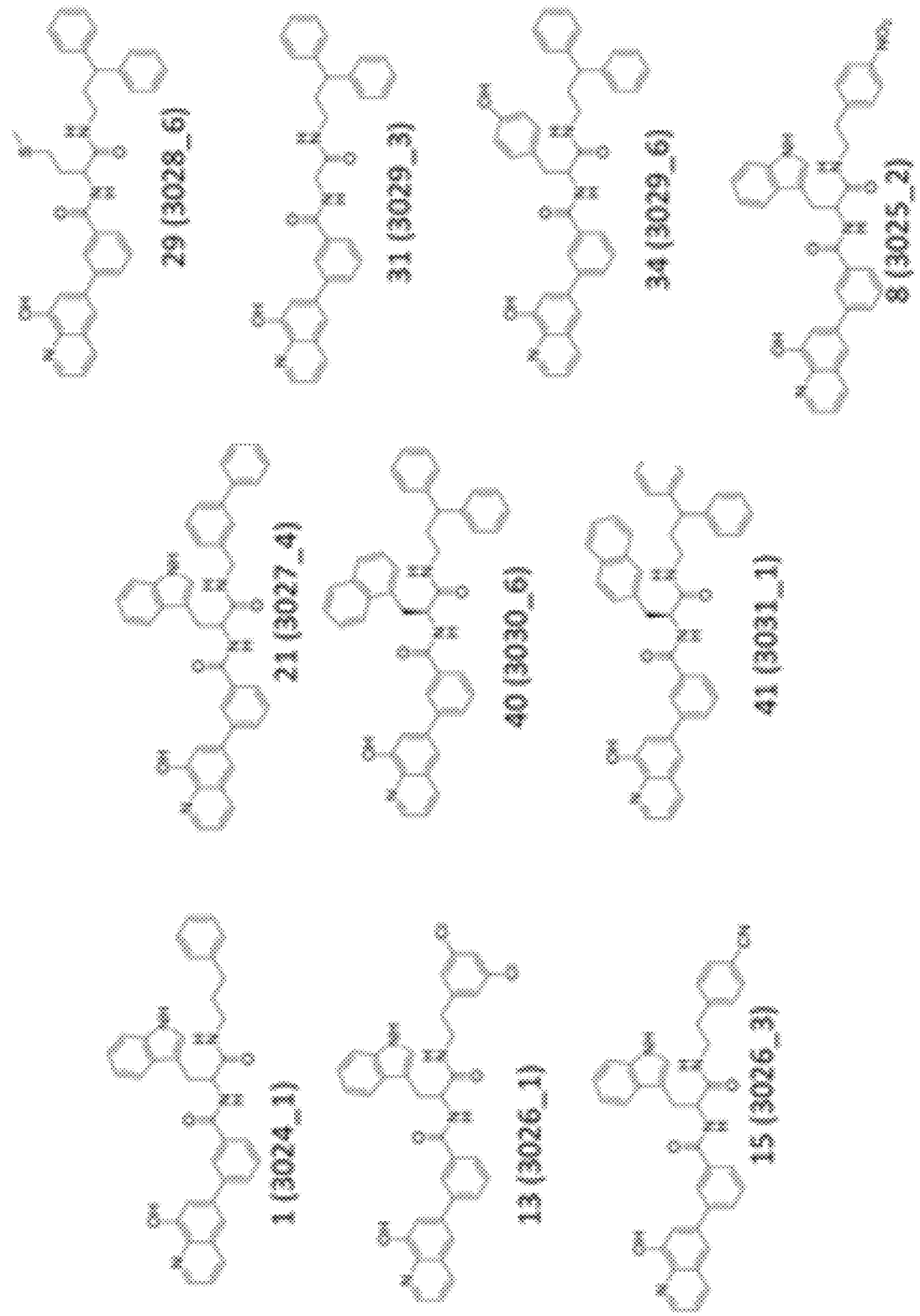
FIG. 10C, continued

HISTONE DEMETHYLASE INHIBITORS FOR TREATING CANCERS

CROSS-REFERENCE TO RELATED APPLICATIONS

This application is a U.S. national phase application under 35 U.S.C. 371 of International Patent Application No. PCT/US2020/038843, filed Jun. 20, 2020, which claims priority upon U.S. Provisional Application No. 62/864,210, filed on Jun. 20, 2019, both of which are incorporated herein by reference in their entirety.

STATEMENT OF GOVERNMENT INTEREST

This invention was made with government support under grant Nos. RP120717-P4, RP120717-P1, and RP120717-C1 awarded by Cancer Prevention and Research Institute of Texas (CPRIT) and R01CA215063 awarded by National Cancer Institute (NCI) of the National Institutes of Health (NIH). The government has certain rights in the invention.

FIELD OF INVENTION

The present disclosure relates generally to histone demethylase inhibitors, pharmaceutical compositions containing such inhibitors and to their use for cancer treatment.

BACKGROUND OF INVENTION

Histones are the basic scaffold proteins around which DNA is wound to form the highly-ordered structure of chromatin. Histones are subjected to many post-translational modifications that have been implicated in chromatin remodeling and are closely linked to transcriptional regulation, DNA duplication, and DNA repair. Histone post-translational modifications (covalent modifications of histones) such as phosphorylation on serine or threonine residues, methylation on lysine or arginine, acetylation and deacetylation of lysines, ubiquitylation of lysines, and sumoylation of lysines, are vital for cells to regulate the expression of genes in epigenetic level.[1] Among all post-translational modifications, methylation and demethylation of histones are most significant and have attracted much attention in the recent past.[2]

Histone methylation is an emerging epigenetic mechanism involved in tumorigenesis. Histone methylation may be associated with activation or repression of gene transcription, depending on which effector protein is recruited, and has been shown to be key in the regulation of gene expression and genetic stability. Dysregulation of histone methylation occurs in various cancers.

There are two classes of enzymes which are involved in reversible histone methylation (called histone methyltransferases) and demethylation (called histone demethylases).[3] Later enzymes (KDM family of enzymes) have been further classified into two main categories depending upon their mode of action, lysine specific demethylases (LSDs) and Jumonji domain-containing proteins (JMJDs). The LSD class of enzymes includes lysine specific demethylase LSD1 and LSD2, which are flavin-dependent amine oxidase domain-containing enzymes.[4] The other class comprises the recently discovered Jumonji domain-containing protein histone demethylases. JMJDs have been reported to remove the methyl groups from methylated lysines of histone H3 through Fe(II)/α-ketoglutarate-dependent enzymatic oxidation.[2]

Histone lysine demethylase (KDM) enzymes have been classified into six main subfamilies: KDM2, KDM3, KDM4, KDM5, KDM6, and KDM7.[5] Among them, KDM4 enzymes that act on di- and tri-methylated histone H3 lysine 9 (H3K9me2/me3) are regarded as promising targets for cancer therapy.[6] High expressions of KDM4s lead to oncogenesis in many kinds of cancers such as prostate cancer, breast cancer, colon cancer.[7] In the recent past, much attention has been given on the development of different KDM4s inhibitors as anti-cancer agents.[8] Although many of them have shown good activity[8] but promising clinical candidates with high activity and selectivity are still undiscovered. In a previous report, an 8-hydroxyquinoline based compound, B3, was discovered to be a highly selective and potent KDM4 inhibitor that repressed the transcription of both AR (an androgen receptor transcription factor) and B-MYB (a myeloblastosis family transcription factor) regulated genes and was highly effective against a variety of cancer cell lines including PC3 (a human prostate cancer cell line) cells that lack the androgen receptor (AR).[9] KDM4B has also shown to promote alternative splicing of AR and generate constitutively active AR-variant, AR-V7, that promotes castration-resistance. B3 has shown to be able to inhibit KDM4B-regulated AR-V7 expression.[10]

There still exists a need to develop more potent and selective therapeutics for safe, effective treatment of cancer and neoplastic disease.

SUMMARY OF THE INVENTION

The present disclosure provides a new series of 8-hydroxyquinoline derivatives/analogs that are potent KDM4 inhibitors with high activity and selectivity against KDM4 enzymes. The present disclosure further provides pharmaceutical compositions comprising such 8-hydroxyquinoline-based potent KDM4 inhibitors, or a pharmaceutically acceptable salt thereof, and method of use thereof, for treating cancer and neoplastic diseases, such as prostate cancer, kidney cancer, breast cancer, bladder cancer, lung cancer and/or melanoma and the like. The present disclosure further provides a method of treating KDM4-mediated disease in a patient comprising administering to the patient a therapeutically effective amount of the 8-hydroxyquinoline-based potent KDM4 inhibitors, or a pharmaceutically acceptable salt thereof, of the present disclosure.

In certain embodiments, the present disclosure provides a KDM4 inhibitor, or a pharmaceutically acceptable salt thereof, having a structure given by the formula:

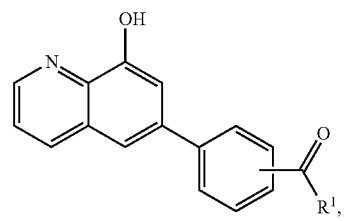

where $R^1$ is a group having a structure selected from the formulas:

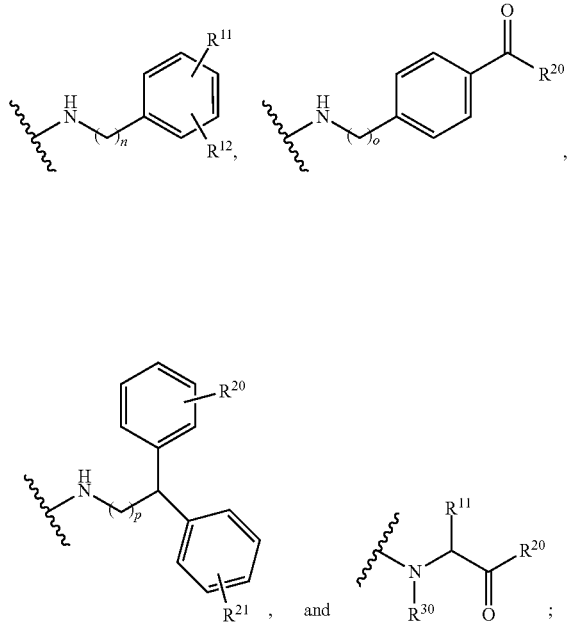

where n is from 0 to 10;
where o is from 0 to 10;
where p is from 0 to 10;
where each of $R^{11}$ and $R^{12}$, when present, is independently selected from hydrogen, halogen, hydroxy, thiol, cyano, amino, nitro, C1-C10 alkylamide, carbonyl, carboxylic acid, C1-C20 alkyl, C2-C20 alkenyl, C2-C20 alkynyl, C3-C20 cycloalkyl, C3-C20 heterocycloalkyl, aryl, heteroaryl, arylalkyl, and alkylaryl, and where each occurrence of C1-C10 alkylamide, C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl is optionally substituted with halogen, hydroxy, alkoxy, thiol, thioether, cyano, amino, carboxylic acid, ester, amide, carbamate, urea, guanidine, aryl substituted organic hydrazone, lactam substituted aryl group, nitro, —O—(C1-C6 alkyl), —$NR^{40}R^{41}$, C1-C6 alkylhydroxyl, C1-C6 haloalkyl, C1-C6 cycloalkyl, C1-C6 alkylamino, —$COR^{40}$, —$CO_2R^{40}$, aryl, and —$CONR^{40}R^{41}$;
where each of $R^{20}$ and $R^{21}$, when present, is selected from hydrogen, C1-C20 alkyl, C2-C20 alkenyl, C2-C20 alkynyl, C3-C20 cycloalkyl, C3-C20 heterocycloalkyl, aryl, heteroaryl, C1-C20 alkylheteroaryl, arylalkyl, alkylaryl, —P(=O)(OH)$R^{40}R^{41}$, —$SR^{40}$, —S(=O)$_2$$R^{40}R^{41}$, and —$NR^{40}R^{41}$ and where each occurrence of C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl is optionally substituted with halogen, hydroxy, thiol, cyano, amino, carboxylic acid, ester, amide, carbamate, urea, guanidine, nitro, —O—(C1-C6 alkyl), —$NR^{40}R^{41}$, C1-C6 alkylhydroxyl, C1-C6 haloalkyl, C1-C6 alkylamino, C1-C6 cycloalkyl, C3-C20 heterocycloalkyl, —$COR^{40}$, —$CO_2R^{40}$, aryl, or —$CONR^{40}R^{41}$;
where $R^{30}$, when present, is selected from hydrogen, C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl where each occurrence of C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl is optionally substituted with halogen, hydroxy, thiol, cyano, amino, nitro, —O—(C1-C6 alkyl), carboxylic acid, ester, amide, carbamate, urea, guanidine; and
where each occurrence of $R^{40}$ and $R^{41}$ is independently selected from hydrogen, C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl where each occurrence of C1-C20 alkyl, C2-C20 alkenyl, C2-C20 alkynyl, C3-C20 cycloalkyl, C3-C20 heterocycloalkyl, aryl, heteroaryl, arylalkyl, or alkylaryl is optionally substituted with halogen, hydroxy, thiol, cyano, amino, nitro, —O—(C1-C6 alkyl), halogen-substituted —O—(C1-C6 alkyl), —O—(C1-C6 aryl), halogen-substituted —O—(C1-C6 aryl), carboxylic acid, ester, amide, carbamate, urea, guanidine, C1-C4 linear or branched alkyl or haloalkyl, or C3-C6 cycloalkyl optionally substituted with a C1-C3 alkyl group or a C6 aryl group;
provided that the compound does not have a structure given by the formula:

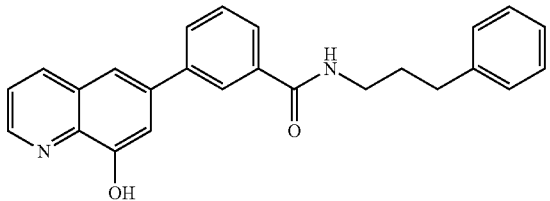

In other embodiments, the KDM4 inhibitor or pharmaceutically acceptable salt thereof includes the group of compounds wherein $R^1$ is

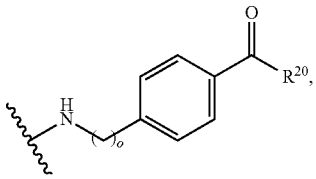

o is 1, $R^{20}$ is $NR^{40}R^{41}$, $R^{40}$ is hydrogen, and $R^{41}$ is C1-C20 alkyl substituted with C3-C6 cycloalkyl optionally substituted with a C1-C3 alkyl group, a C6 aryl group, or a C1-C4 linear or branched alkyl or haloalkyl group. Non-limiting examples of this group of compounds include the following:

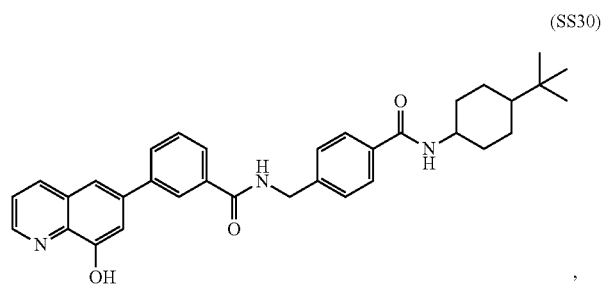
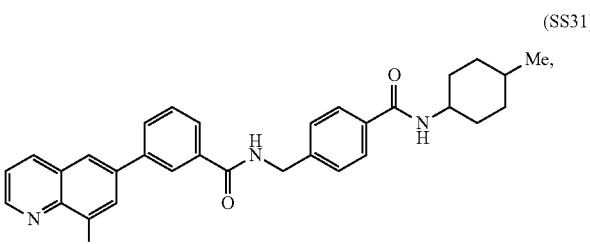
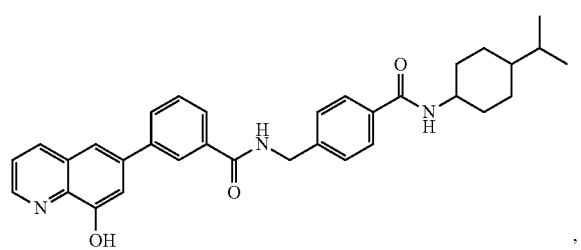
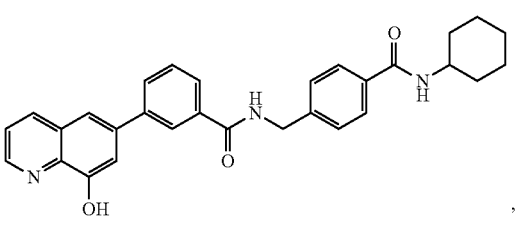
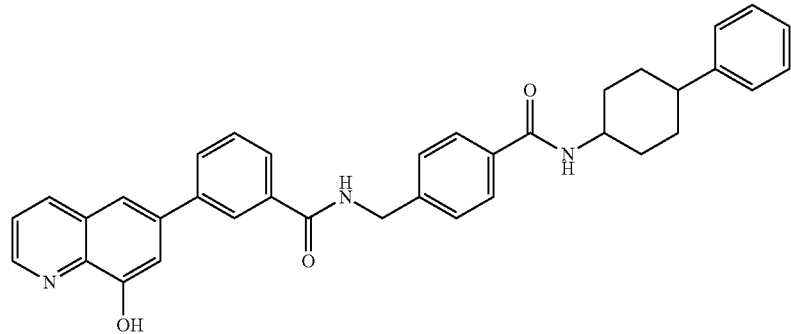
(SS27, oSS12, SS02208, SS79, SS79N, SS81, or 171)
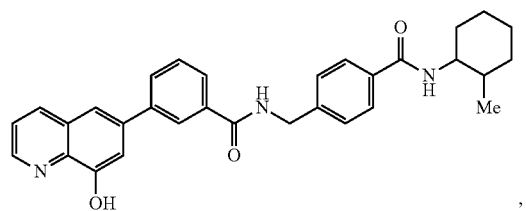
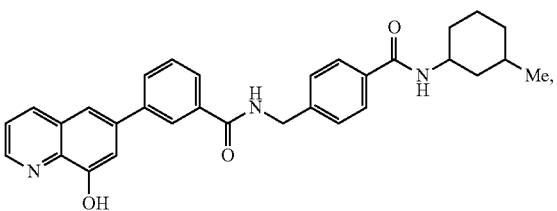
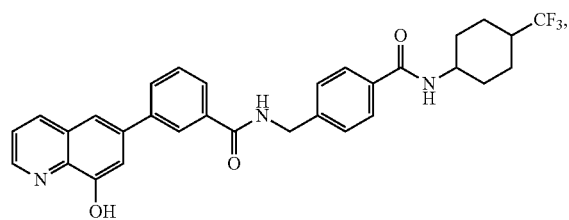
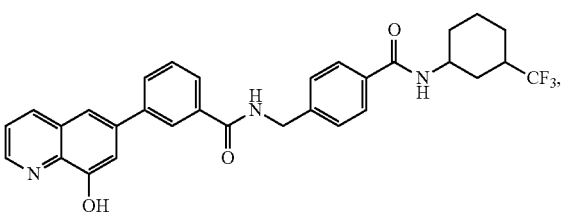

-continued

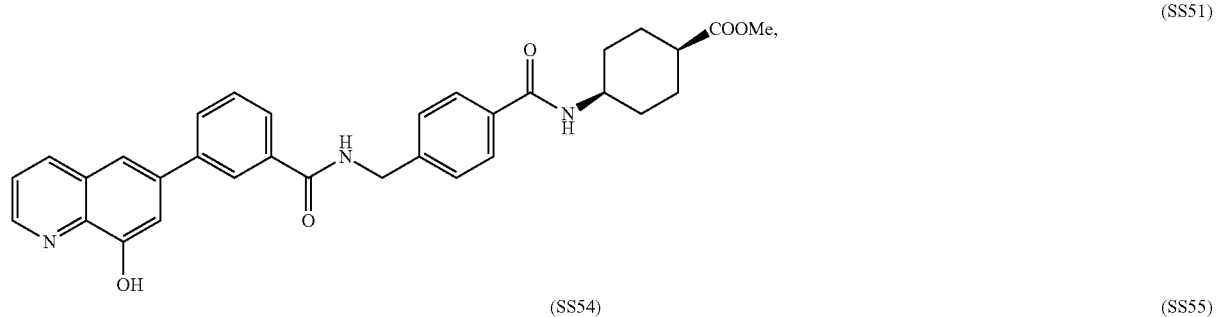
(SS51)

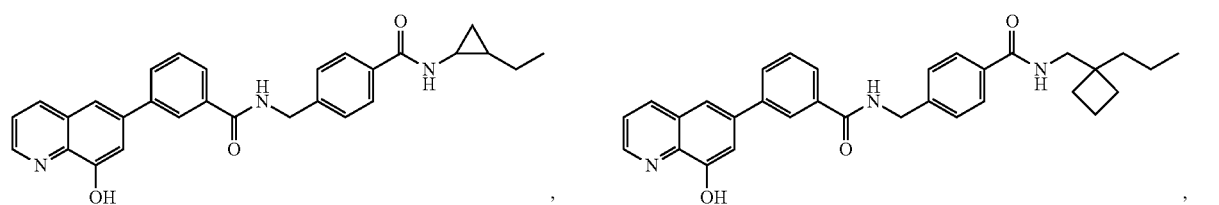
(SS54)            (SS55)

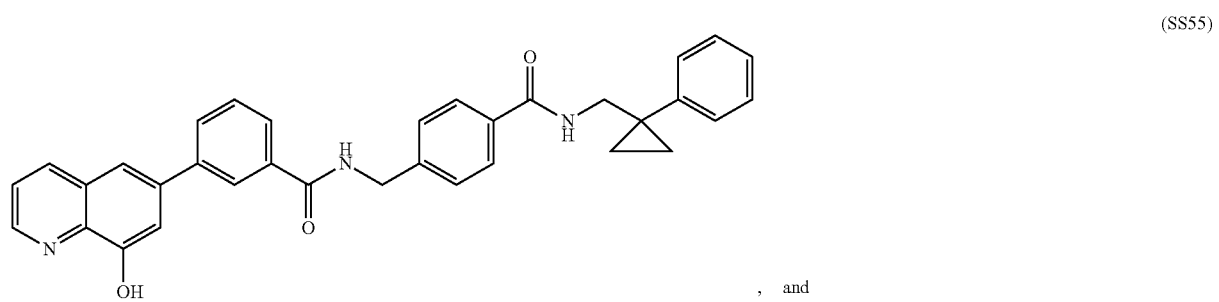
(SS55)
, and

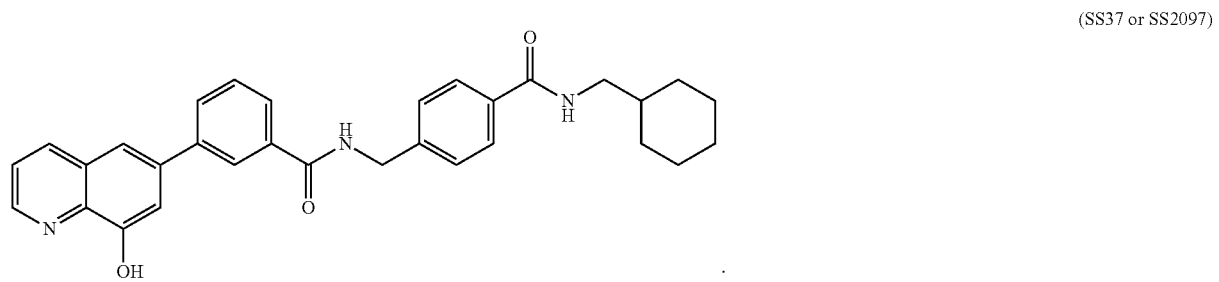
(SS37 or SS2097)

In other embodiments, the KDM4 inhibitor or pharmaceutically acceptable salt thereof includes the group of compounds wherein $R^1$ is

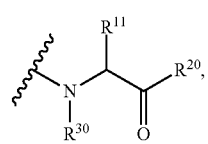

$R^{30}$ is hydrogen, $R^{11}$ is alkyl, hydrogen, alkylthioether, alkyl amide, hydroxy substituted alkyl aryl, or hydroxy substituted alkyl, $R^{20}$ is $NR^{40}R^{41}$, $R^{40}$ is hydrogen, and $R^{41}$ is alkylaryl. Non-limiting examples of this group of compounds include the following:

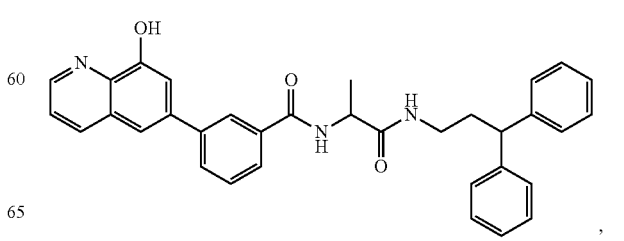
(3028-5)

-continued
(3028-6)
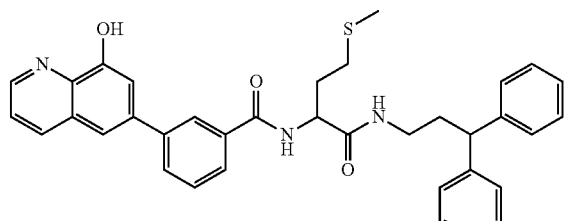,
(3028-3)
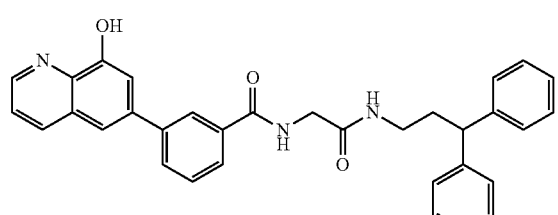,
(3029-5)
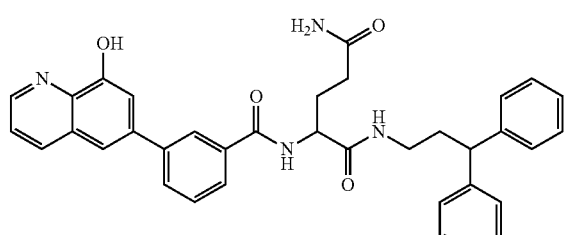,
(3029-6)
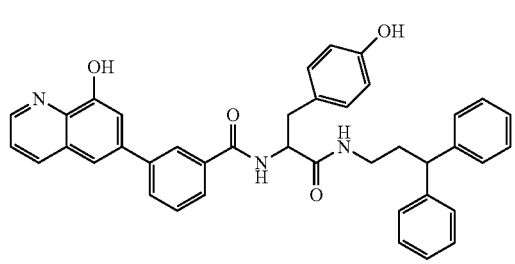, and
(3030-3)
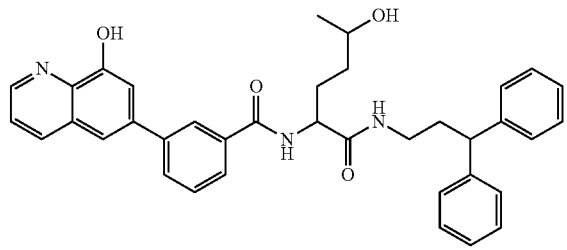.
In other embodiments, the KDM4 inhibitor or pharmaceutically acceptable salt thereof includes the group of compounds wherein $R^1$ is
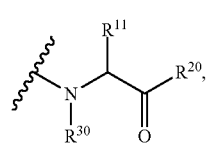
$R^{30}$ is H, $R^{11}$ is alkyl heteroaryl, $R^{20}$ is $NR^{40}R^{41}$, $R^{40}$ is hydrogen, and $R^{41}$ is substituted or unsubstituted alkylaryl. Non-limiting examples of compounds in this group include the following:
(3025-1)
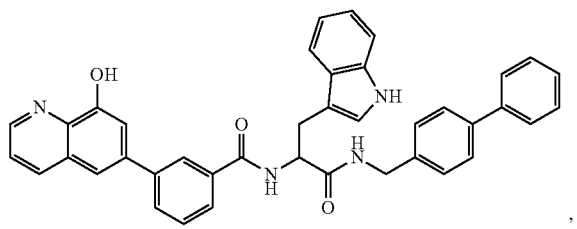,
(3025-2)
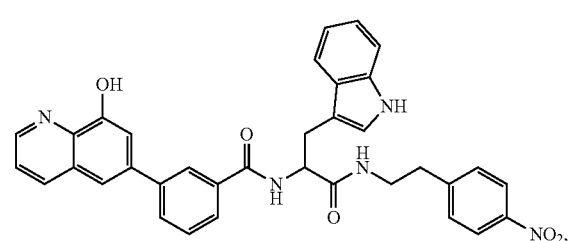,
(3025-3)
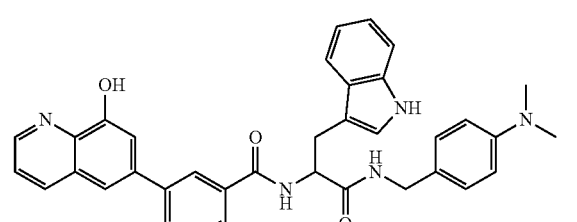,
(3025-6)
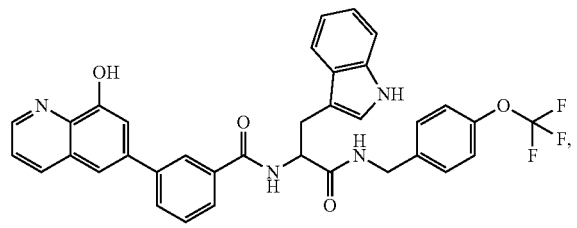,
(3026-3)
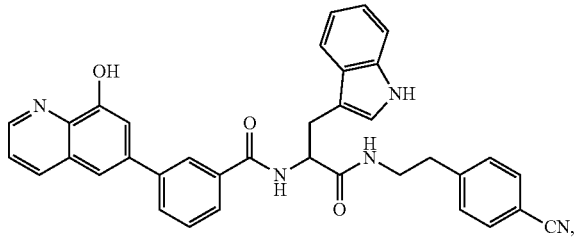, (3026-6)
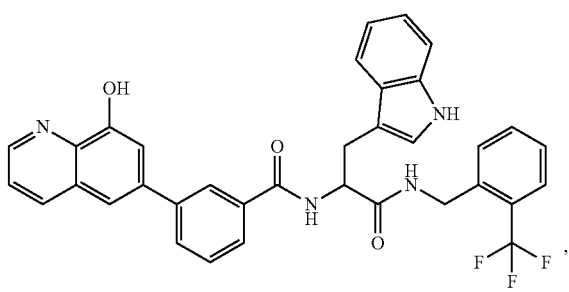

(3027-1)
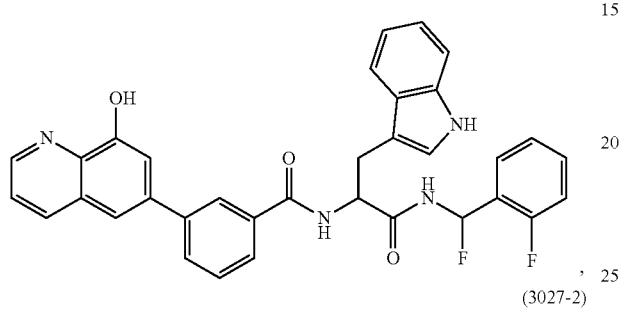

(3027-2)
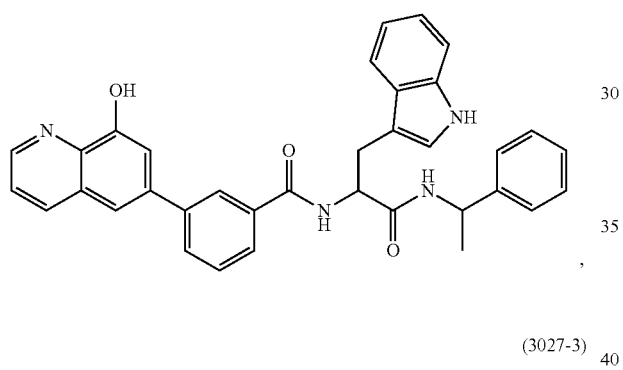

(3027-3)
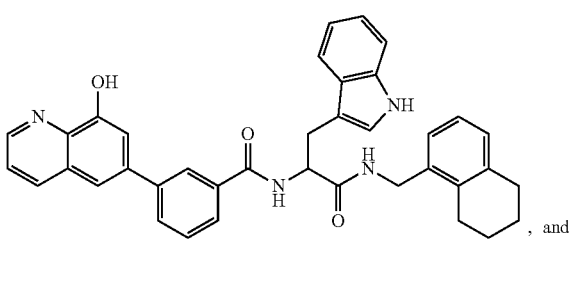

(3027-4)
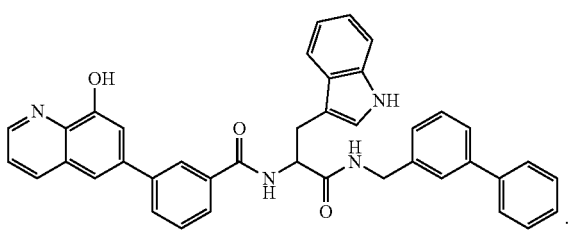

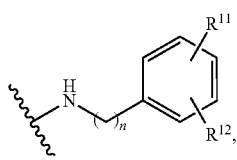

n is from 0 to 4, and $R^{11}$ and $R^{12}$ are hydrogen. Non-limiting examples of compounds in this group include the following:

(SS04190 or SS-61)
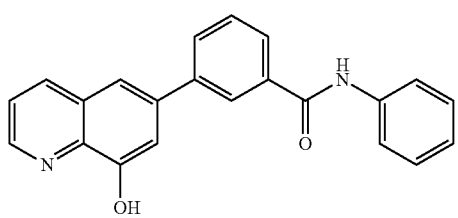

(SS04191 or SS-62)
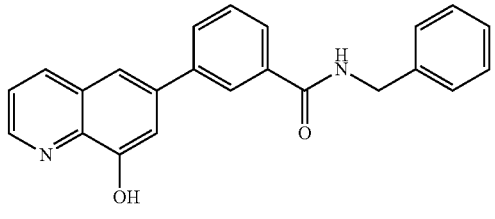

(SS04194 or SS-64)
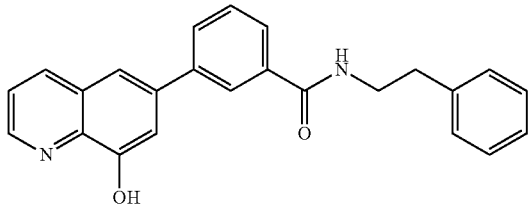

(B-3)
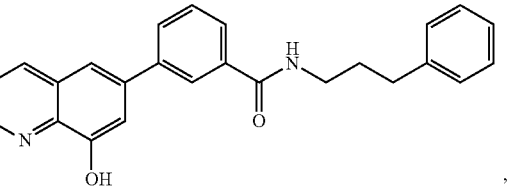
, and (SS04193 or SS-63)
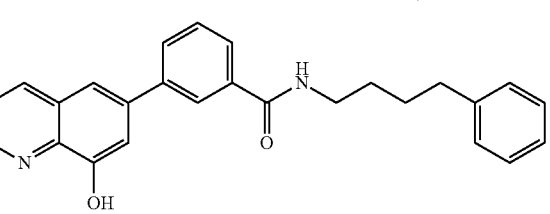
.

In other embodiments, the KDM4 inhibitor or pharmaceutically acceptable salt thereof includes the group of compounds wherein R1 is In other embodiments, the KDM4 inhibitor or pharmaceutically acceptable salt thereof includes the group of compounds wherein $R^1$ is

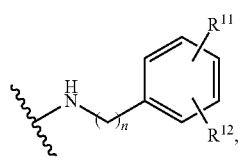
n is 1, $R^{11}$ is hydrogen or alkoxy, $R^{12}$ is cyano, alkoxy, substituted amine, $COR^{40}$, or $OR^{40}$, and $R^{40}$ is aryl, heteroaryl, or aryl substituted with a halogen. Non-limiting examples of compounds in this group include the following:
(SS02106)
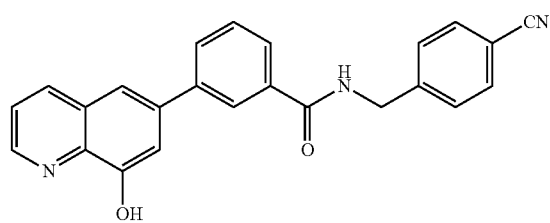
(SS74 or SS02132)
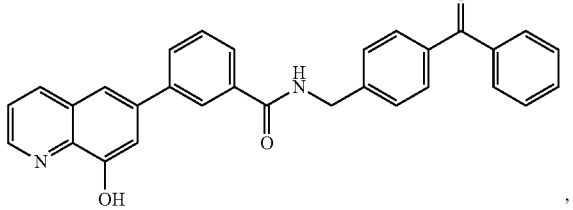
(SS02075)
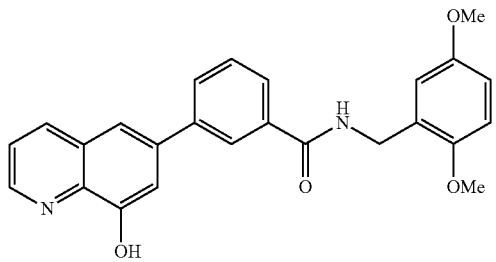
(SS02083)
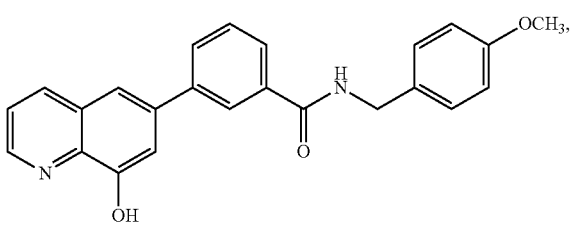
(SS02095)
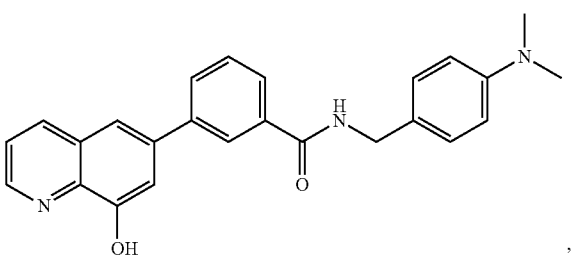
-continued
(SS1)
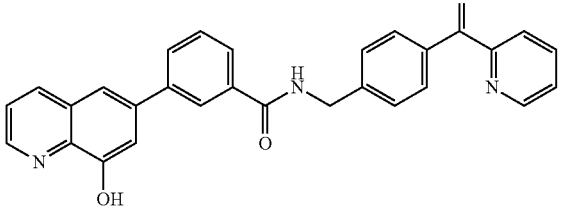
(SS2)
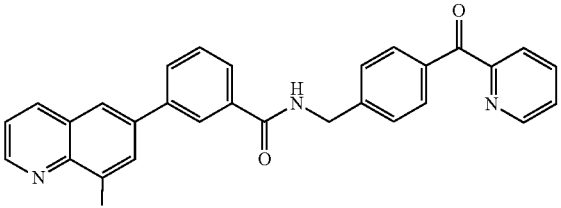
(SS12 or SS03154)
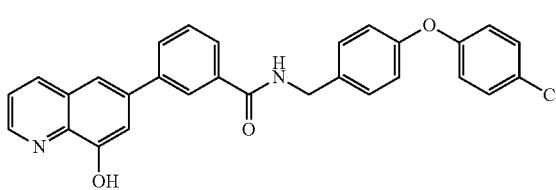
(SS13 or SS03152)
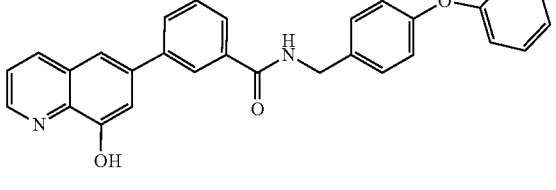
(SS14 or SS03156)
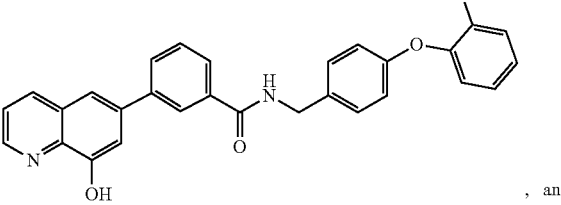
, and
(SS15 or SS03158)
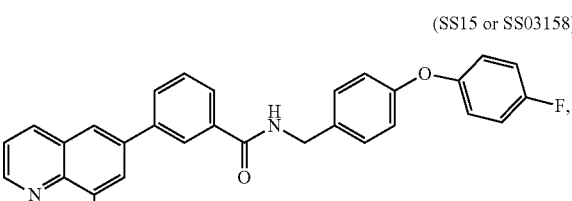

In other embodiments, the KDM4 inhibitor or pharmaceutically acceptable salt thereof includes the group of compounds wherein $R^1$ is

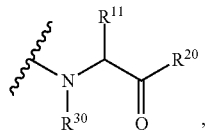, $R^{30}$ is hydrogen, $R^{11}$ is methyl, $R^{20}$ is $NR^{40}R^{41}$, $R^{40}$ is hydrogen, and $R^{41}$ is unsubstituted or substituted alkylaryl. Non-limiting examples of compounds in this group include the following:

In other embodiments, the KDM4 inhibitor or pharmaceutically acceptable salt thereof includes the group of compounds wherein $R^1$ is

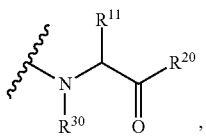, $R^{30}$ is hydrogen, $R^{20}$ is $NR^{40}R^{41}$, $R^{40}$ is hydrogen, $R^{41}$ is alkylaryl, and $R^{11}$ is alkylamide substituted with a cycloalkyl or aryl group. Non-limiting compounds in this group include the following:

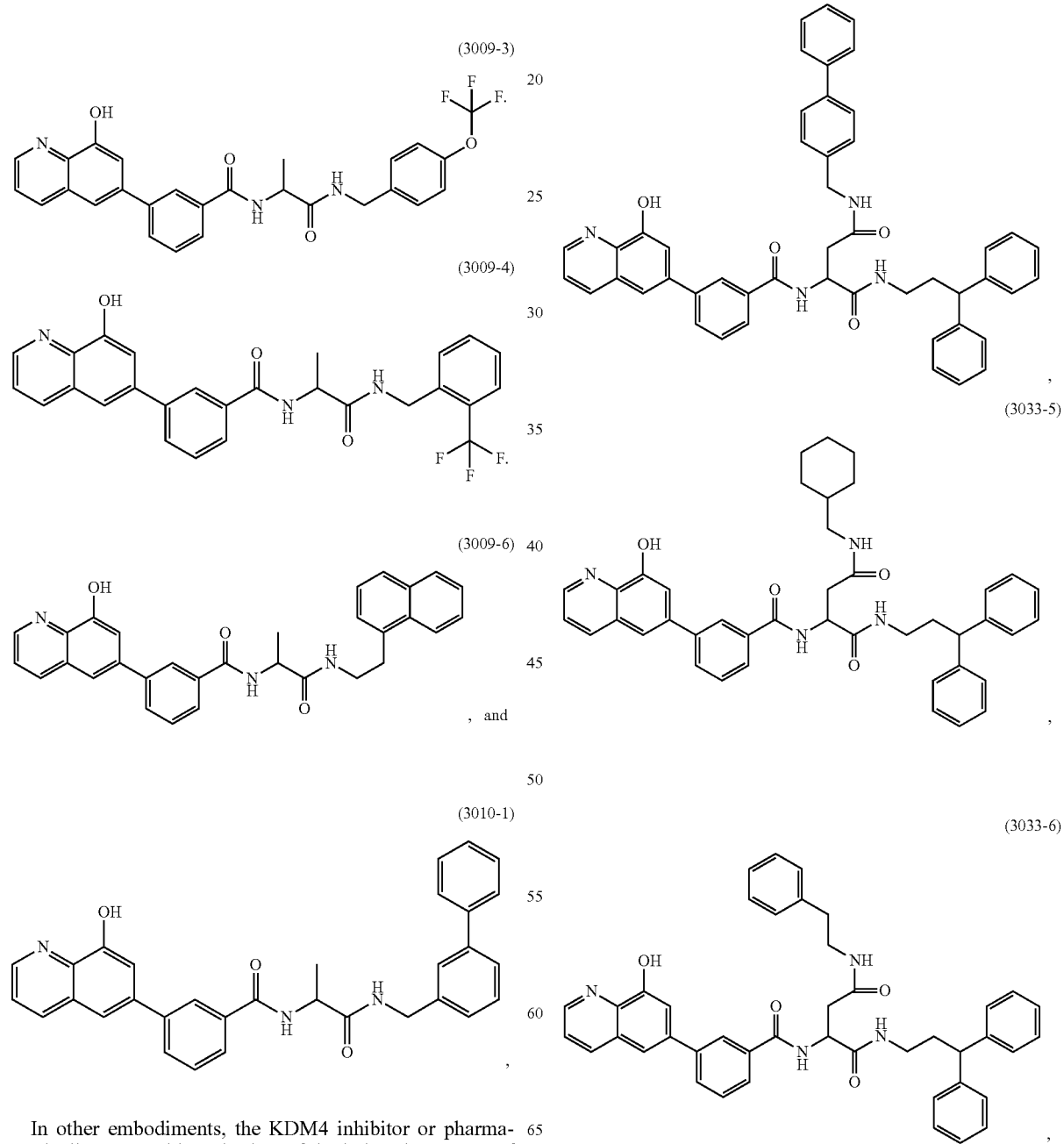

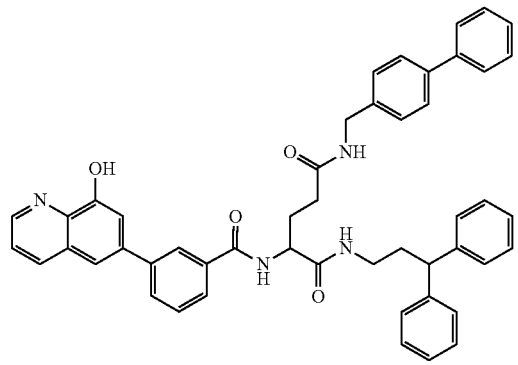

(3034-3)

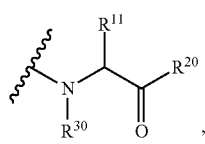

(3013-6)

In other embodiments, the KDM4 inhibitor or pharmaceutically acceptable salt thereof includes the group of compounds wherein $R^1$ is

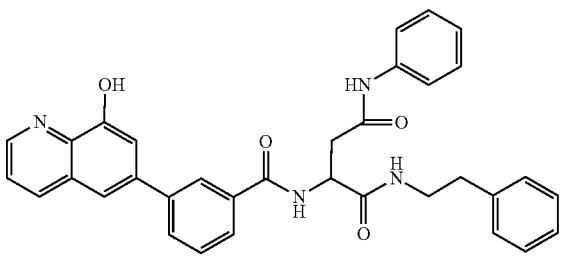

$R^{30}$ is hydrogen, $R^{11}$ is alkylheteroaryl, $R^{20}$ is $NR^{40}R^{41}$, $R^{40}$ is hydrogen, and $R^{41}$ is aryl or heteroaryl. Non-limiting examples of compounds in this group include the following:

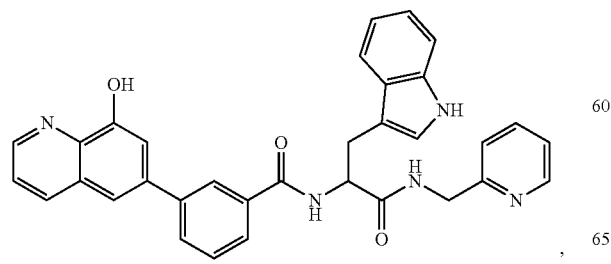

(3031-3)

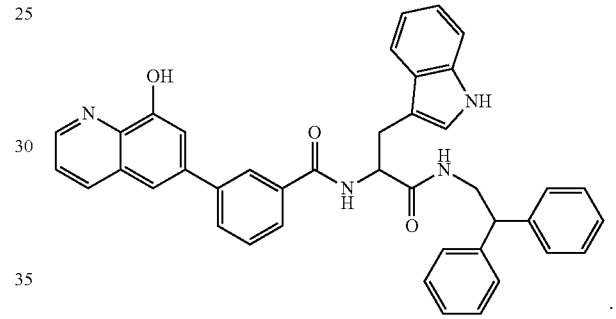

(3031-4)

(3031-5)

(3031-6)

In other embodiments, the KDM4 inhibitor or pharmaceutically acceptable salt thereof includes the group of compounds wherein $R^1$ is

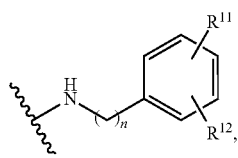

n is 0 or 1, $R^{11}$ is halogen, substituted or unsubstituted arylalkyl, ester, or $COR^{40}$, $R^{12}$ is hydrogen or halogen, and $R^{40}$ is aryl. Non-limiting examples of compounds in this group include the following:

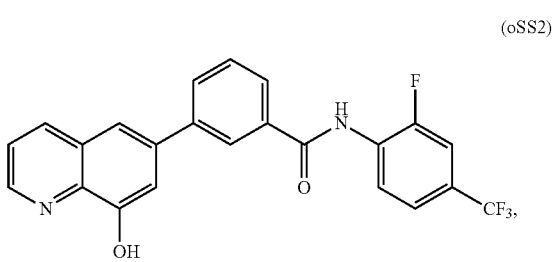

(oSS2)

-continued

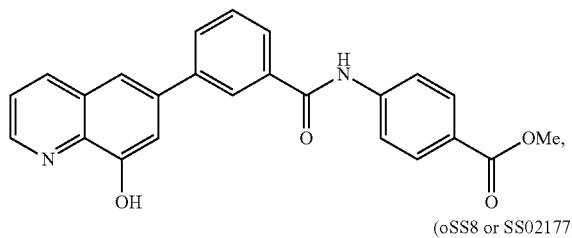
(oSS5 or SS02183)

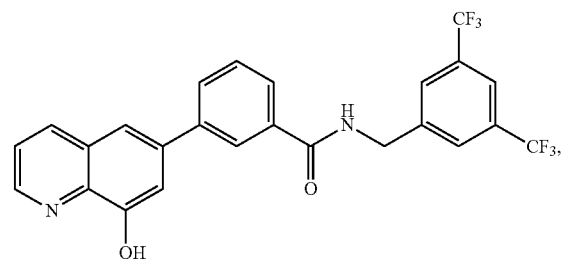
(oSS8 or SS02177)

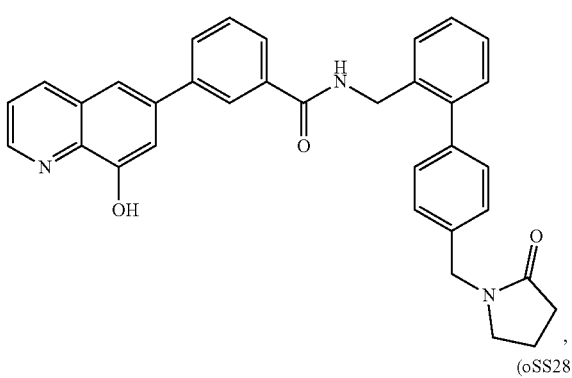
(oSS18 or SS03020)

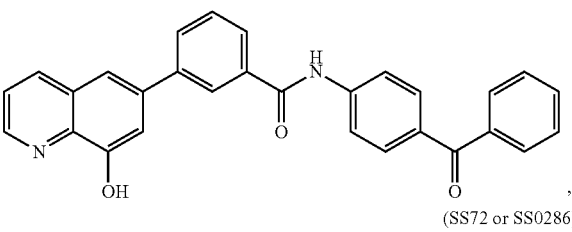
(oSS28)

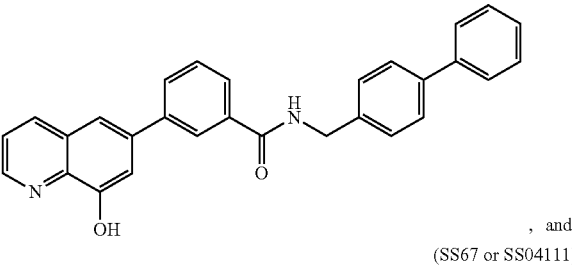
(SS72 or SS0286)

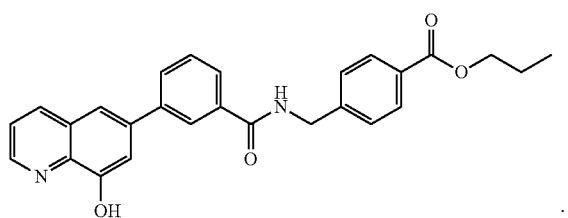
(SS67 or SS04111)

In other embodiments, the KDM4 inhibitor or pharmaceutically acceptable salt thereof includes the group of compounds wherein $R^1$ is

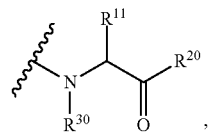

$R^{11}$ is alkyl, alkyl thioether, hydroxyl substituted alkyl aryl, hydroxyl substituted alkyl, or alkylheteroaryl, $R^{30}$ is hydrogen, $R^{20}$ is $NR^{40}R^{41}$, $R^{40}$ is hydrogen, and $R^{41}$ is alkylaryl optionally substituted with halogen or aryl. Non-limiting examples of compounds in this group include the following:

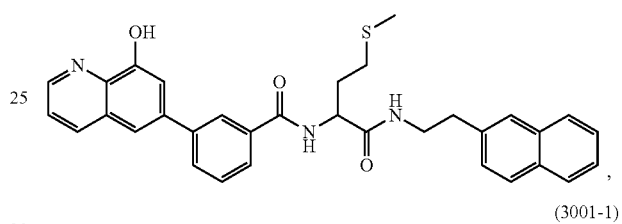
(3023-3)

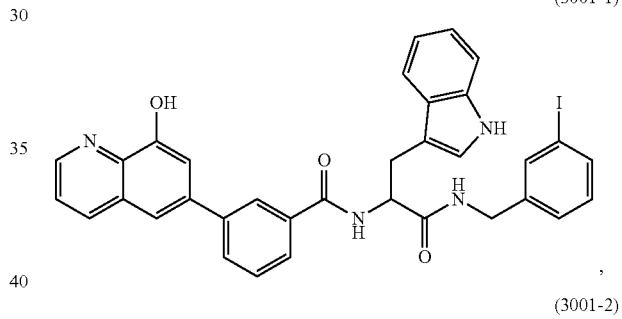
(3001-1)

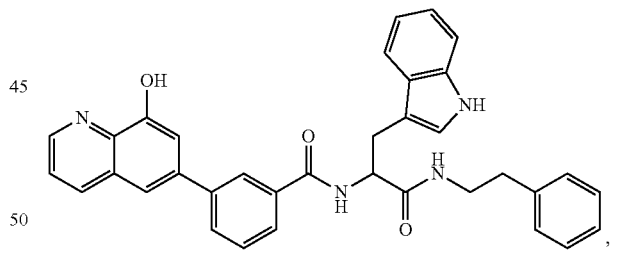
(3001-2)

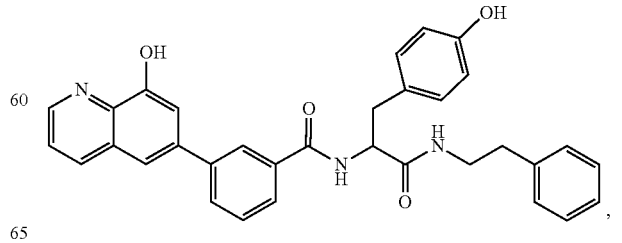
(3001-3)

(3001-4)
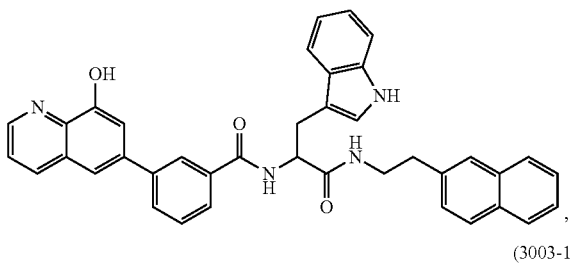
,
(3003-1)
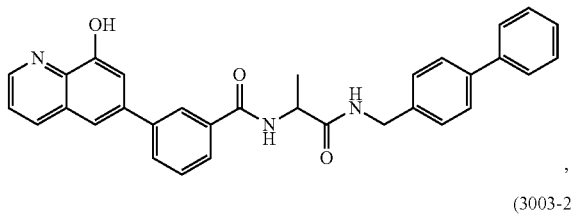
,
(3003-2)
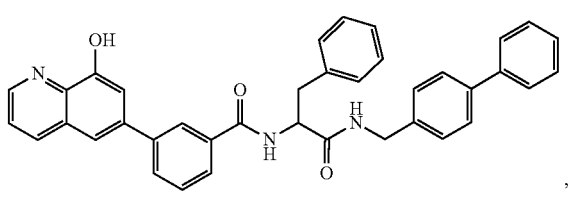
,
(3003-4)
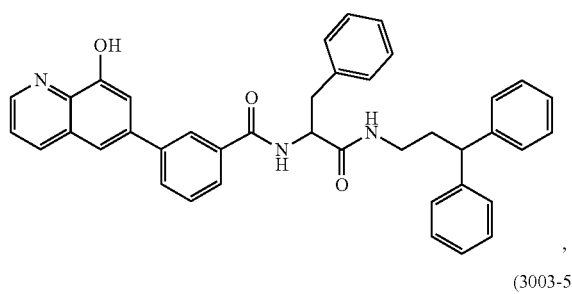
,
(3003-5)
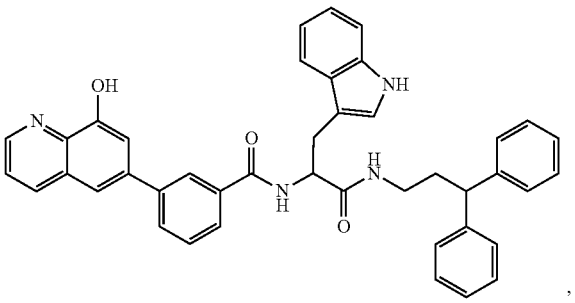
,
(3029-4)
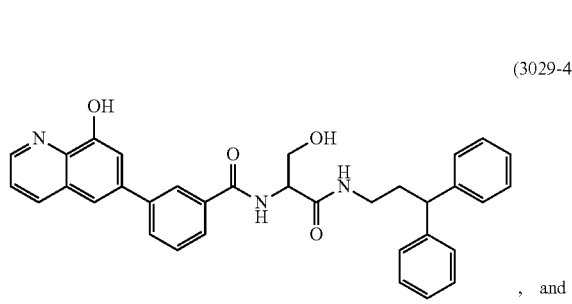
, and
(3024-1)
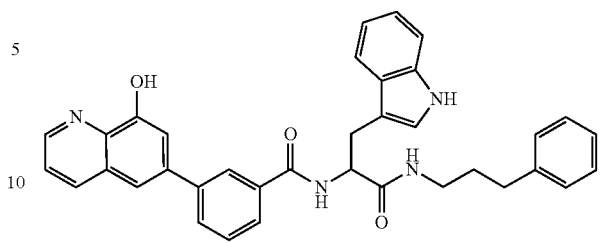
.
In other embodiments, the KDM4 inhibitor or pharmaceutically acceptable salt thereof includes the group of compounds wherein $R^1$ is
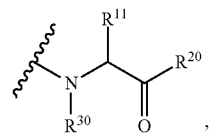,
$R^{30}$ is hydrogen, $R^{11}$ is alkylaryl or alkylheteroaryl, $R^{20}$ is $NR^{40}R^{41}$, $R^{40}$ is hydrogen, and $R^{41}$ is alkyl aryl or aryl heterocycloalkyl. Non-limiting examples of compounds in this group include the following:
(3008-1 or D37)
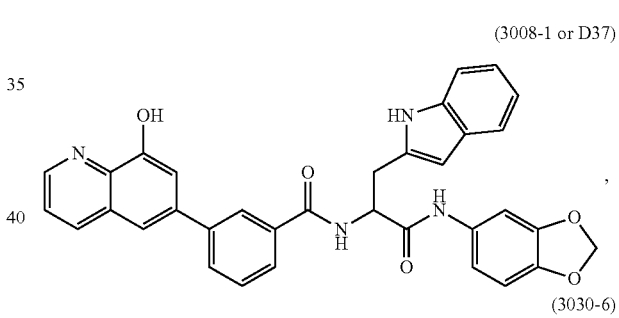
,
(3030-6)
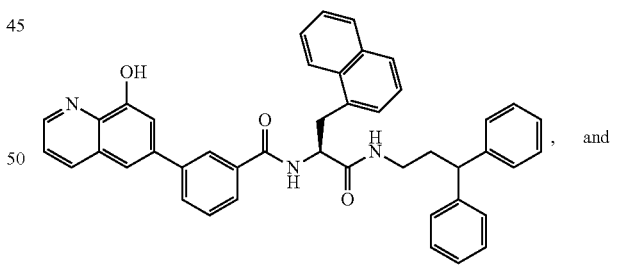
, and
(3031-1)
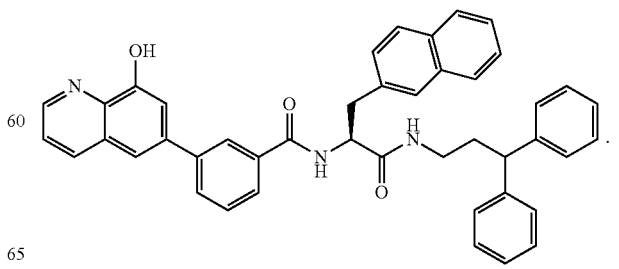
.

In other embodiments, the KDM4 inhibitor or pharmaceutically acceptable salt thereof includes the group of compounds wherein $R^1$ is

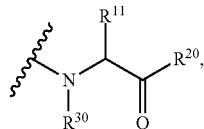

$R^{30}$ is hydrogen, $R^{11}$ is alkylaryl, $R^{20}$ is $NR^{40}R^{41}$, $R^{40}$ is hydrogen, and $R^{41}$ is alkyl substituted with a cycloalkyl group. Non-limiting examples of compounds in this group include the following:

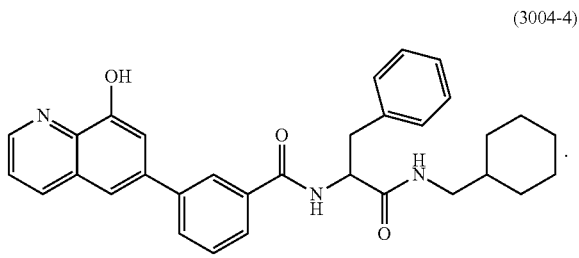 [SMILES: O=C(NC(Cc1ccccc1)C(=O)NCC1CCCCC1)c1cccc(-c2cc(O)c3ncccc3c2)c1]

(3004-4)

In other embodiments, the KDM4 inhibitor or pharmaceutically acceptable salt thereof includes the group of compounds wherein $R^1$ is

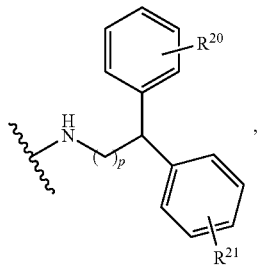

p is 2, $R^{20}$ is halogen, and $R^{21}$ is alkyl substituted with halogen. Non-limiting examples of compounds in this group include the following:

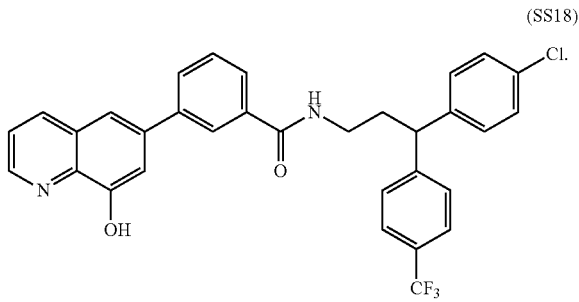 [SMILES: O=C(NCCC(c1ccc(Cl)cc1)c1ccc(C(F)(F)F)cc1)c1cccc(-c2cc(O)c3ncccc3c2)c1]

(SS18)

In some embodiments, disclosed herein are pharmaceutical compositions including at least one of the disclosed compounds or its pharmaceutically acceptable salt as well as at least one excipient. In other embodiments, disclosed herein are methods for treating cancer including methods for reducing tumor volume and/or reducing the growth of tumors.

DETAILED DESCRIPTION OF THE INVENTION

Figure 1:
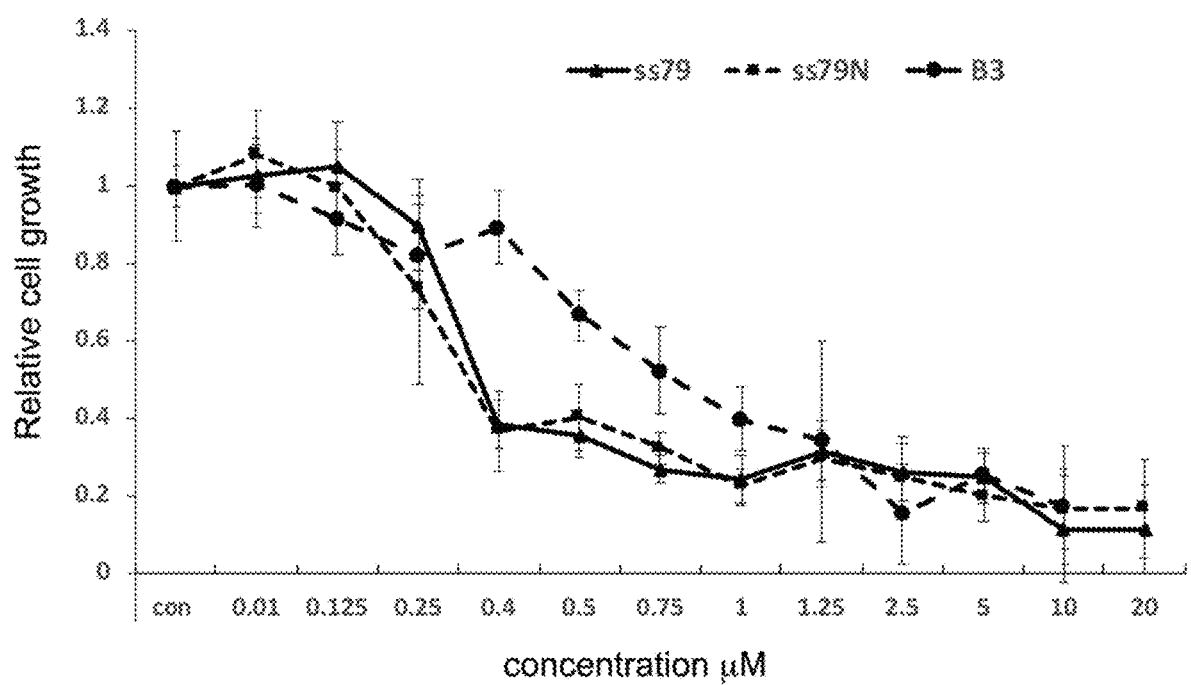
FIG. 1 shows MTT assays of SS79 (=SS27), SS79N (=SS27), and B3 on 22RV1 prostate cancer cells (B3=8-hydroxyquinoline analog previously reported).
Figure 2A:
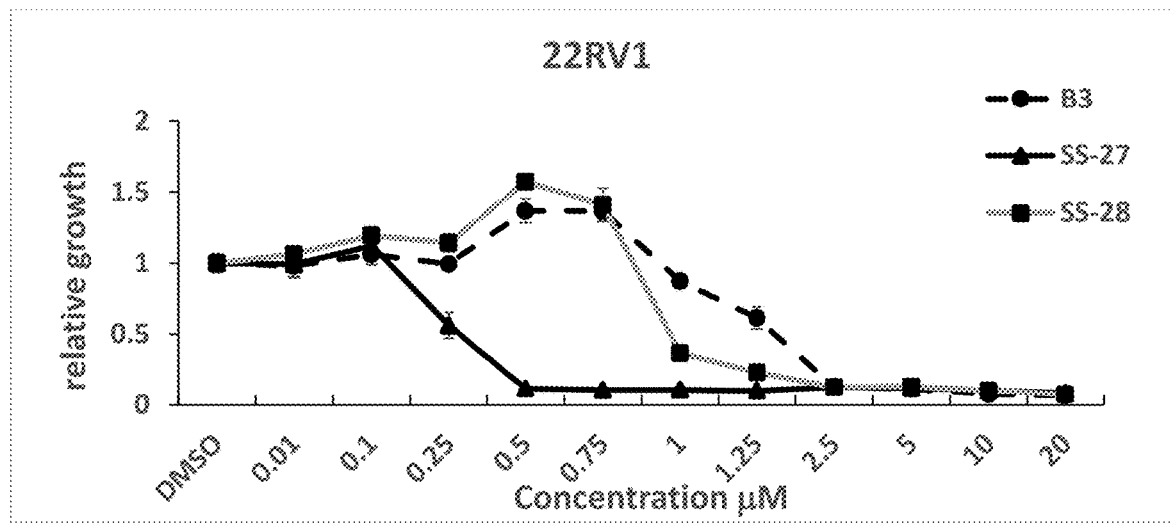
FIGS. 2A-2C show MTT assays of SS27, SS28, and B3 on 22RV1 (human prostate cancer cells) and 786O (human kidney cancer cells).
Figure 2B:
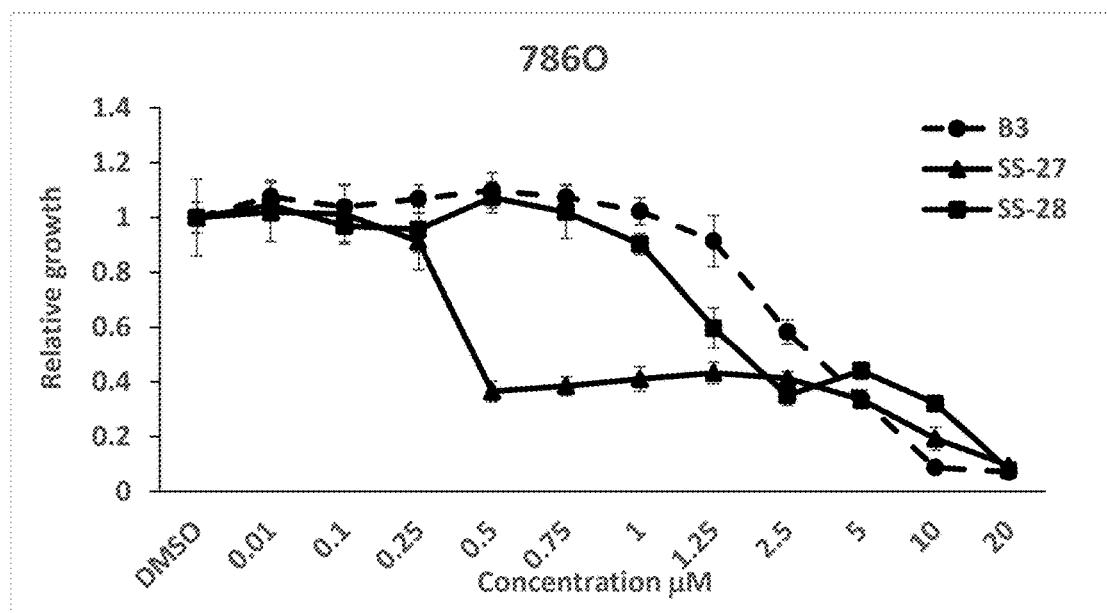
Figure 2C:
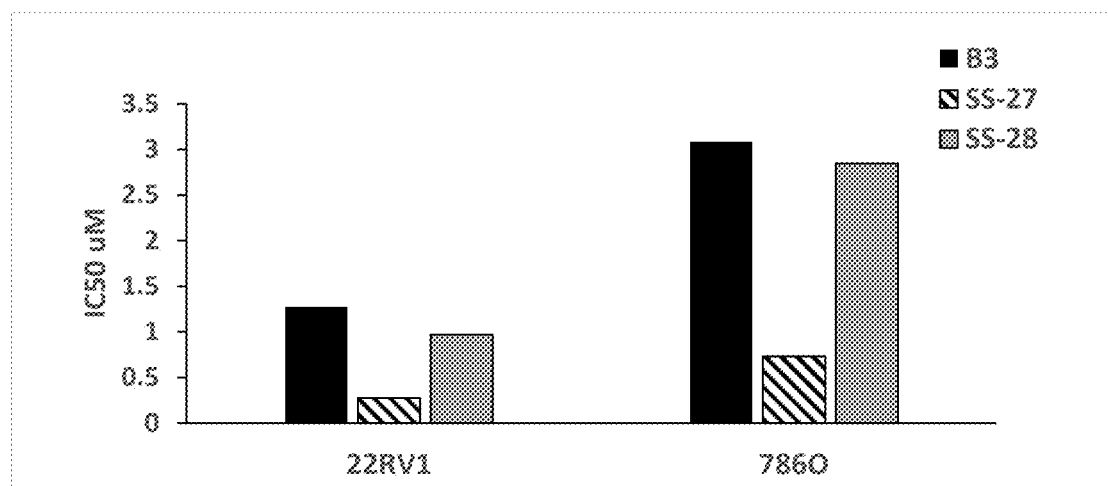
Figure 3:
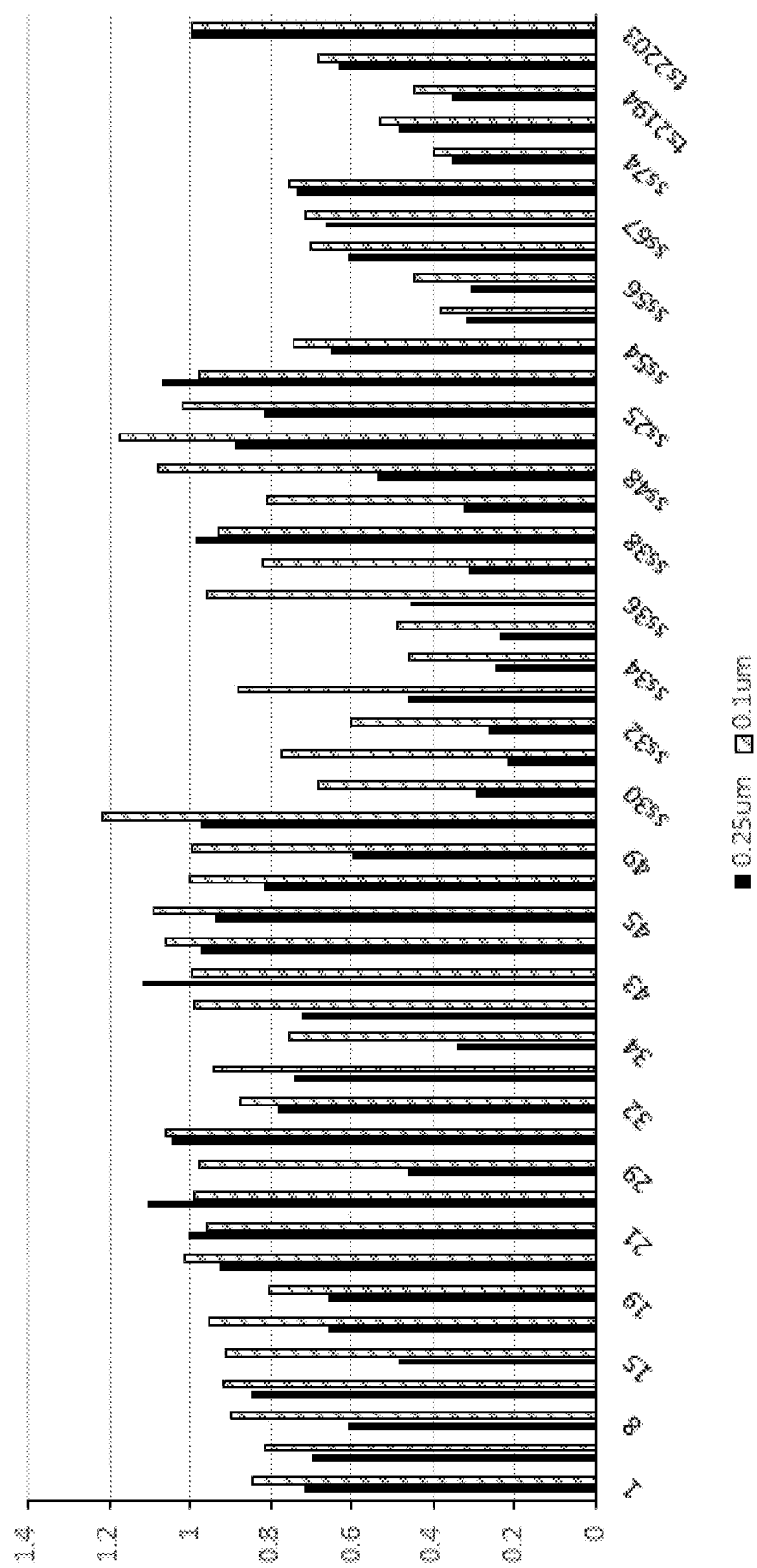
FIG. 3 shows MTT assays of 8-hydroxyquinoline-containing compounds on prostate cancer cells (22RV1).
Figure 4:
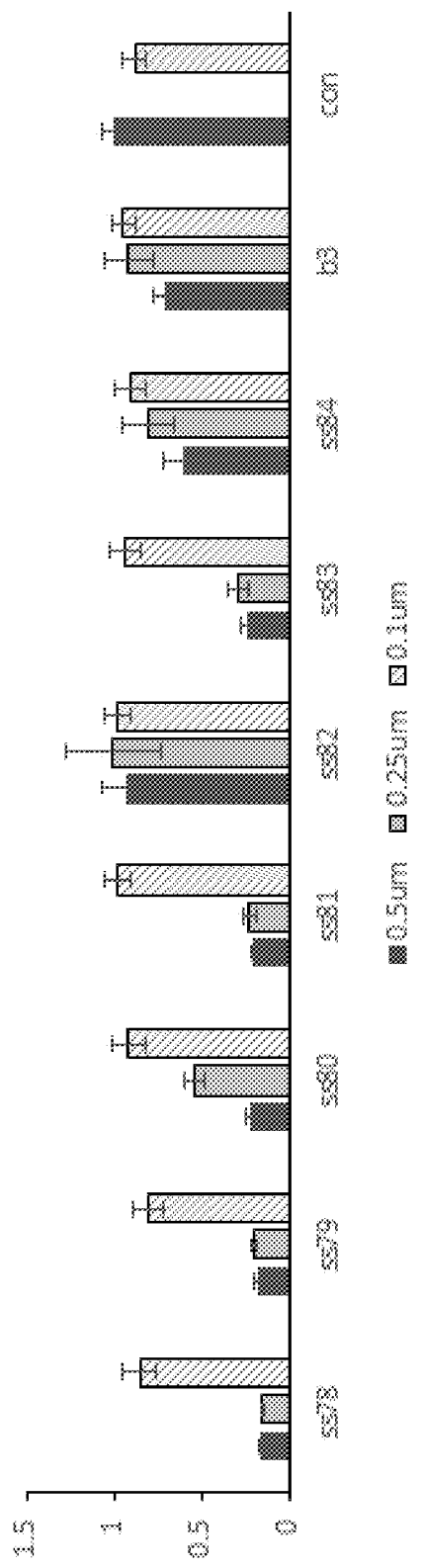
FIG. 4 shows MTT assays of SS78, SS79, SS80, SS81, SS82, SS83, SS84 and B3 on prostate cancer cells (22RV1).
Figure 5:
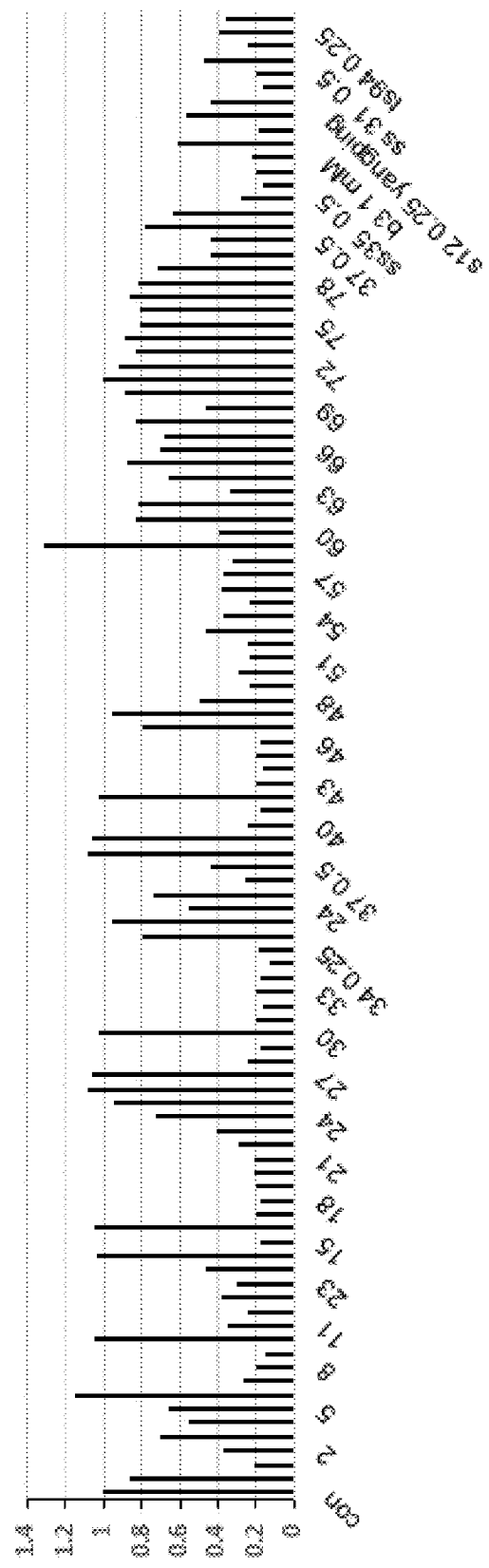
FIG. 5 shows MTT assays of certain 8-hydroxyquinoline-containing compounds on prostate cancer cells (22RV1).
Figure 6:
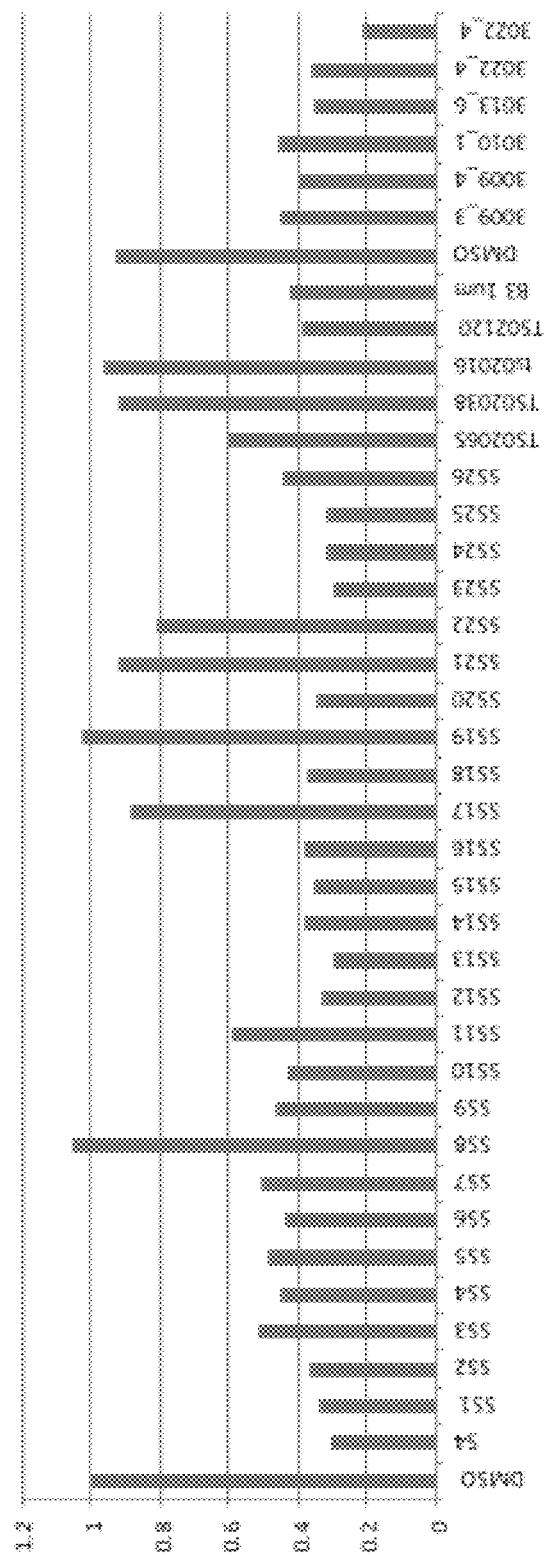
FIG. 6 shows MTT assays of certain 8-hydroxyquinoline-containing compounds on prostate cancer cells (22RV1).
Figure 7:
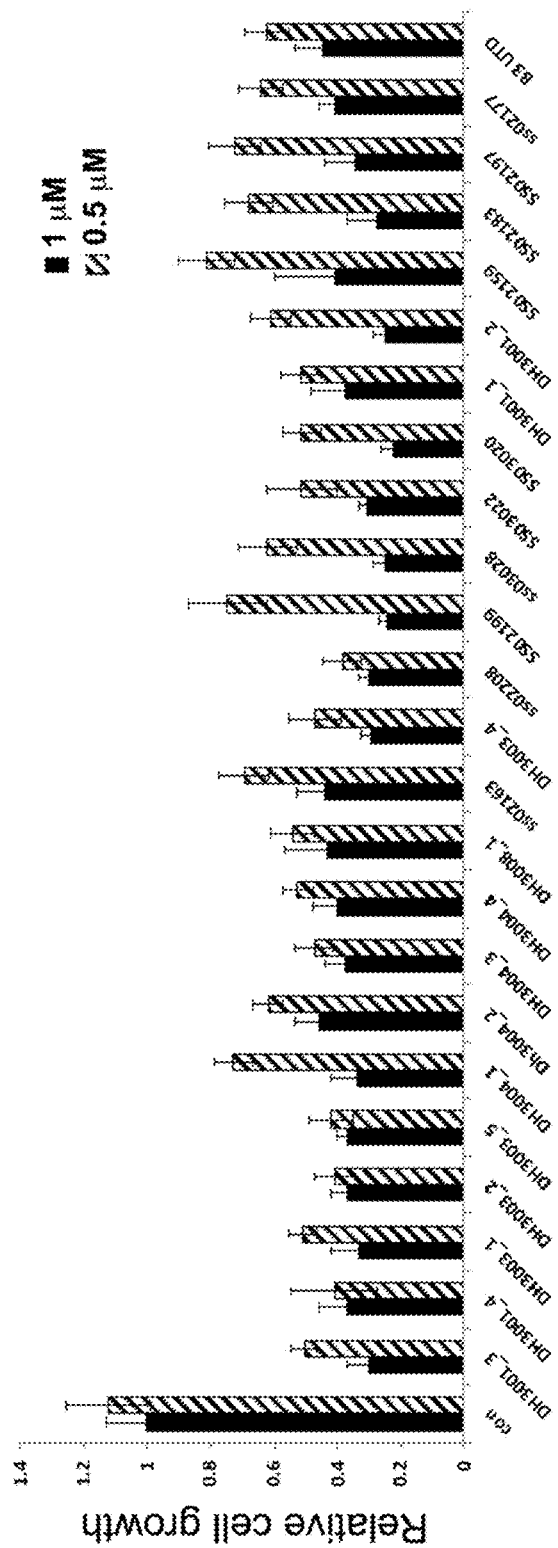
FIG. 7 shows MTT assays of 8-hydroxyquinoline-containing compounds on prostate cancer cells (22RV1).
Figure 8:
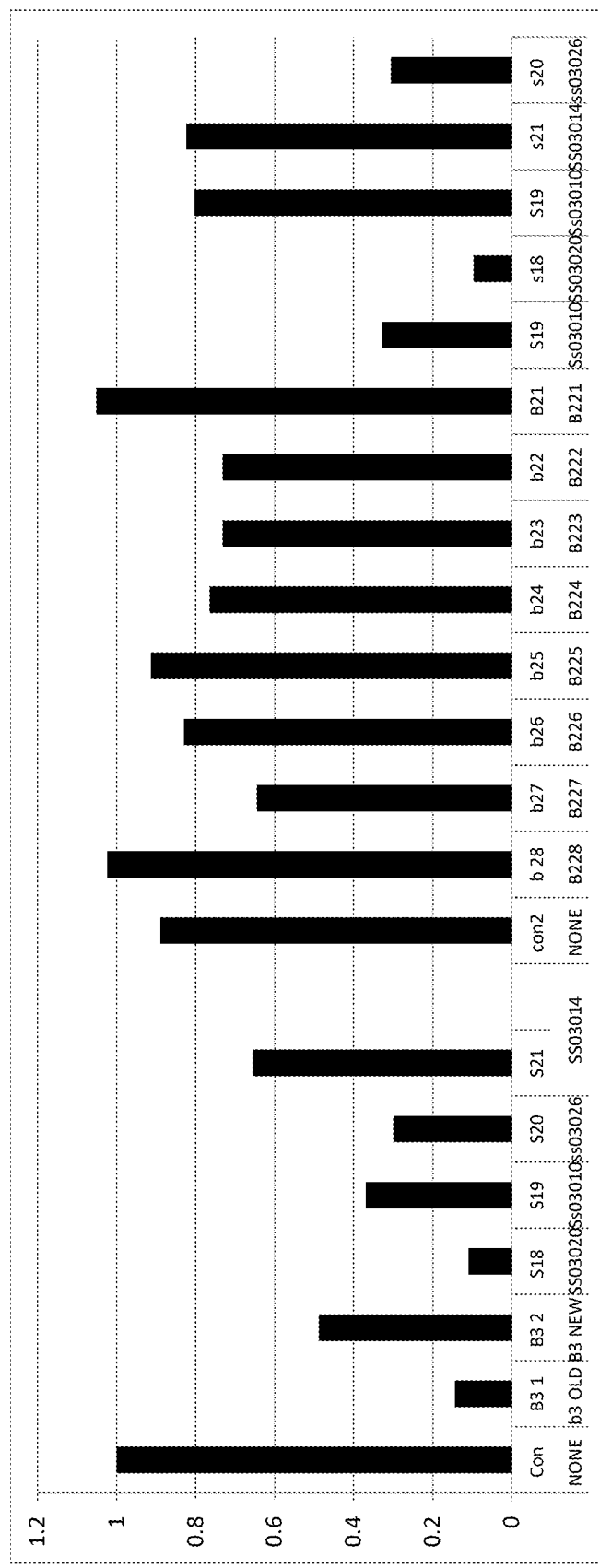
FIG. 8 shows MTT assays of 8-hydroxyquinoline-containing compounds on prostate cancer cells (22RV1).
Figure 9:
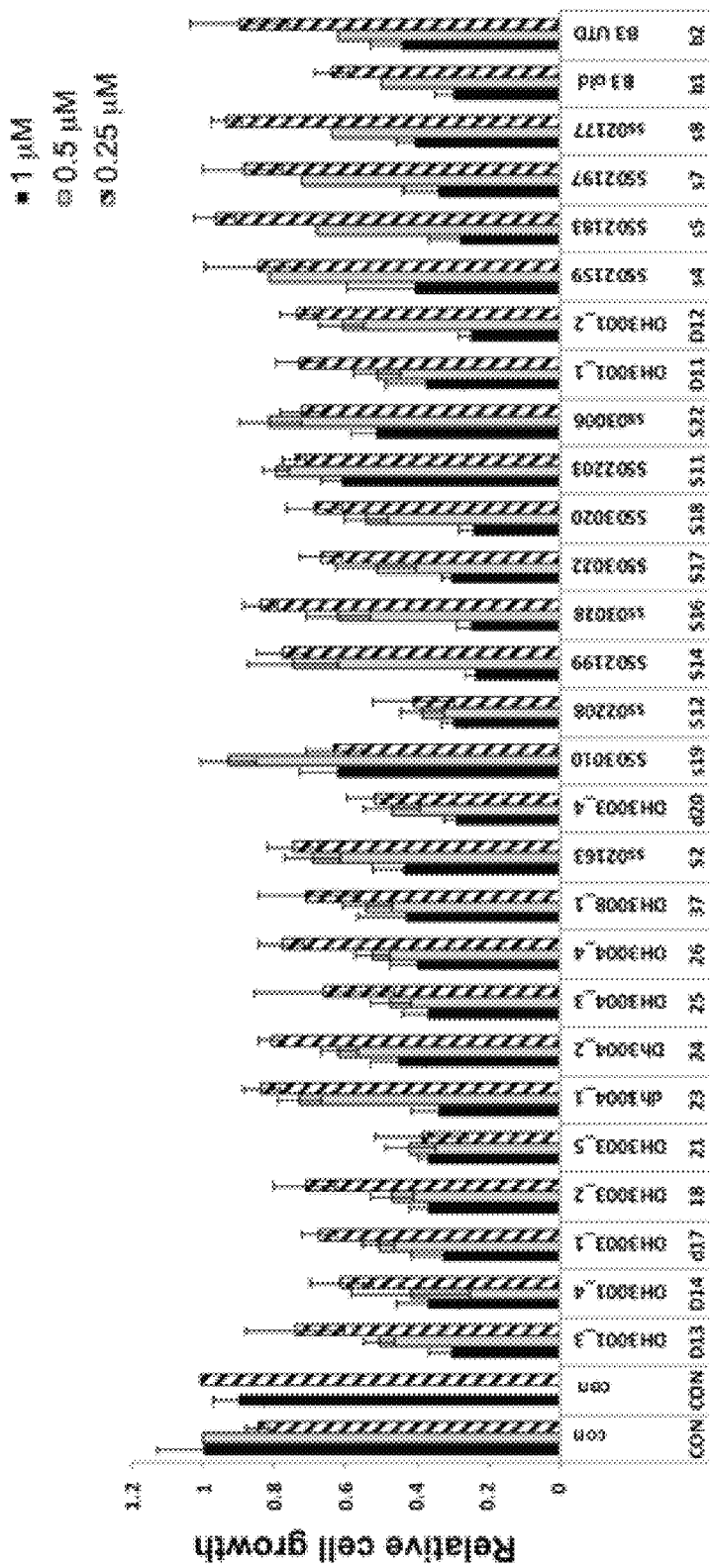
FIG. 9 shows MTT assays of 8-hydroxyquinoline-containing compounds on prostate cancer cells (22RV1).
Figure 10A:
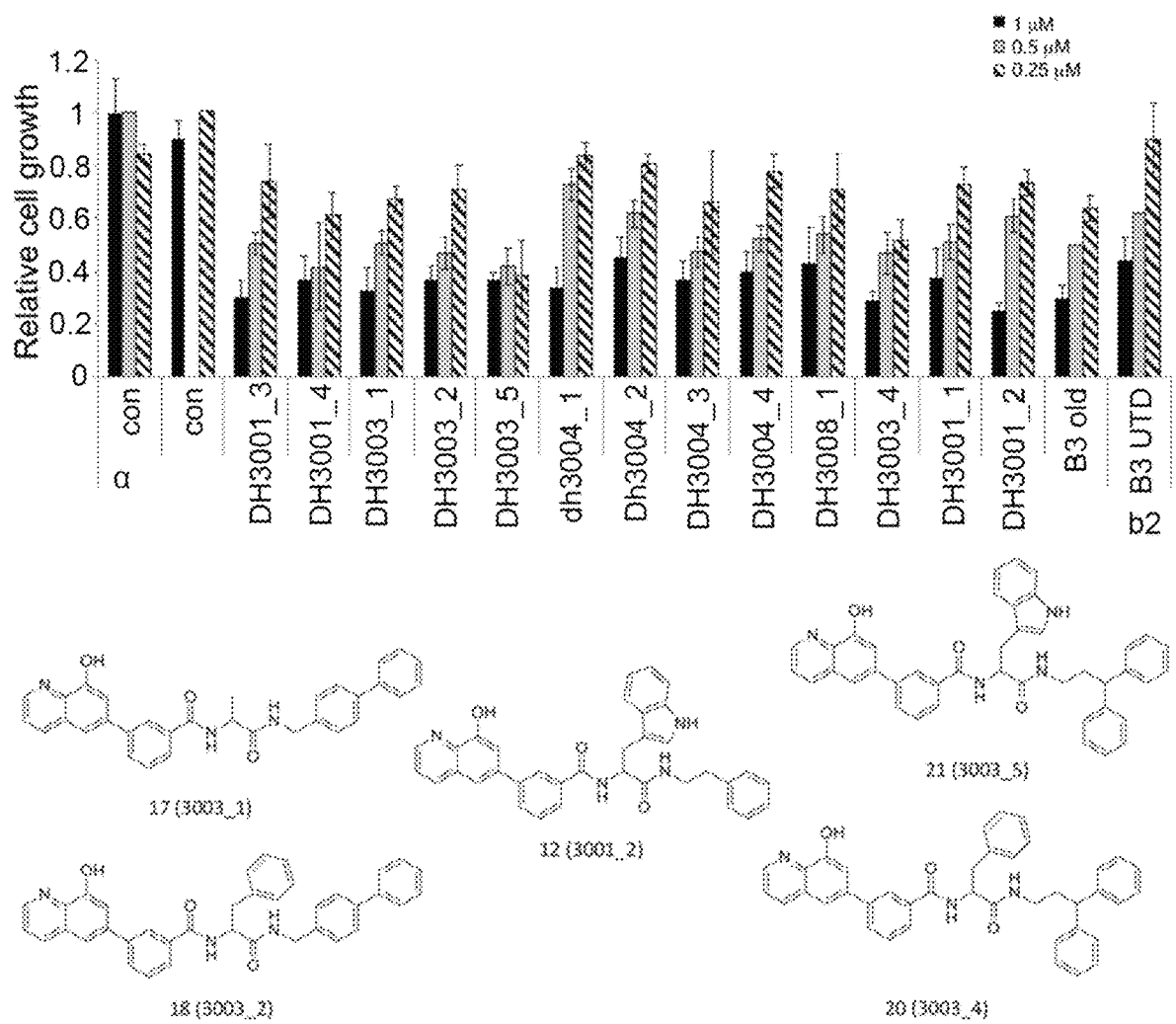
FIGS. 10A-10C show MTT assays of various 8-hydroxyquinoline-containing compounds disclosed herein.
Figure 10B:
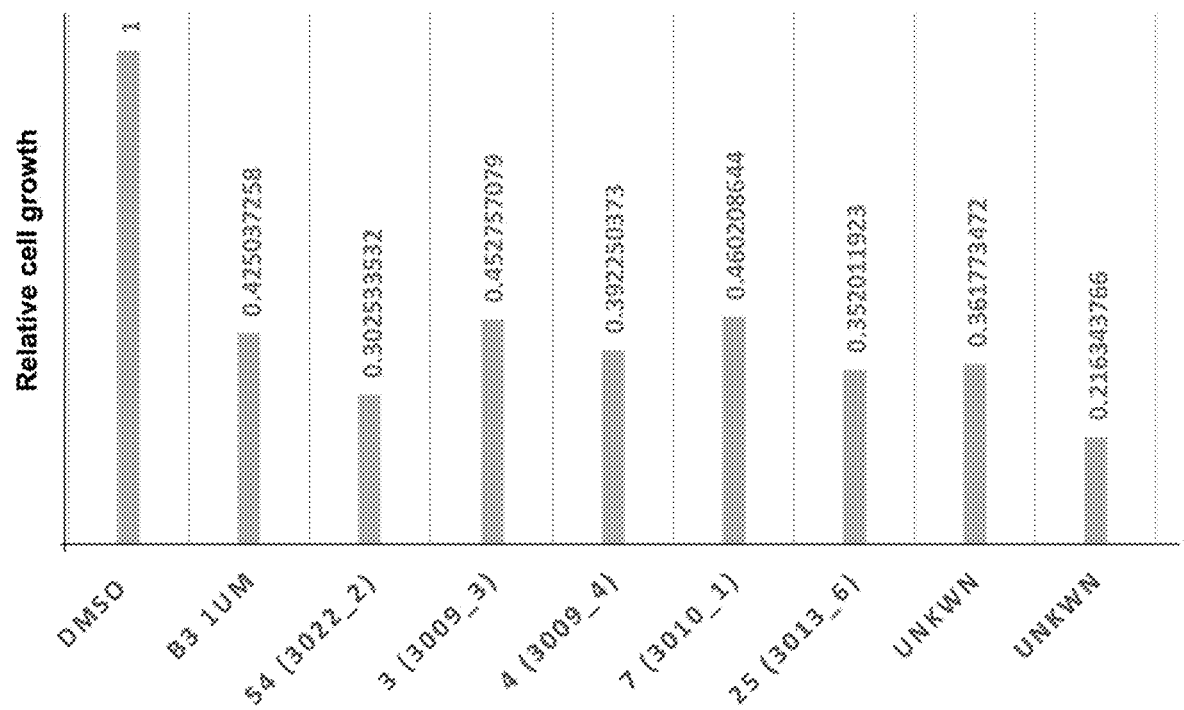
Figure 10B:
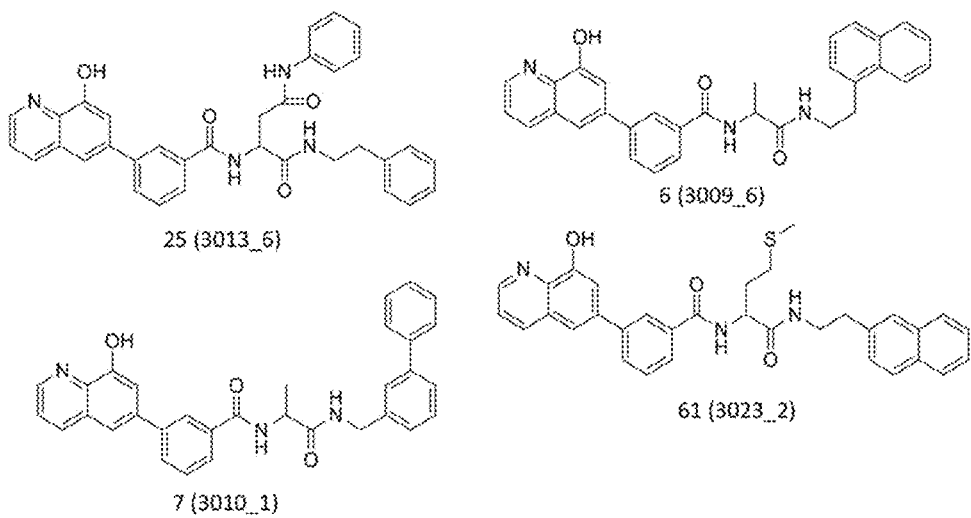
Figure 10C:
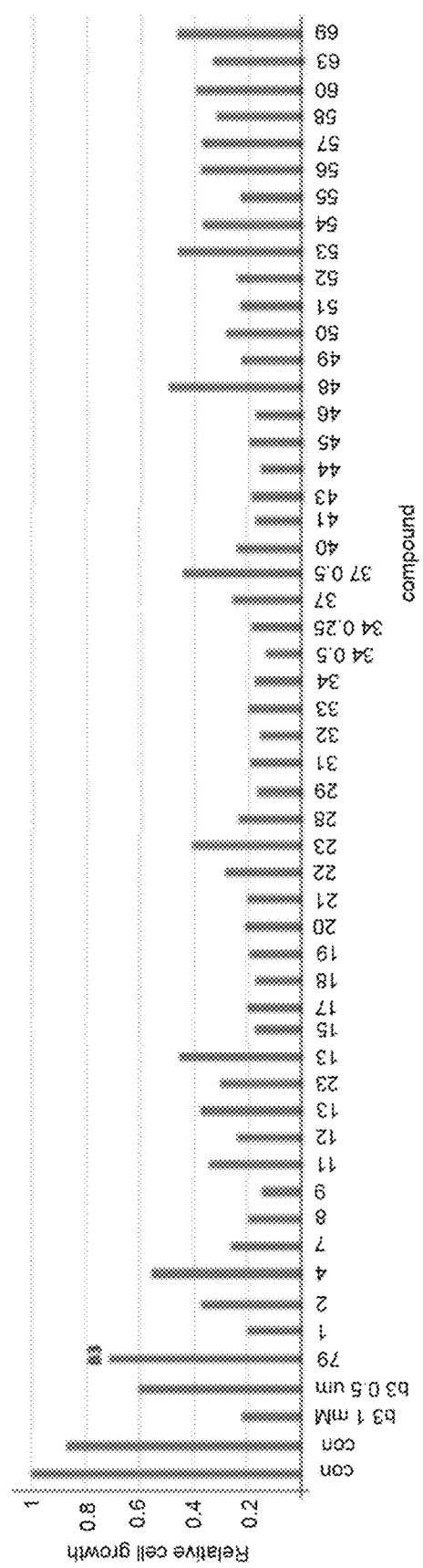
Figure 11A:
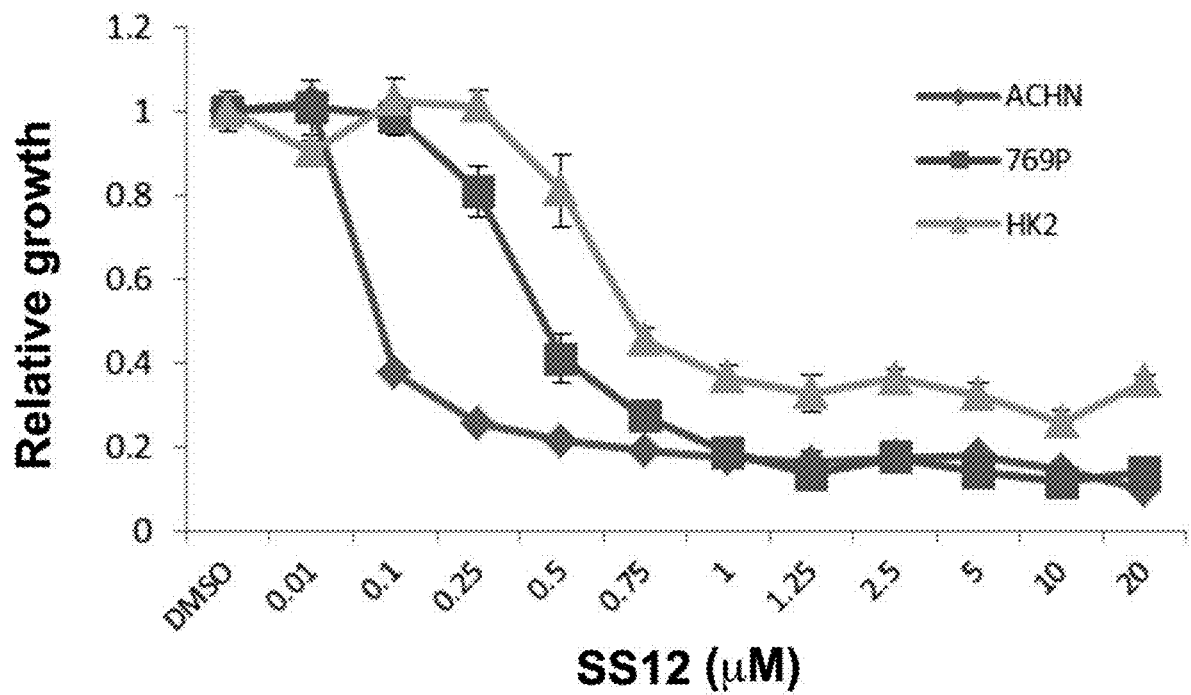
FIGS. 11A-11C show MTT assays of kidney cancer cell lines (ACHN, 769P, and HK2) using various concentrations of compounds SS12 and D37 disclosed herein for 72 hours versus a DMSO control. $IC_{50}$ was calculated using Prism Graphpad (n=3±SEM).
Figure 11B:
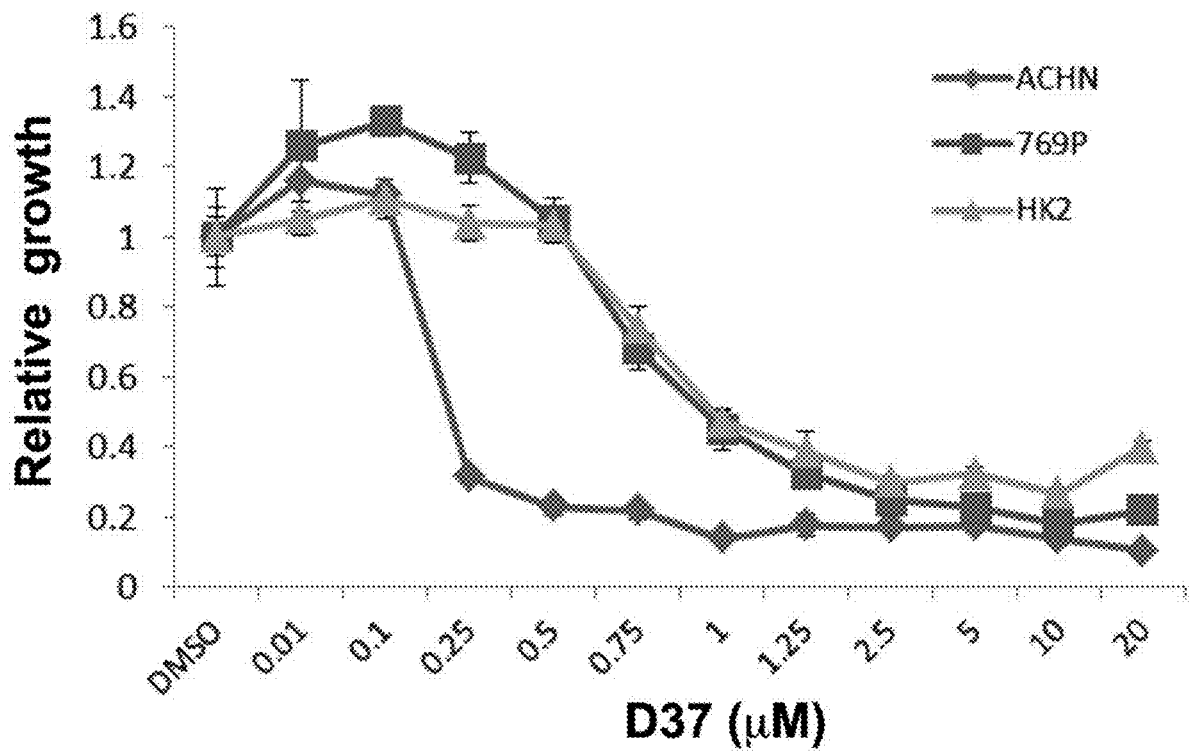
Figure 11C:
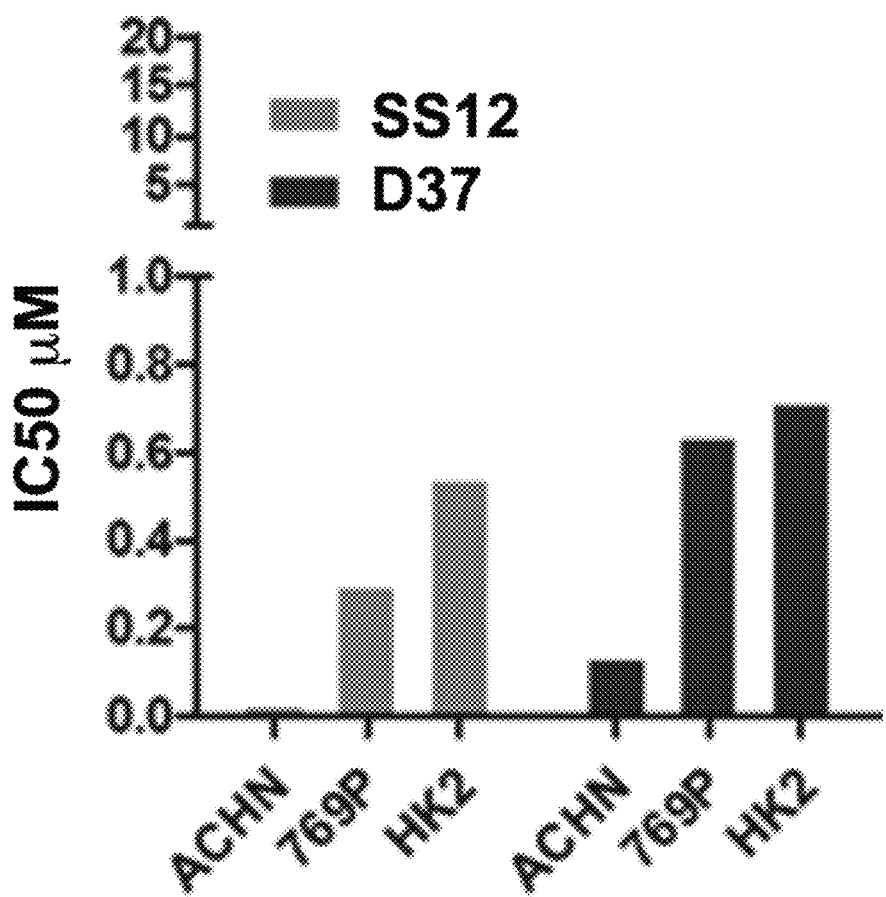

All publications, patents, and patent applications mentioned in this specification are herein incorporated by reference to the same extent as if each individual publication, patent, or patent application was specifically and individually indicated to be incorporated by reference.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl(n-propyl), 1-methylethyl(iso-propyl), 1-butyl(n-butyl), 1-methylpropyl(sec-butyl), 2-methylpropyl(iso-butyl), 1,1-dimethylethyl(tert-butyl), 1-pentyl(n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$—N(R$^a$)$_2$(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., C1-C8 alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) .pi.-electron system in accordance with the Huckel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2), —$R^b$—S(O)$_t R^a$ (where t is 1 or 2) and —$R^b$—S(O)$_t N(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula $R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—-bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2), —$R^b$—S(O)$_t R^a$ (where t is 1 or 2) and —$R^b$—S(O)$_t N(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula $R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to, and the like.

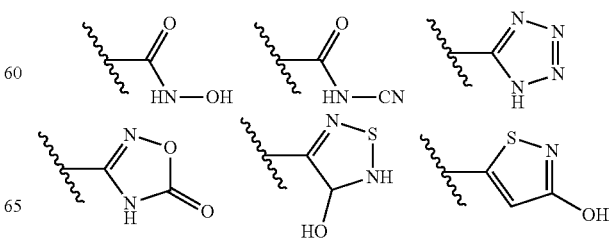

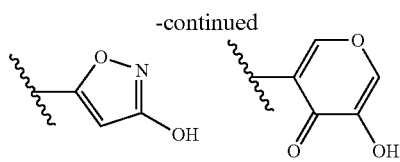

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^a$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R_b$—$S(O)_tR^a$ (where t is 1 or 2) and —$R^b$—$S(O)_tN(R^a)_2$ (where t is 1 or 2), where each Ra is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) .pi.-electron system in accordance with the Huckel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10α-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula $R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

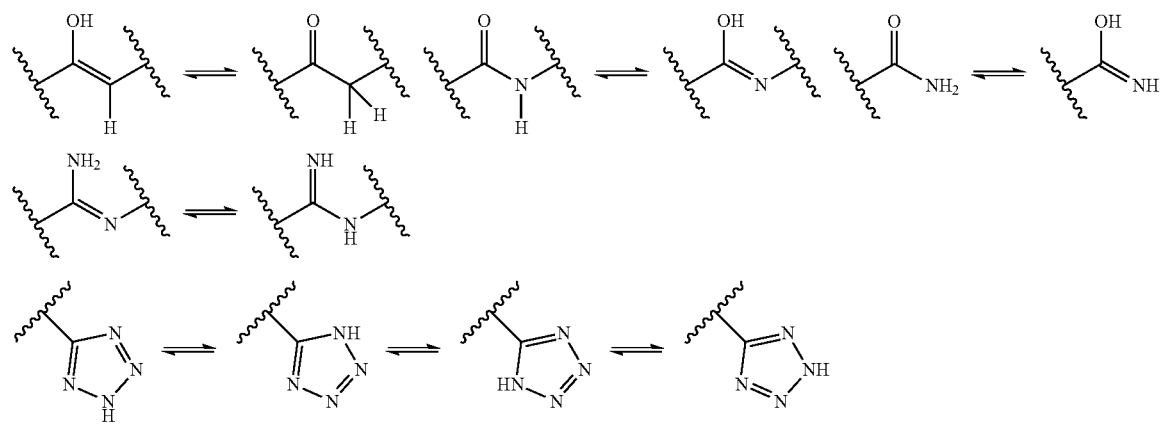

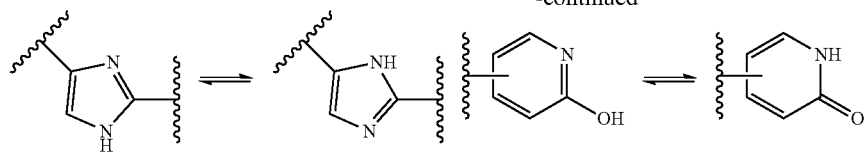

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

The term "radical," which as used in the specification and concluding claims, refers to a fragment, group, or substructure of a molecule described herein, regardless of how the molecule is prepared. For example, a 2,4-thiazolidinedione radical in a particular compound has the structure:

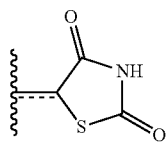

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^{2}H$, $^{3}H$, $^{13}C$, $^{14}C$, $^{5}N$, $^{18}O$, $^{17}O$, $^{35}S$, $^{18}F$, and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

In some aspects, a structure of a compound can be represented by a formula:

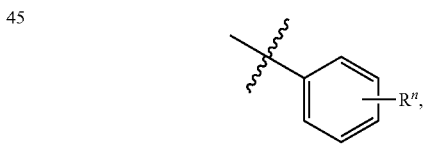

which is understood to be equivalent to a formula:

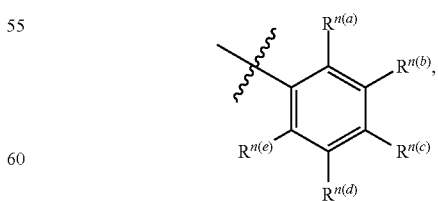

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

"Pharmaceutically acceptable salt" includes both acid and base addition salts. A pharmaceutically acceptable salt of any one of the substituted imidazole-pyridine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

As used herein, "administering" can refer to an administration that is oral, topical, intravenous, subcutaneous, transcutaneous, transdermal, intramuscular, intra joint, parenteral, intra-arteriole, intradermal, intraventricular, intraosseous, intraocular, intracranial, intraperitoneal, intralesional, intranasal, intracardiac, intraarticular, intracavernous, intrathecal, intravitreal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

8-Hydroxyquinoline Derivative Compounds/Analogs as KDM4 Inhibitors

The present disclosure provides a new series of 8-hydroxyquinoline derivatives/analogs with unique and diverse substituents based on both rational drug design approach and virtual screening campaigns. Many compounds with remarkably high potency were identified from testing them on prostate cancer cell lines. Some of them were found to be quite stable under biological assay conditions and showed significantly strong activity in inhibiting tumor cell growth (both prostate and kidney cancer cells, e.g., LnCap and 22rv1 cell lines). One of the leading compounds, SS27 (also named as oSS12, SS79, SS79N, SS81, or 17l) showed superior cell growth inhibition and/or excellent anti-proliferation activities on prostate and kidney cancer cells (e.g., $IC_{50}$ values below 200 nM, which is more than 20-fold increase compared to other 8-hydroxyquinoline-containing compounds, such as B3 that was previously reported) and favorable in vivo efficacy. This compounds also showed much better efficacy than the known GlaxoSmithKline (GSK) KDM6B inhibitor.

8-Hydroxyquinoline Derivative Compounds/Analogs as KDM4 Inhibitors are described herein. These compounds/inhibitors, and compositions comprising these compounds/inhibitors, are useful for the treatment of cancer and neoplastic diseases. The compounds/inhibitors described herein may, therefore, be useful for treating prostate cancer, kidney cancer, bladder cancer, breast cancer, lung cancer and/or melanoma and the like.

Certain embodiments of the present disclosure provide a KDM4 inhibitor, or a pharmaceutical acceptable salt thereof, having a structure given by the formula:

In certain embodiments, the present disclosure provides a KDM4 inhibitor, or a pharmaceutically acceptable salt thereof, having a structure given by the formula:

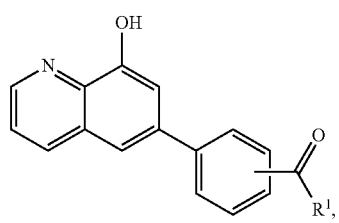

where $R^1$ is a group having a structure selected from the formulas:

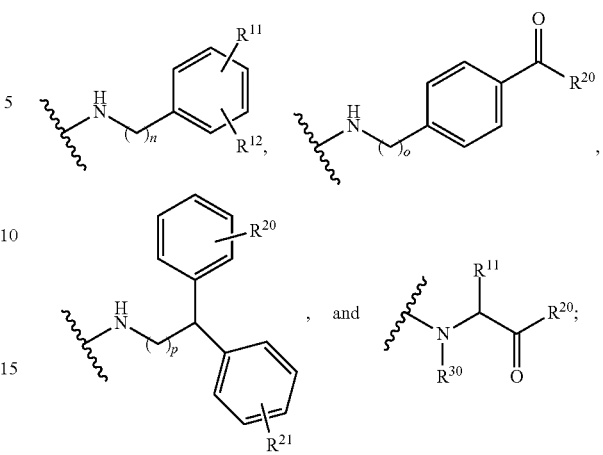

where n is from 0 to 10;
where o is from 0 to 10;
where p is from 0 to 10;
where each of $R^{11}$ and $R^{12}$, when present, is independently selected from hydrogen, halogen, hydroxy, thiol, cyano, amino, nitro, C1-C10 alkylamide, carbonyl, carboxylic acid, C1-C20 alkyl, C2-C20 alkenyl, C2-C20 alkynyl, C3-C20 cycloalkyl, C3-C20 heterocycloalkyl, aryl, heteroaryl, arylalkyl, and alkylaryl, and where each occurrence of C1-C10 alkylamide, C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl is optionally substituted with halogen, hydroxy, alkoxy, thiol, thioether, cyano, amino, carboxylic acid, ester, amide, carbamate, urea, guanidine, aryl substituted organic hydrazone, lactam substituted aryl group, nitro, —O—(C1-C6 alkyl), —NR$^{40}$R$^{41}$, C1-C6 alkylhydroxyl, C1-C6 haloalkyl, C1-C6 cycloalkyl, C1-C6 alkylamino, —OR$^{40}$, —COR$^{40}$, —CO$_2$R$^{40}$, aryl, and —CONR$^{40}$R$^{41}$;

where each of $R^{20}$ and $R^{21}$, when present, is selected from hydrogen, C1-C20 alkyl, C2-C20 alkenyl, C2-C20 alkynyl, C3-C20 cycloalkyl, C3-C20 heterocycloalkyl, aryl, heteroaryl, C1-C20 alkylheteroaryl, arylalkyl, alkylaryl, —P(=O)(OH)R$^{40}$R$^{41}$, —SR$^{40}$, —S(=O)$_2$R$^{40}$R$^{41}$, and —NR$^{40}$R$^{41}$ and where each occurrence of C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl is optionally substituted with halogen, hydroxy, thiol, cyano, amino, carboxylic acid, ester, amide, carbamate, urea, guanidine, nitro, —O—(C1-C6 alkyl), —NR$^{40}$R$^{41}$, C1-C6 alkylhydroxyl, C1-C6 haloalkyl, C1-C6 alkylamino, C1-C6 cycloalkyl, C3-C20 heterocycloalkyl, —COR$^{40}$, —CO$_2$R$^{40}$, aryl, or —CONR$^{40}$R$^{41}$;

where $R^{30}$, when present, is selected from hydrogen, C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl where each occurrence of C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl is optionally substituted with halogen, hydroxy, thiol, cyano, amino, nitro, —O—(C1-C6 alkyl), carboxylic acid, ester, amide, carbamate, urea, guanidine; and where each occurrence of $R^{40}$ and $R^{41}$ is independently selected from hydrogen, C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl where each occurrence of C1-C20 alkyl, C2-C20 alkenyl, C2-C20 alkynyl, C3-C20 cycloalkyl, C3-C20 heterocycloalkyl, aryl, heteroaryl, arylalkyl, or alkylaryl is optionally substituted with halogen, hydroxy, thiol, cyano, amino, nitro, —O—(C1-C6 alkyl), halogen-substituted —O—(C1-C6 alkyl), —O—(C1-C6 aryl), halogen-substituted —O—(C1-C6 aryl), carboxylic acid, ester, amide, carbamate, urea, guanidine, C1-C4 linear or branched alkyl or haloalkyl, or C3-C6 cycloalkyl optionally substituted with a C1-C3 alkyl group or a C6 aryl group;

provided that the compound does not have a structure given by the formula:

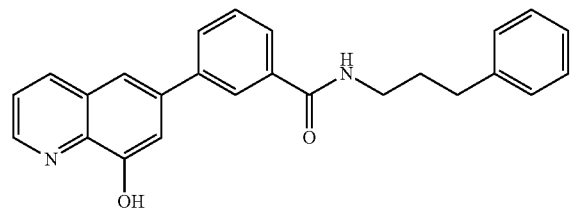

In other embodiments, the KDM4 inhibitor or pharmaceutically acceptable salt thereof includes the group of compounds wherein $R^1$ is

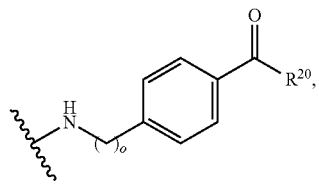

o is 1, $R^{20}$ is $NR^{40}R^{41}$, $R^{40}$ is hydrogen, and $R^{41}$ is C1-C20 alkyl substituted with C3-C6 cycloalkyl optionally substituted with a C1-C3 alkyl group, a C6 aryl group, or a C1-C4 linear or branched alkyl or haloalkyl group. Non-limiting examples of this group of compounds include the following:

(SS30)
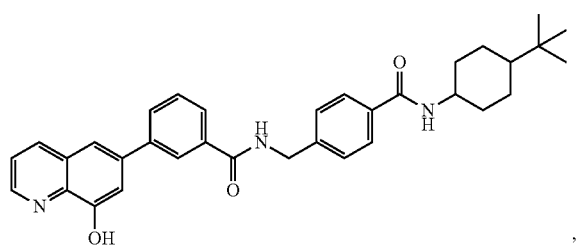

(SS31)
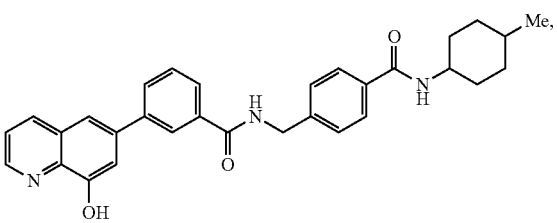

(SS32)
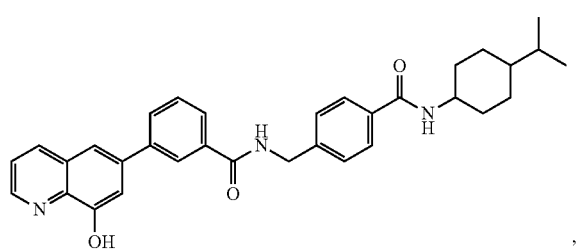

(SS33)
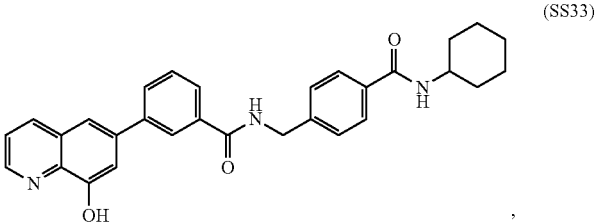

(SS34)
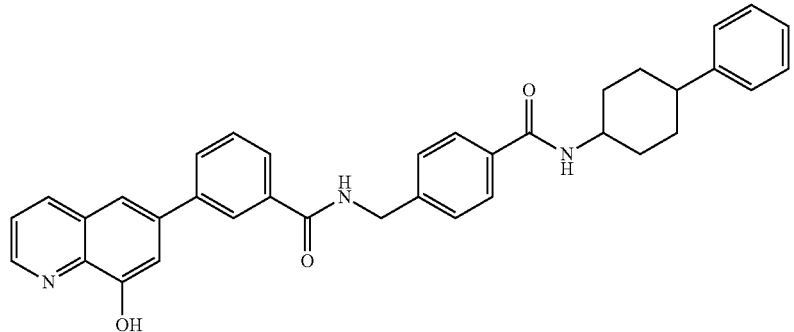

-continued
(SS35)
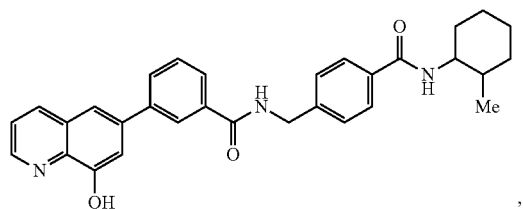
(SS27, oSS12, SS02208, SS79, SS79N, SS81, or 171)
(SS36)
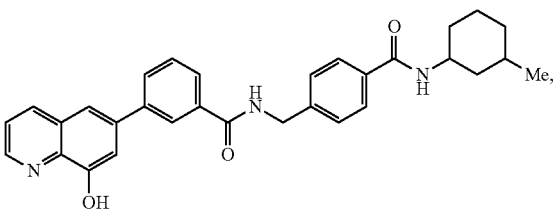
(SS46)
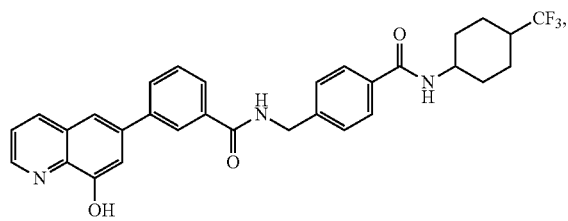
(SS48)
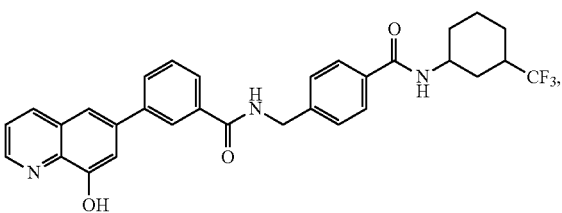
(SS49)
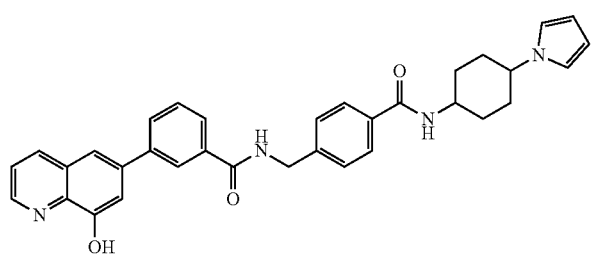
(SS51)
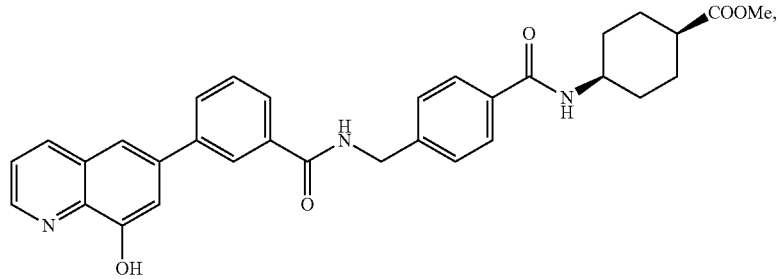
(SS54)
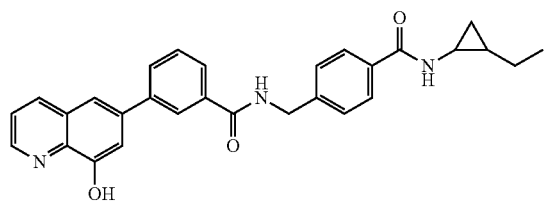
(SS55)
(SS55)
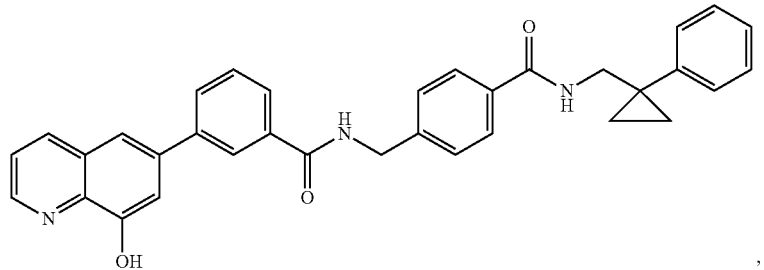
, and -continued

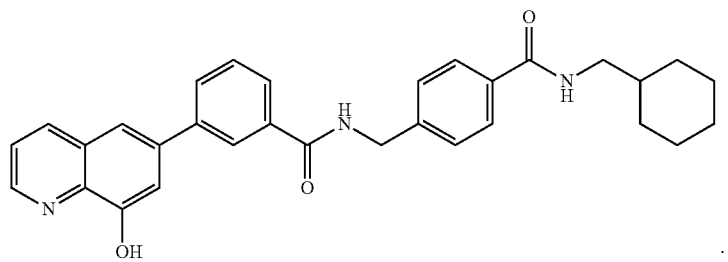

(SS37 or SS2097)

In other embodiments, the KDM4 inhibitor or pharmaceutically acceptable salt thereof includes the group of compounds wherein $R^1$ is

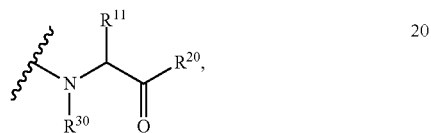

$R^{30}$ is hydrogen, $R^{11}$ is alkyl, hydrogen, alkylthioether, alkyl amide, hydroxy substituted alkyl aryl, or hydroxy substituted alkyl, $R^{20}$ is $NR^{40}R^{41}$, $R^{40}$ is hydrogen, and $R^{41}$ is alkylaryl. Non-limiting examples of this group of compounds include the following:

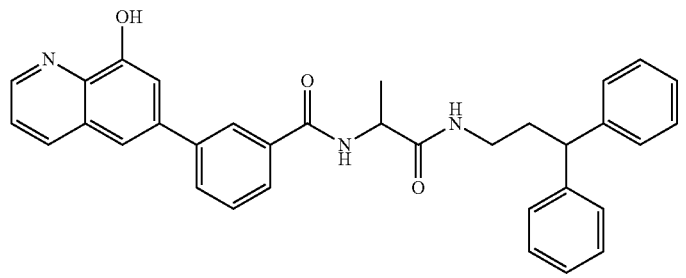

(3028-5)

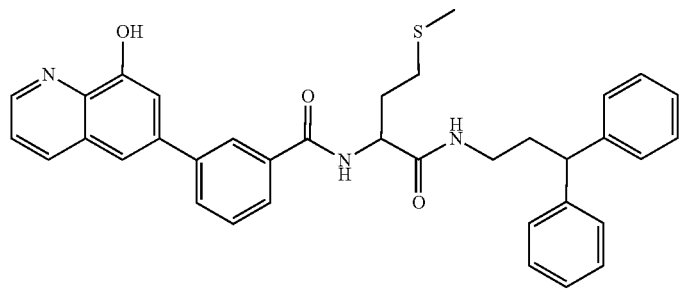

(3028-6)

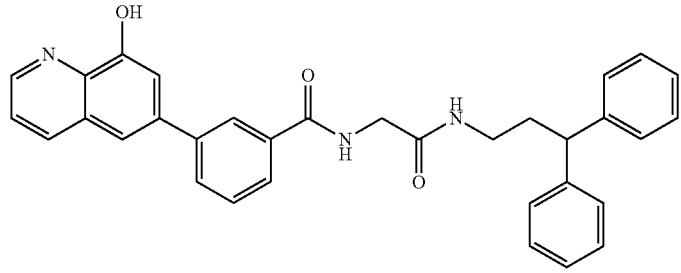

(3029-3)

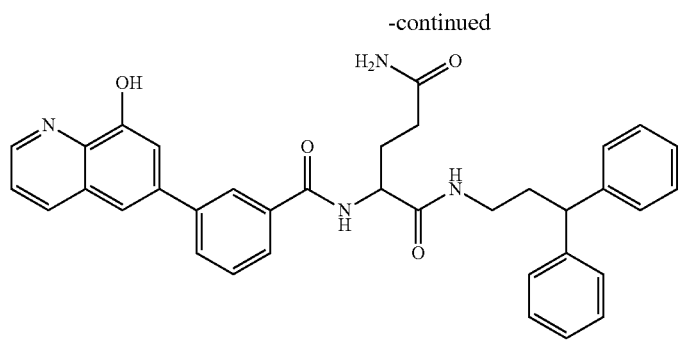
(3029-5)
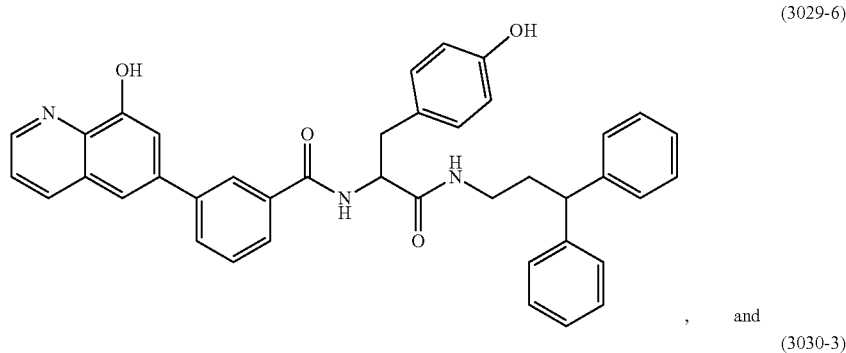
(3029-6), and
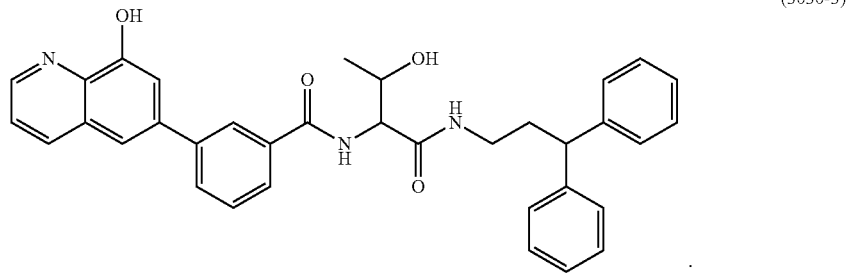
(3030-3).
In other embodiments, the KDM4 inhibitor or pharmaceutically acceptable salt thereof includes the group of compounds wherein $R^1$ is
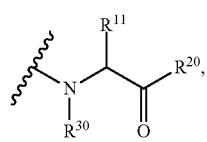
$R^{30}$ is H, $R^{11}$ is alkyl heteroaryl, $R^{20}$ is $NR^{40}R^{41}$, $R^{40}$ is hydrogen, and $R^{41}$ is substituted or unsubstituted alkylaryl. Non-limiting examples of compounds in this group include the following:
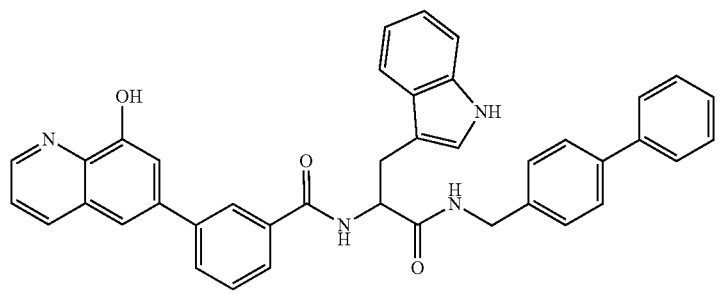
(3025-1), -continued
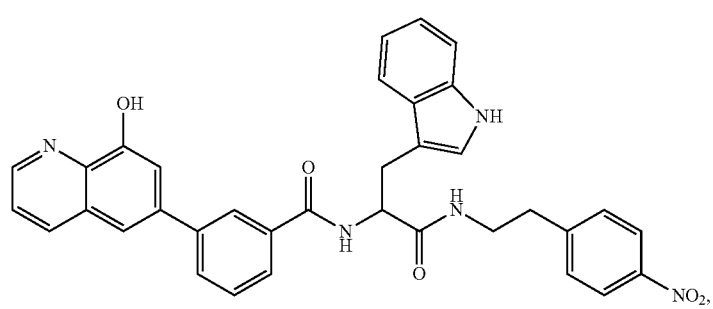
(3025-2)
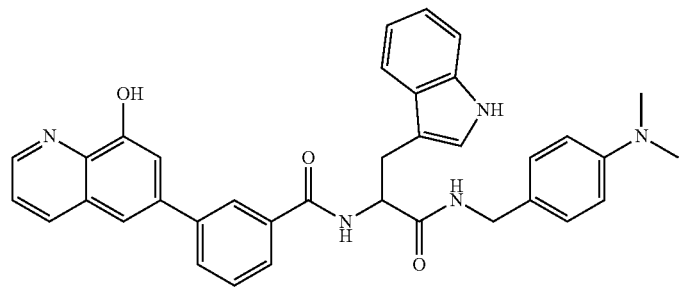
(3025-3)
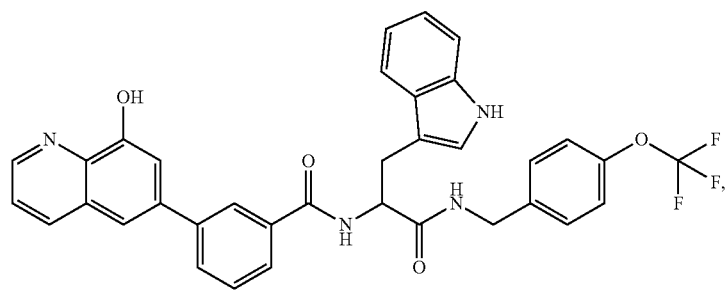
(3025-6)
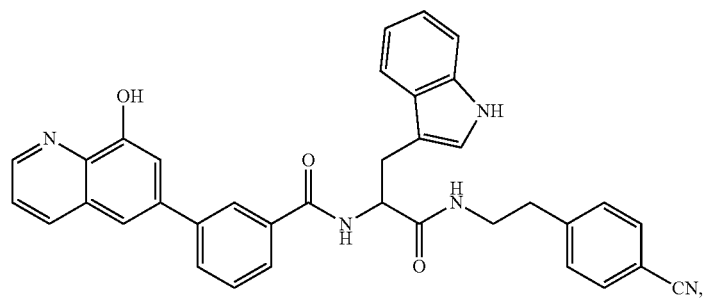
(3026-3)
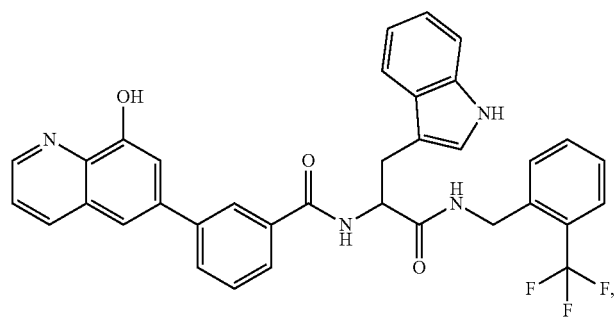
(3026-6)

-continued
(3027-1)
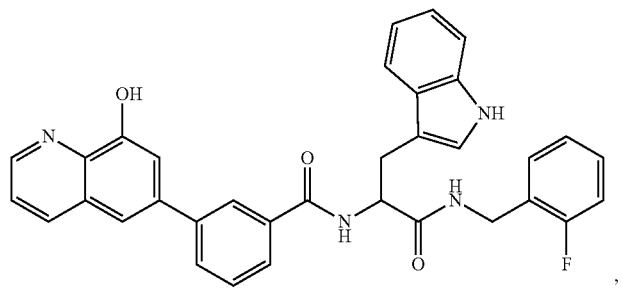
(3027-2)
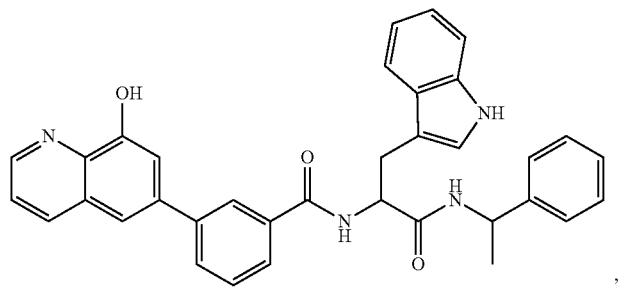
(3027-3)
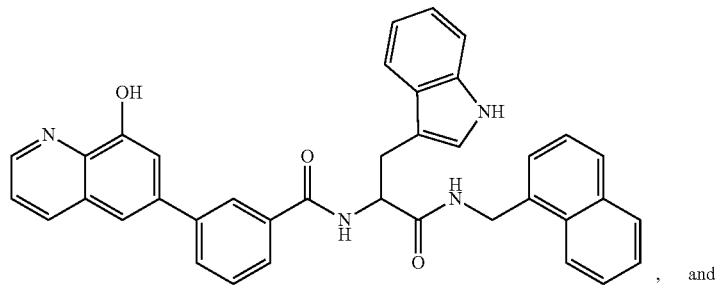, and
(3027-4)
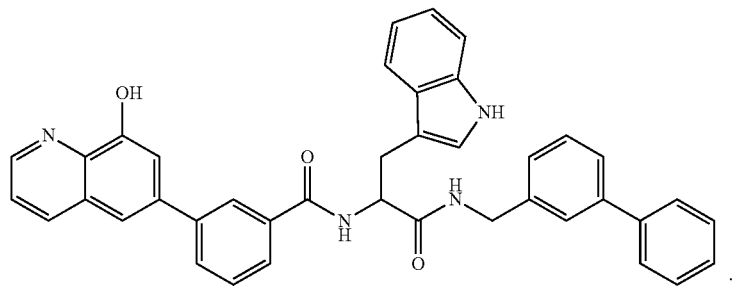.
In other embodiments, the KDM4 inhibitor or pharmaceutically acceptable salt thereof includes the group of compounds wherein R1 is
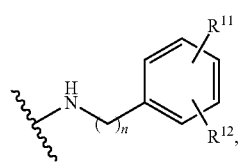
n is from 0 to 4, and $R^{11}$ and $R^{12}$ are hydrogen. Non-limiting examples of compounds in this group include the following:

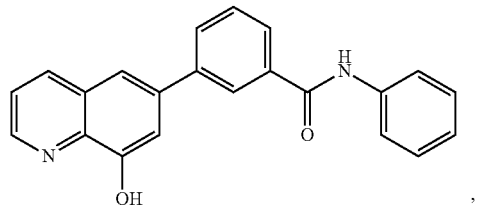 (SS04190 or SS-61)

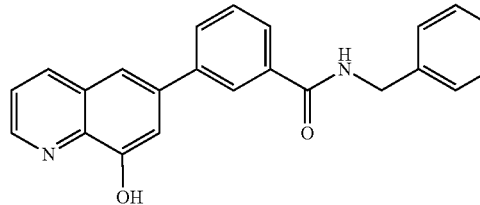 (SS04191 or SS-62)

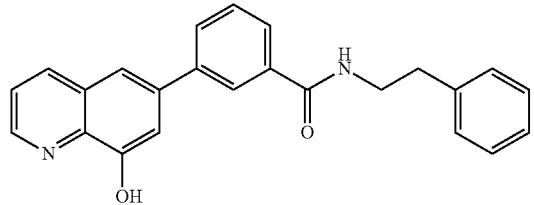 (SS04194 or SS-64)

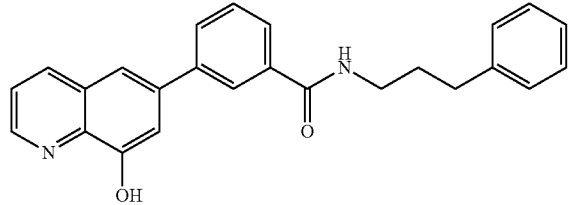 (B-3)

and

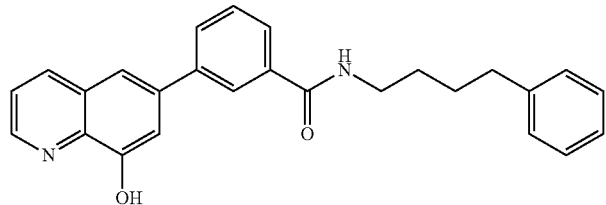 (SS04193 or SS-63)

In other embodiments, the KDM4 inhibitor or pharmaceutically acceptable salt thereof includes the group of compounds wherein $R^1$ is

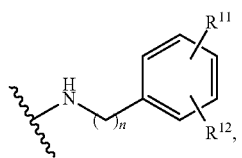

n is 1, $R^{11}$ is hydrogen or alkoxy, $R^{12}$ is cyano, alkoxy, substituted amine, $COR^{40}$, or $OR^{40}$, and $R^{40}$ is aryl, heteroaryl, or aryl substituted with a halogen. Non-limiting examples of compounds in this group include the following:

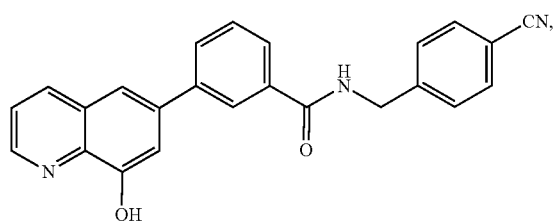
(SS02106)
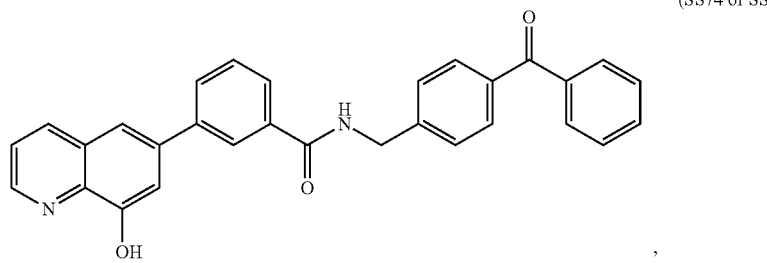
(SS74 or SS02132)
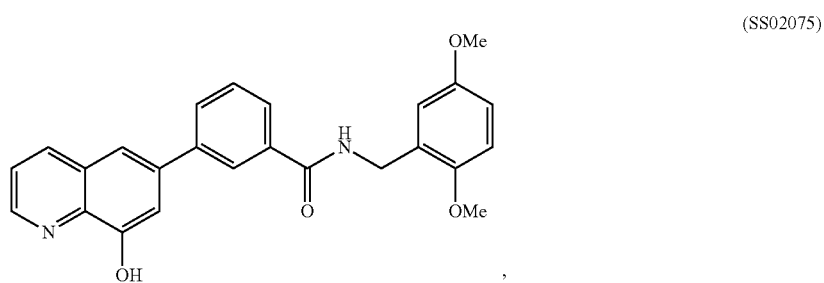
(SS02075)
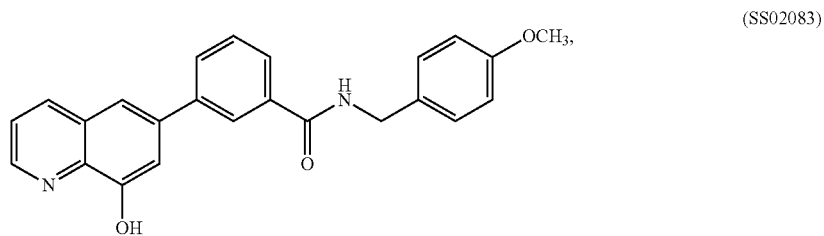
(SS02083)
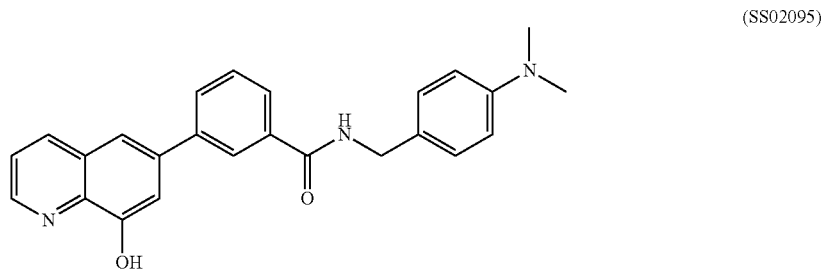
(SS02095)

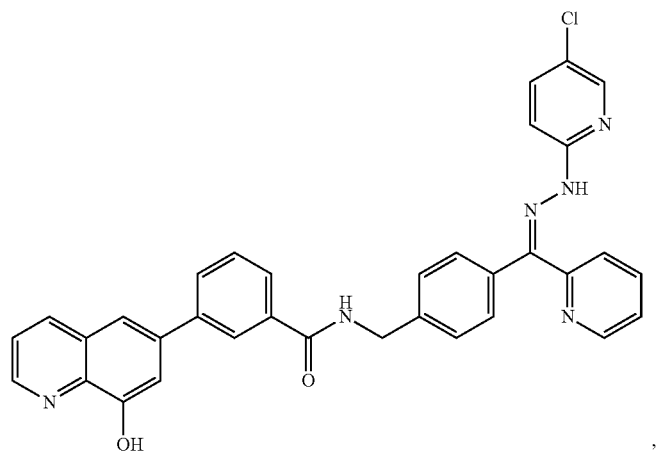
(SS1)
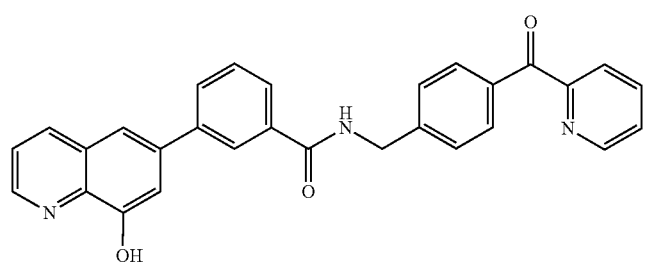
(SS2)
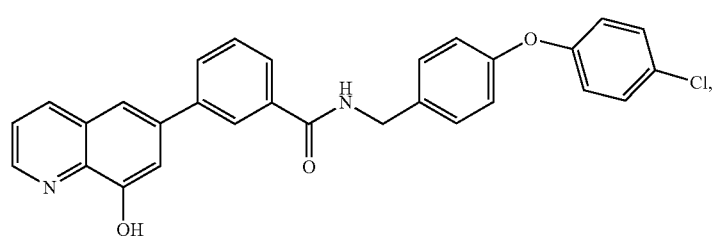
(SS12 or SS03154)
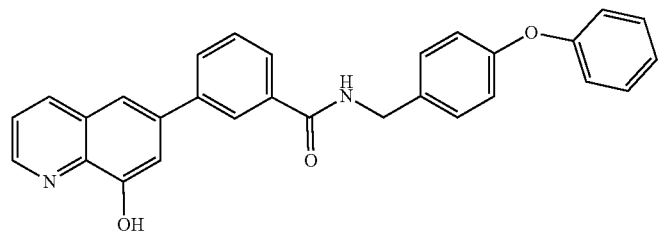
(SS13 or SS03152)

(SS14 or SS03156)

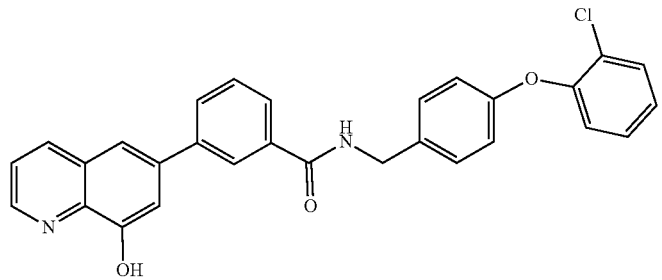

, and (SS15 or SS03158)

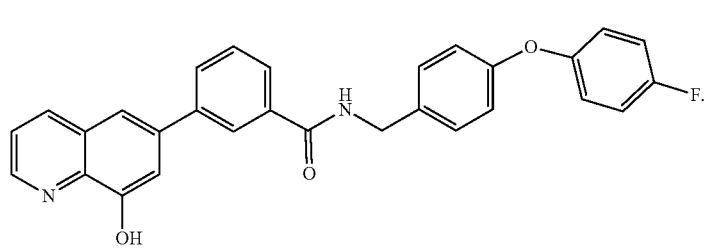

In other embodiments, the KDM4 inhibitor or pharmaceutically acceptable salt thereof includes the group of compounds wherein $R^1$ is

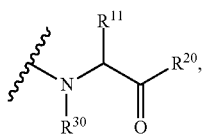

$R^{30}$ is hydrogen, $R^{11}$ is methyl, $R^{20}$ is $NR^{40}R^{41}$, $R^{40}$ is hydrogen, and $R^{41}$ is unsubstituted or substituted alkylaryl. Non-limiting examples of compounds in this group include the following:

(3009-3)

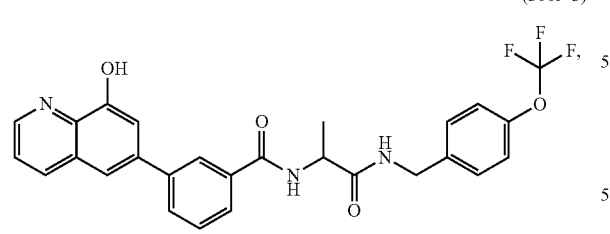

(3009-4)

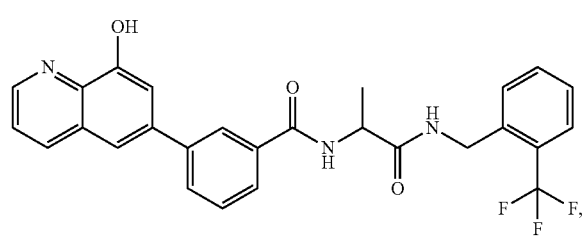

(3009-6)

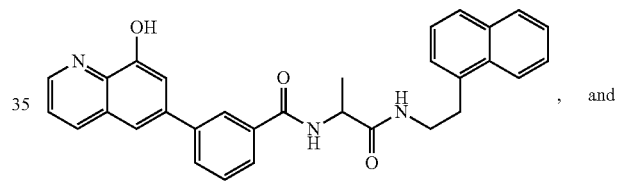

, and (3010-1)

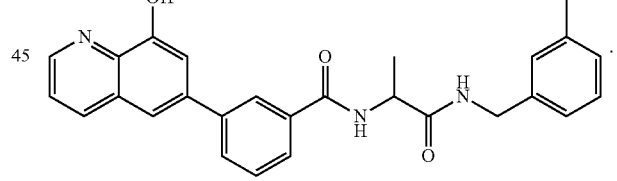

In other embodiments, the KDM4 inhibitor or pharmaceutically acceptable salt thereof includes the group of compounds wherein $R^1$ is

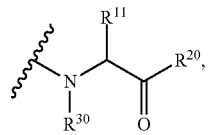

$R^{30}$ is hydrogen, $R^{20}$ is $NR^{40}R^{41}$, $R^{40}$ is hydrogen, $R^{41}$ is alkylaryl, and $R^{11}$ is alkylamide substituted with a cycloalkyl or aryl group. Non-limiting compounds in this group include the following:

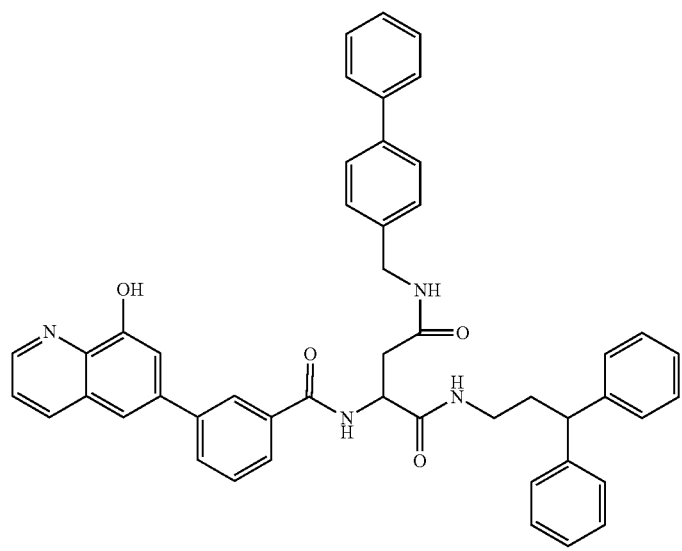
(3033-3)
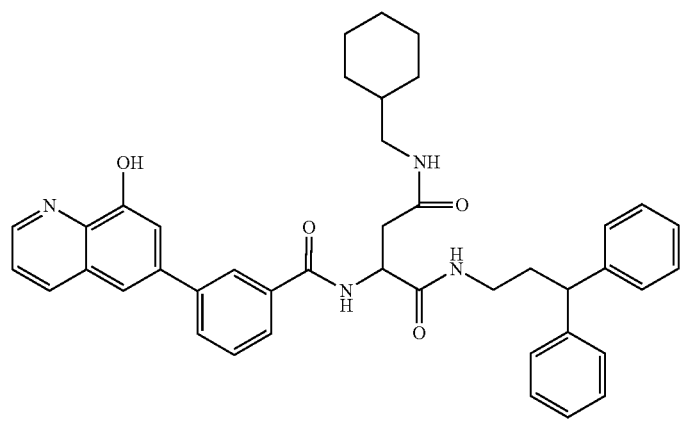
(3033-5)
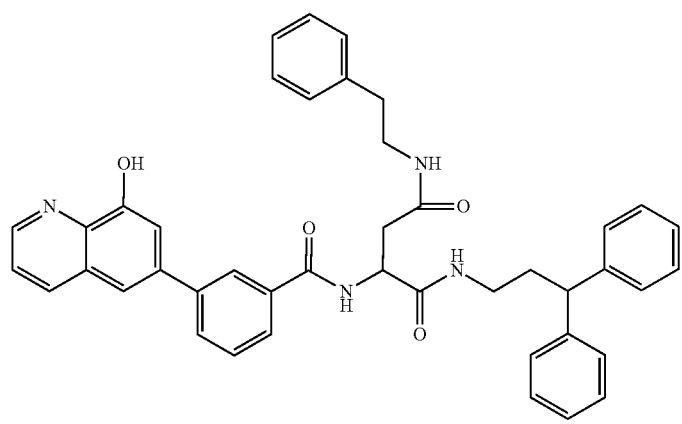
(3033-6)

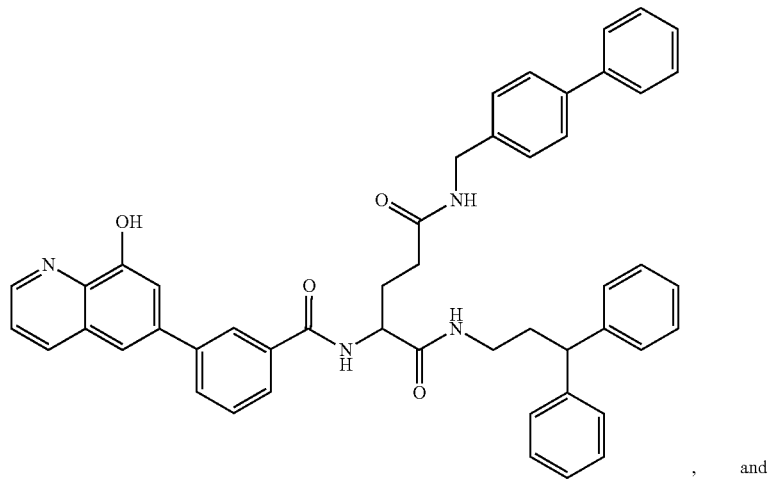
(3034-3)
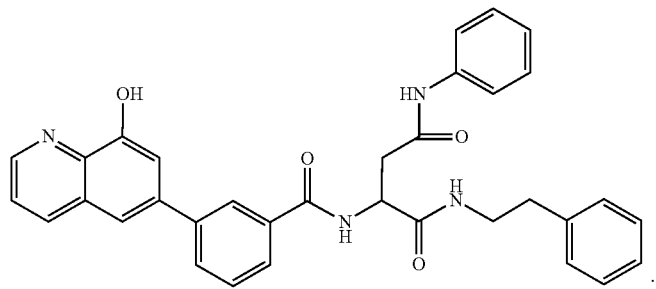
(3013-6)
In other embodiments, the KDM4 inhibitor or pharmaceutically acceptable salt thereof includes the group of compounds wherein $R^1$ is
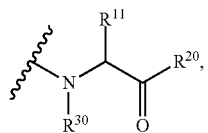
$R^{30}$ is hydrogen, $R^{11}$ is alkylheteroaryl, $R^{20}$ is $NR^{40}R^{41}$, $R^{40}$ is hydrogen, and $R^{41}$ is aryl or heteroaryl. Non-limiting examples of compounds in this group include the following:
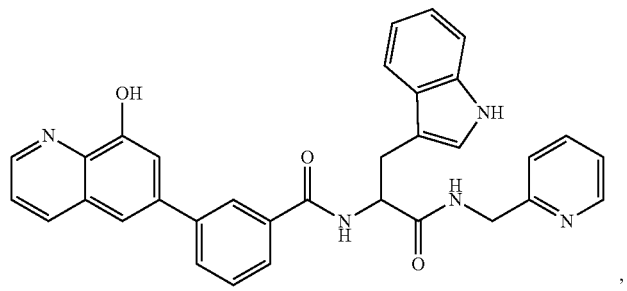
(3031-3)

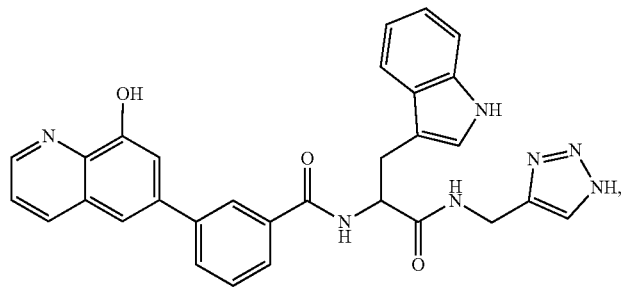
(3031-4)
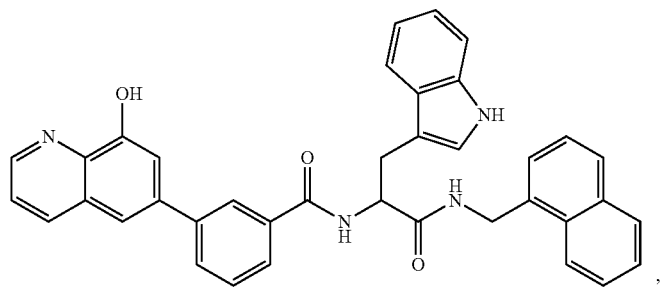
, and
(3031-5)
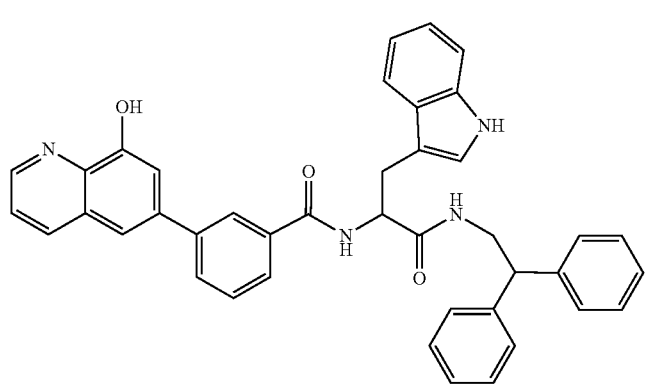
(3031-6)
In other embodiments, the KDM4 inhibitor or pharmaceutically acceptable salt thereof includes the group of compounds wherein $R^1$ is
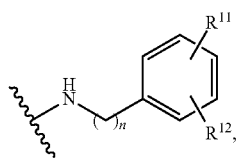
n is 0 or 1, $R^{11}$ is halogen, substituted or unsubstituted arylalkyl, ester, or $COR^{40}$, $R^{12}$ is hydrogen or halogen, and $R^{40}$ is aryl. Non-limiting examples of compounds in this group include the following:
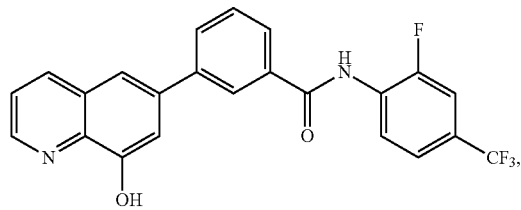
(oSS2)

-continued
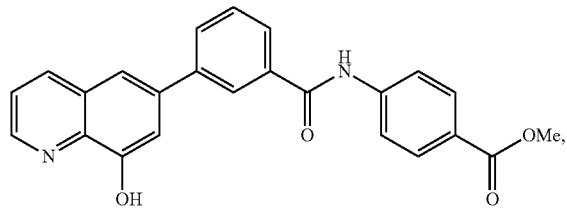
(oSS5 or SS02183)
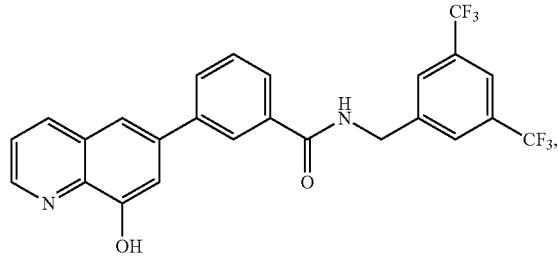
(oSS8 or SS02177)
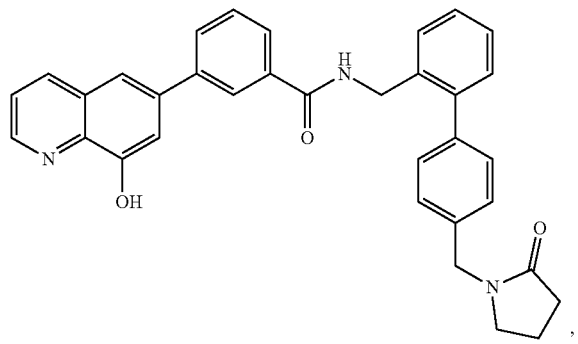
(oSS18 or SS03020)
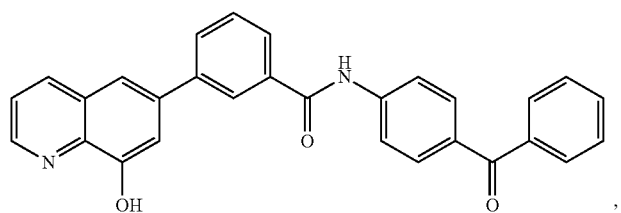
(oSS28)
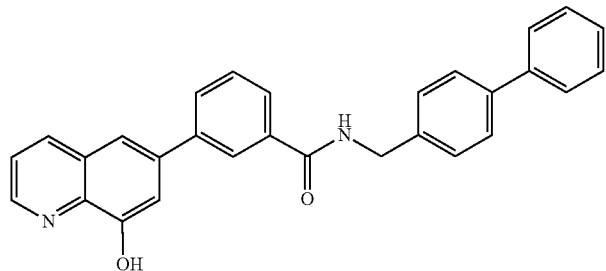
(SS72 or SS0286)
, and
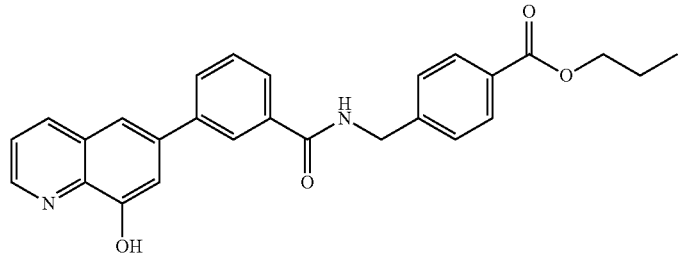
(SS67 or SS04111)
.

In other embodiments, the KDM4 inhibitor or pharmaceutically acceptable salt thereof includes the group of compounds wherein $R^1$ is

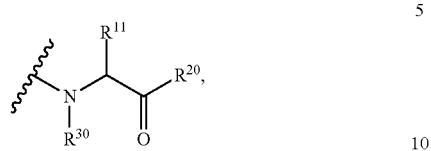

(5)

$R^{11}$ is alkyl, alkyl thioether, hydroxyl substituted alkyl aryl, hydroxyl substituted alkyl, or alkylheteroaryl, $R^{30}$ is hydrogen, $R^{20}$ is $NR^{40}R^{41}$, $R^{40}$ is hydrogen, and $R^{41}$ is alkylaryl optionally substituted with halogen or aryl. Non-limiting examples of compounds in this group include the following:

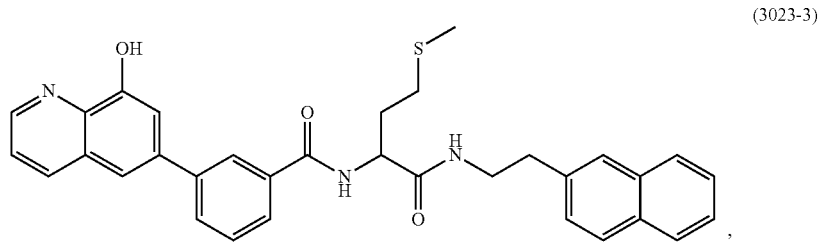

(3023-3)

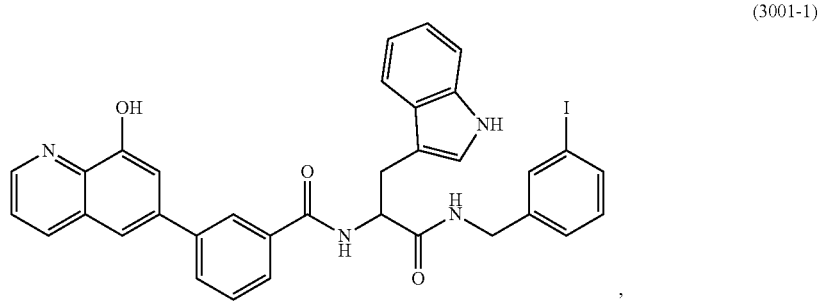

(3001-1)

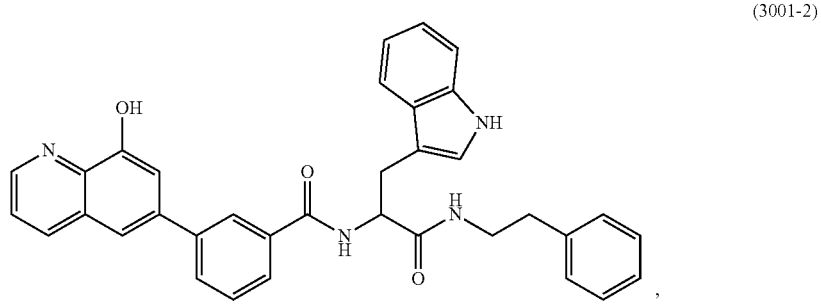

(3001-2)

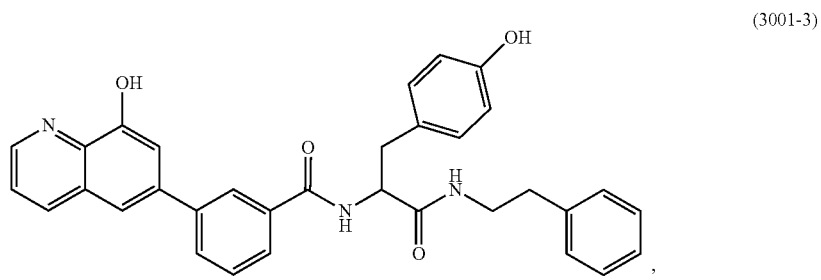

(3001-3)

-continued
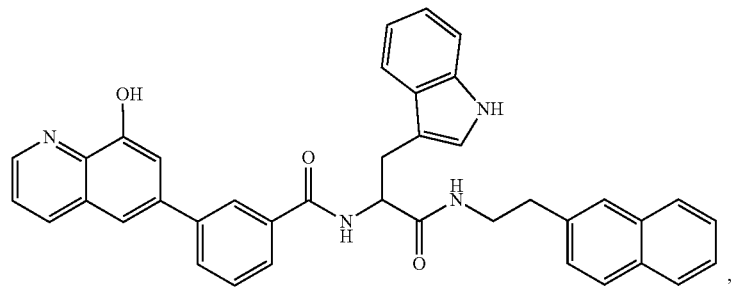
(3001-4)
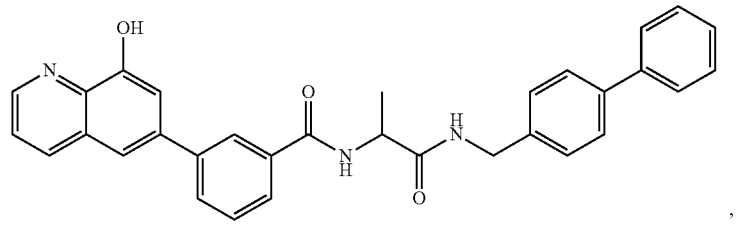
(3003-1)
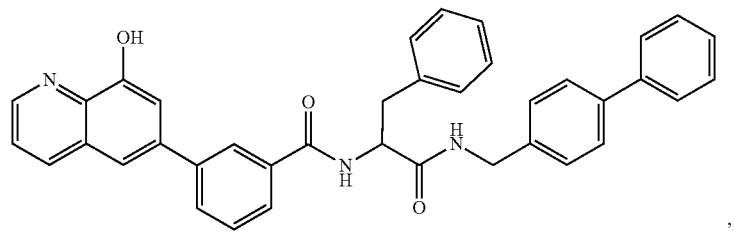
(3003-2)
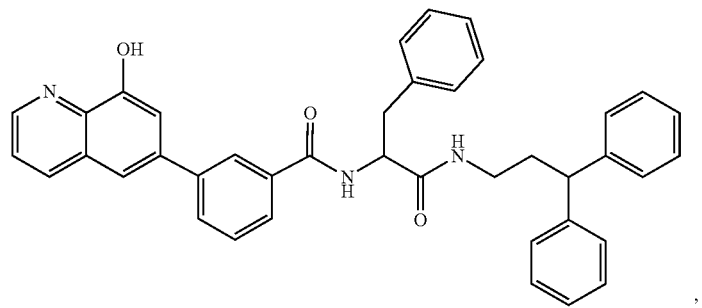
(3003-4)
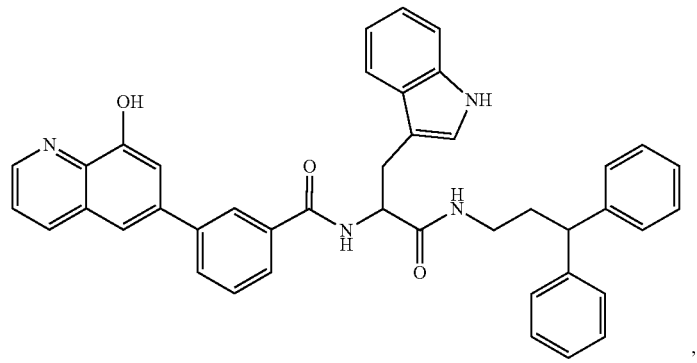
(3003-5)

(3029-4)
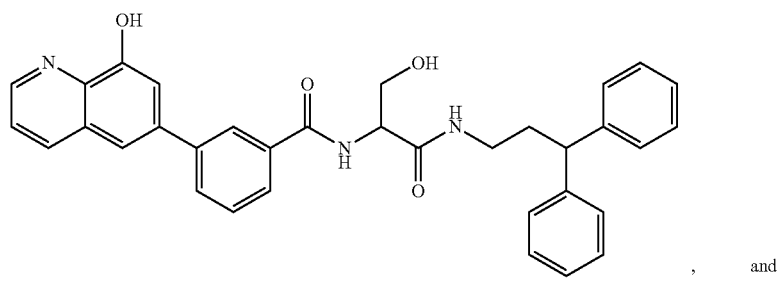
and
(3024-1)
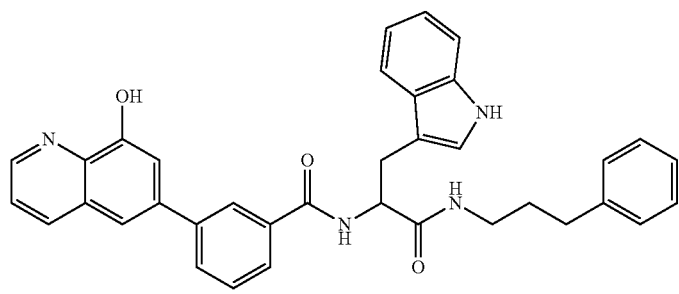
In other embodiments, the KDM4 inhibitor or pharmaceutically acceptable salt thereof includes the group of compounds wherein $R^1$ is
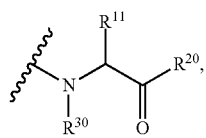
$R^{30}$ is hydrogen, $R^{11}$ is alkylaryl or alkylheteroaryl, $R^{20}$ is $NR^{40}R^{41}$, $R^{40}$ is hydrogen, and $R^{41}$ is alkyl aryl or aryl heterocycloalkyl. Non-limiting examples of compounds in this group include the following:
(3008-1 or D37)
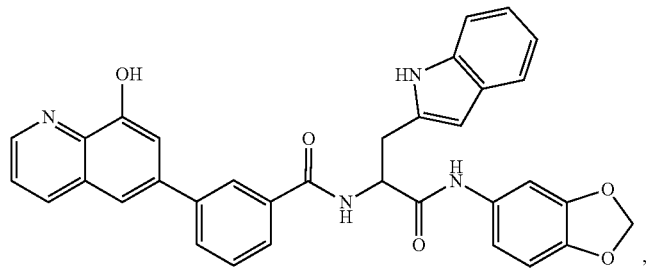

(3030-6)

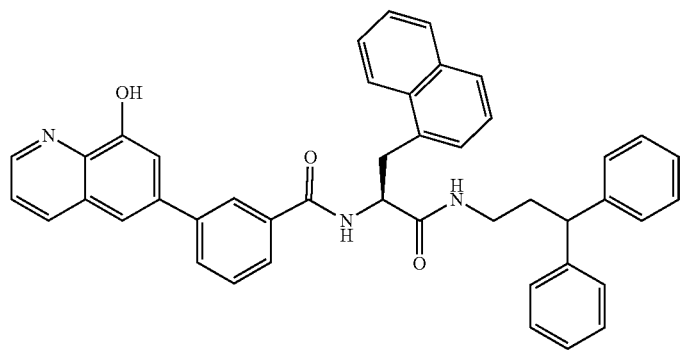

, and (3031-1)

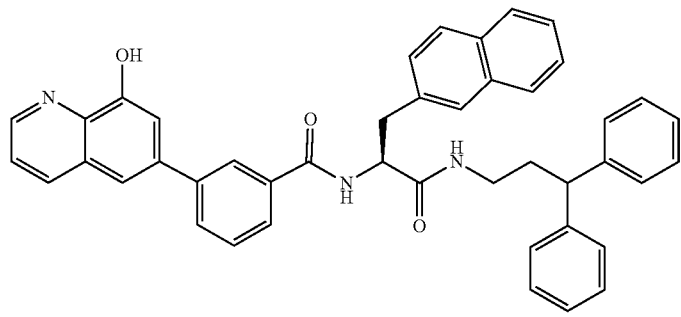

In other embodiments, the KDM4 inhibitor or pharmaceutically acceptable salt thereof includes the group of compounds wherein $R^1$ is

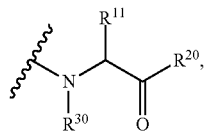

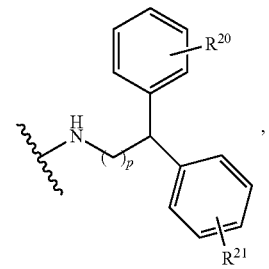

$R^{30}$ is hydrogen, $R^{11}$ is alkylaryl, $R^{20}$ is $NR^{40}R^{41}$, $R^{40}$ is hydrogen, and $R^{41}$ is alkyl substituted with a cycloalkyl group. Non-limiting examples of compounds in this group include the following:

p is 2, $R^{20}$ is halogen, and $R^{21}$ is alkyl substituted with halogen. Non-limiting examples of compounds in this group include the following:

(SS18)

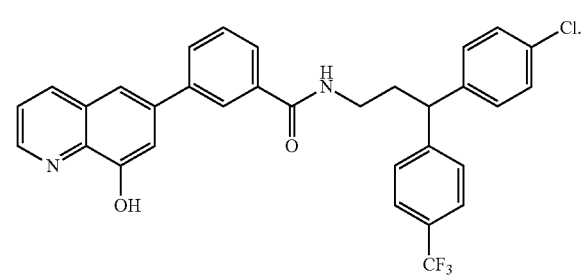

(3004-4)

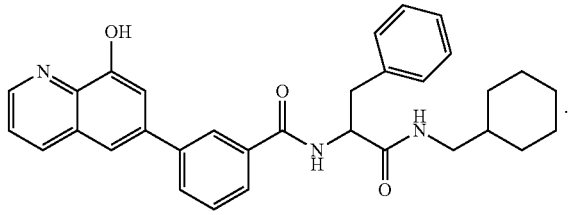

In other embodiments, the KDM4 inhibitor or pharmaceutically acceptable salt thereof includes the group of compounds wherein $R^1$ is Pharmaceutical Compositions In certain embodiments, the 8-hydroxyquinoline derivative compounds/inhibitors, or pharmaceutically acceptable salt thereof, as described herein is administered as a pure chemical. In other embodiments, the 8-hydroxyquinoline derivative compounds/inhibitors, or pharmaceutically acceptable salt thereof, as described herein, is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)), the disclosure of which is hereby incorporated herein by reference in its entirety.

Accordingly, provided herein is a pharmaceutical composition comprising at least one 8-hydroxyquinoline derivative compound/inhibitor, or a stereoisomer, pharmaceutically acceptable salt, hydrate, solvate, or N-oxide thereof, together with one or more pharmaceutically acceptable carriers. The carrier(s)(or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound SS27 (also named as oSS12, SS79, SS79N, SS81, or 171), or a pharmaceutically acceptable salt thereof.

In certain embodiments, the SS79 compound is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, Pa. (2005)).

The dose of the composition comprising at least one 8-hydroxyquinoline derivative compounds/inhibitors, or pharmaceutically acceptable salt thereof, as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids that can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelic methanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentaerythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example Eudragit® RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarbonylethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate); alcohols (propylene glycol, polyethylene glycol of various chain lengths), adipates (diethyladipate, di-(2-methoxy- or 2-ethoxyethyl)-adipate; benzophenone; diethyl- and dibutylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulfoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, trometamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik and angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine tetraacetic acid, nitrilotriacetic acid, diethylene triamine pentaacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In some embodiments, the pharmaceutical composition can be administered parenterally, e.g., intraperitoneally. In another embodiment, excipients useful for parenteral administration can be selected from α-cyclodextrins, β-cyclodextrins, γ-cyclodextrins, liposomes, surfactants, glycerol, polyethylene glycols, preservatives, water, ethanol, vegetable oils, saline solution, glucose solution, phosphate buffer, mannitol, normal serum albumin, sodium chloride solution, Ringer's dextrose, lactated Ringer's, fixed oils, chelating agents, and combinations thereof.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, in particular embodiments, the present disclosure provides a method of treating a disease regulated by histone methylation and/or demethylation in a subject in need thereof by modulating the activity of KDM4.

In an additional embodiment is a method for treating cancer in subject comprising administering a composition comprising at least one 8-hydroxyquinoline derivative compound/inhibitor, or a stereoisomer, pharmaceutically acceptable salt, hydrate, solvate, or N-oxide thereof, as described herein, together with one or more pharmaceutically acceptable carriers. In an additional embodiment is a method for inhibiting the growth of a tumor comprising administering a composition comprising a compound a compound SS27 (also named as oSS12, SS79, SS79N, SS81, 17l), or a pharmaceutically acceptable salt thereof.

In a further embodiment is the method for treating cancer in a subject wherein the cancer is selected from prostate cancer, kidney cancer, breast cancer, bladder cancer, lung cancer, or melanoma. In another embodiment, the compounds disclosed herein may be particularly useful In some embodiments, the kidney cancer can be human renal cell adenocarcinoma including metastatic or nonmetastatic renal cell adenocarcinoma, cancers caused by viruses such as, for example, human papillomavirus, metastatic and nonmetastatic prostate cancers including epithelial prostate cancers, and the like.

In some embodiments, the pharmaceutical compositions can be administered 1, 2, 3, or 4 times daily, or once per week, or once every other week, or at any other schedule wherein the compounds are effective and tolerated by the patient with few or no side effects. In some aspects, the pharmaceutical compositions are administered once daily for 72 hours, two weeks, or one month.

In one embodiment, an effective amount of pharmaceutical composition for the treatment of cancer is from about 10 mg of the disclosed compound to about 20 mg of the disclosed compound per kg of patient body weight, or is about 10, 11, 12, 13, 14, 15, 16, 17, 18, 19, or about 20 mg of the disclosed compound per kg of patient body weight, or a combination of any of the foregoing values, or a range encompassing any of the foregoing values.

In another embodiment, successful cancer treatment can include decreasing the volume of a tumor. Further in this embodiment, the tumor can have a volume of from about 5% less to about 50% less than the volume of the tumor before treatment, or of about 5, 10, 15, 20, 25, 30, 35, 40, 45, or about 50% less than the volume of the tumor before treatment, or a combination of any of the foregoing values, or a range encompassing any of the foregoing values. In an alternative embodiment, successful cancer treatment can include decreasing the rate of growth of a tumor. Further in this embodiment, the tumor after treatment can have a volume of at least about 50% less than an equivalent untreated tumor. Tumor volume can be measured by any means known in the art including, but not limited to, caliper measurements and volume calculation, ultrasonography measurements, magnetic resonance imaging (MRI), X-ray, computerized tomography (CT) scan, fluorescence imaging, bioluminescence imaging, positron emission tomography (PET), and any of these methods combined with the administration of an imaging enhancement or contrast agent such as, for example, iodine compounds, barium compounds, gadolinium, microbubbles, metabolites, or the like.

In other embodiments, the disclosed compounds and pharmaceutical compositions are effective inhibitors of cancer cell growth in cell culture including, but not limited to, ACHN (renal cell adenocarcinoma such as, for example, ATCC® CRL-1611™), 769-P (renal cell adenocarcinoma such as, for example, ATCC® CRL-1933™), 786-O (renal cell carcinoma such as, for example, ATCC® CRL-1932™), HK-2 (human papillomavirus 16 transformed kidney cells such as, for example, ATCC® CRL-2190™), VCaP (metastatic, castration-resistant prostate cancer such as, for example, ATCC® CRL-2876™), 22Rv1 (epithelial prostate carcinoma such as, for example, ATCC® CRL-2505™), PNT1A (normal human prostate epithelium immortalized with simian virus 40 (SV40)), another cancer or immortal cell line, or a combination thereof.

Other embodiments and uses will be apparent to one skilled in the art in light of the present disclosures. The following examples are provided merely as illustrative of various embodiments and shall not be construed to limit the invention in any way.

EXAMPLES

Example 1

Synthesis of Quinoline Derivatives/Analogs

All the quinoline derivatives were synthesized by using the synthetic strategy shown in scheme 1. First, 6-bromo- 8-methoxyquinoline (11) was synthesized via Skraup reaction of 4-bromo-2-methoxyaniline (10) with Glycerol in H₂SO₄. Suzuki coupling of 6-bromo-8-methoxyquinoline (11) with 3-Carboxyphenylboronic acid in EtOH:water (1:1) using Pd(PPh₃)₄ as catalyst afforded product 12 in 65% yield. Demethylation of 12 was done with 48% HBr (Aq.) under reflux conditions followed by coupling with different amines using EDC as coupling agent afforded 8-hydroxyquinoline derivatives 14α-d, 15α-x and 16α-k in 60-91% yields (Scheme 1, see also Tables 1 and 2 for R substituents).

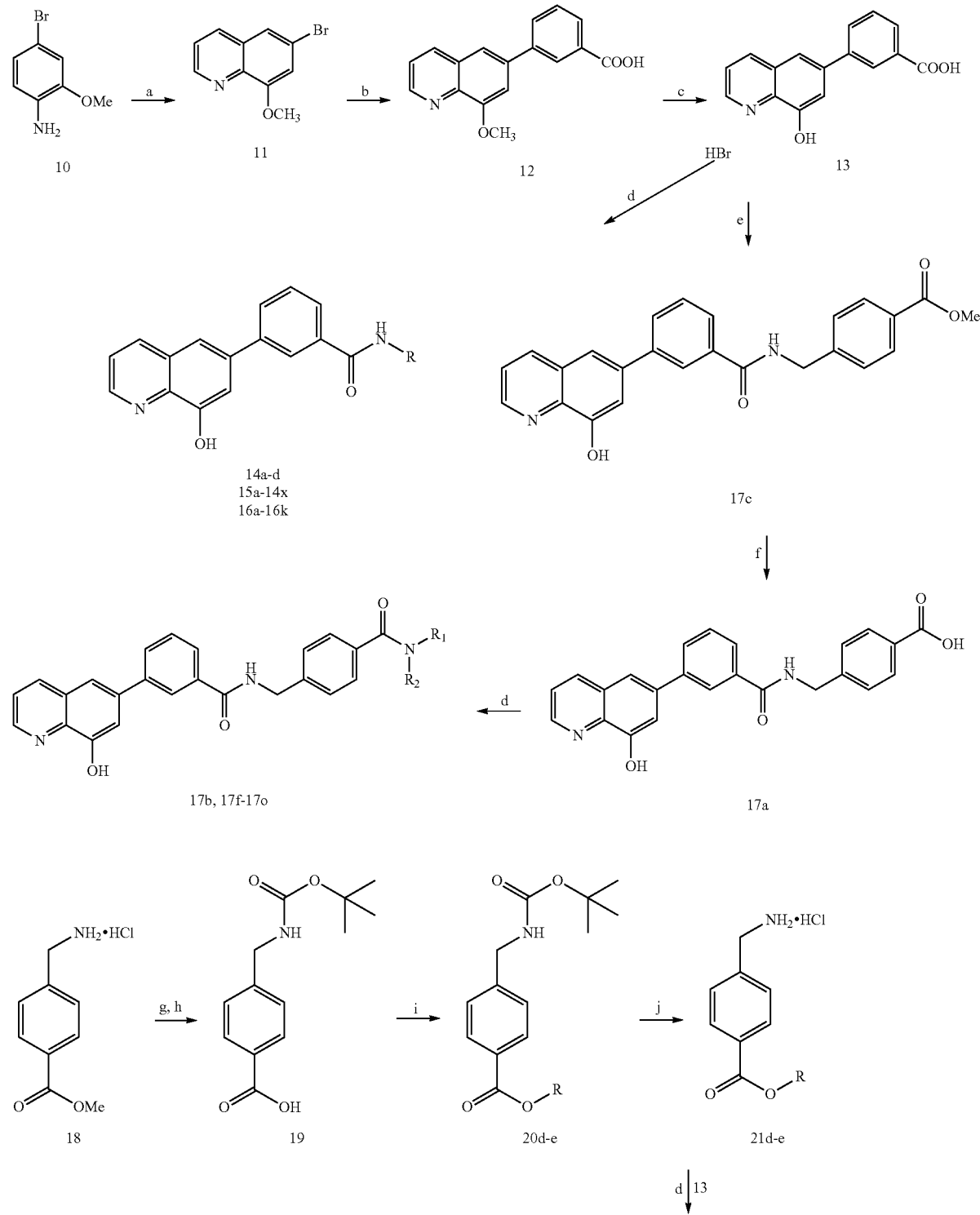

-continued

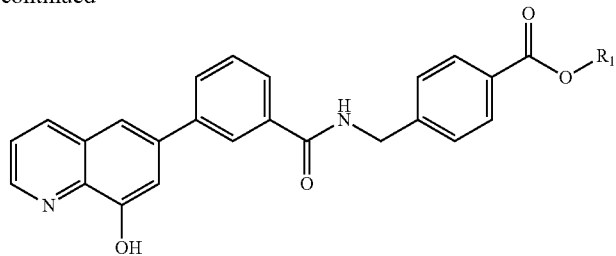

17d-e

Reaction conditions: a) Glycerol, Sodium 3-nitrobenzenesulfonate, water, H$_2$SO$_4$, 60-120° C., 71%; (b) 3-Carboxyphenylboronic acid, Pd(PPh$_3$)$_4$, EtOH: Water(3:1), Reflux, 65%; (c) HBr (48%), Reflux, 90%; (d) Amines (RNH$_2$), EDC, 6-Cl-HOBt, DIPEA, DMF, 50° C., 60-91%; e) Methyl 4-(aminomethyl)benzoate, EDC, 6-Cl-HOBt, DIPEA, DMF, 50° C., 81%; f) 10% (Aq.), THF: MeOH (1:1), rt; 87%; g) BOC$_2$O, TEA, THF, rt; h) 10% NaOH; i) RX, K$_2$CO$_3$, DMF, rt; j) 4N HCl-Dioxane, DCM, rt.

Compound 17c was synthesized by coupling of Methyl 4-(aminomethyl)benzoate with 13 using EDC as coupling agent. Compound 17c upon hydrolysis with Aq. NaOH gave acid 17a in 87% yield which upon coupling with different amines gave products 17b, and 17f-17o in quantitative yields (Scheme 1). Compounds 17d-17e were prepared from starting material methyl 4-(aminomethyl)benzoate hydrochloride (18) which upon BOC protection and hydrolysis gave product 19. Compound 19 when treated with different alkyl halides gave esters 20d-e which upon BOC deprotection with 4N HCl-dioxane have amines 21d-e. Coupling of amines 2d-e with 13 using EDC as coupling agent gave products 17d-e in good yields.

Example 2

Solid Phase Synthesis of Disclosed Quinoline Derivatives

Alternatively, the disclosed compounds can be prepared using a solid phase synthesis as described below. In carrying out a solid phase synthesis, it can be appreciated that without a protected hydroxyl group, double and triple coupled happened, but free hydroxyl is required for active compounds as shown below:

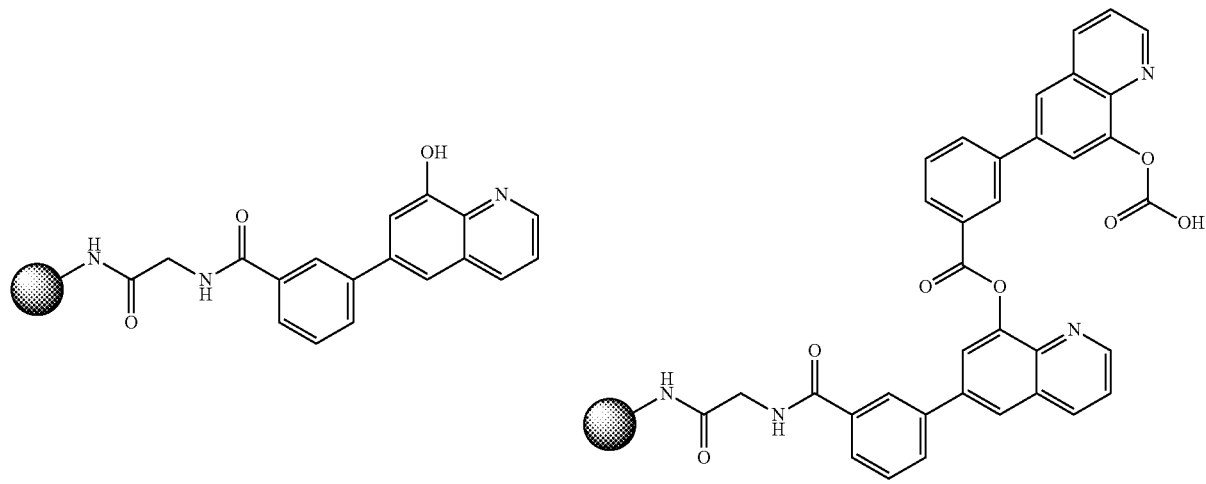

-continued

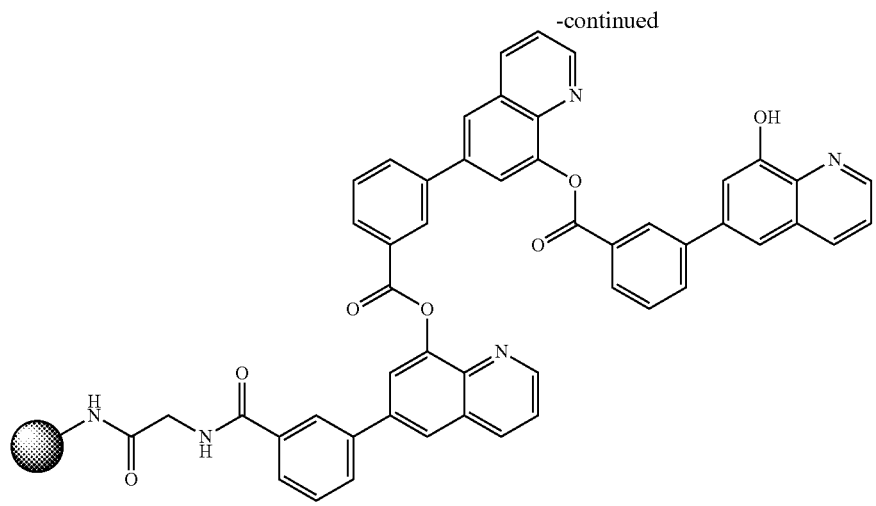

That is, if the hydroxyl group is not protected, carrying out the Suzuki reaction can be challenging as shown below.

Although the choice of protecting group can be varied depending upon various considerations, the MOM protecting group was found to be useful for the disclosed solid phase synthesis of the disclosed compounds.

For the solid phase synthesis approach, the precursor can be prepared as described below.

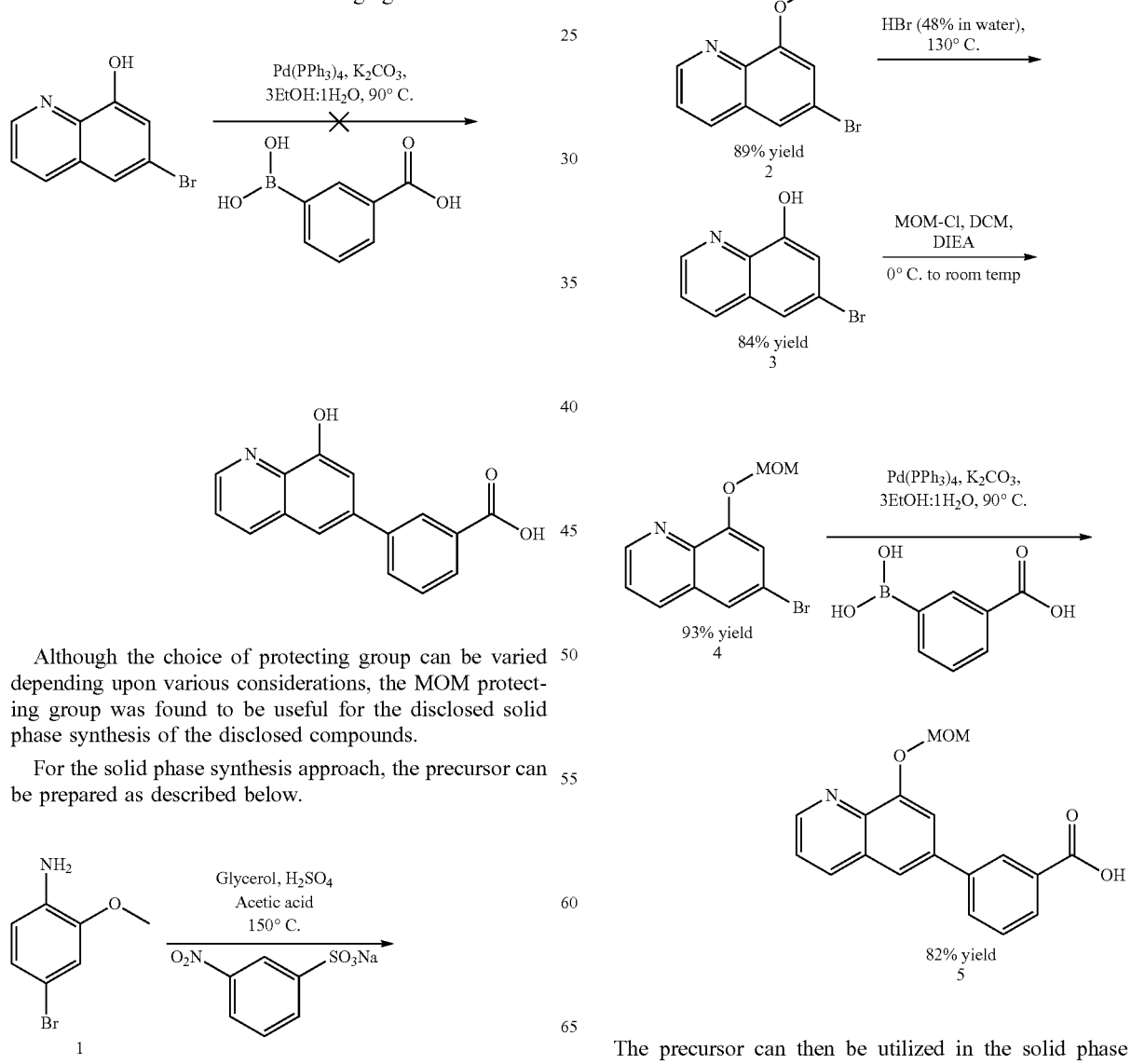

The precursor can then be utilized in the solid phase synthesis methods as shown below.

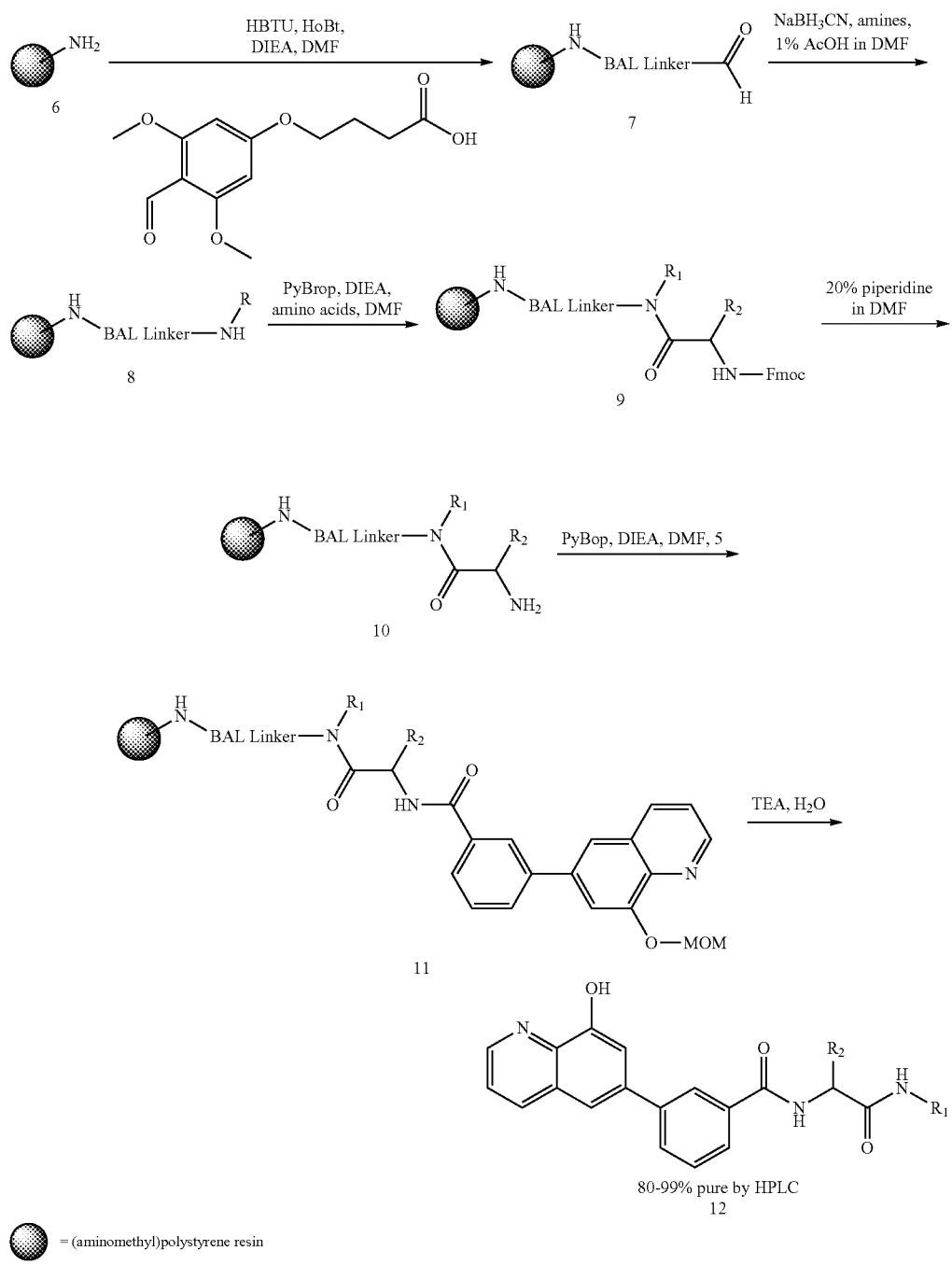

= (aminomethyl)polystyrene resin

Example 3

Effects of the Synthesized Quinoline Derivatives

All compounds were evaluated for their effects on LNCaP and 22rv1 cell lines at 1 and 0.5 μM concentrations, respectively. The initial interest was to see the importance of length of side chain on B-3. For this purpose different analogues of B-3 with chain length varying from 0 to 4 carbon were synthesized (Table 1). Increase in chain length from 3C to 4C resulted in deterioration of activity (compound 14a, Table 1). Decreasing the chain length from 3C to 2C also resulted in deterioration of activity (Compound 14b, Table 1) but decreasing the length further to 1C again resulted in restoration of activity (Compound 14c, Table 1). Compound 14d containing side chain with no carbon showed poor activity (Table 1). This initial study showed that B-3 analogues containing side chain of 1C and 3C showed better results over analogues with chain having 0C or 4C. In view of the availability of a variety of commercially available benzyl amines over phenyl propyl amines and method to functionalize analogues with 1C chain compound 14c was selected for further modification.

TABLE 1

Effect of length of side chain of B-3 on LnCap and 22rv1 cell lines.

Structure n = 0, 1, 2, 3, 4

| Compds. | Code | | % Cell Viability of LnCap cells at 1 μM | % Cell Viability of 22rv1 at 0.5 μM |
|---|---|---|---|---|
| B-3 | | n = 3 | 69.2% | 63.6% |
| 14a | SS04194 (SS-64) | n = 4 | ND | ND |
| 14b | SS04193 (SS-63) | n = 2 | ND | 83.7% (B-3, 63.6%) |
| 14c | SS04191 (SS-62) | n = 1 | ND | 79.3% (B-3, 63.6%) |
| 14d | SS04190 (SS-61) | n = 0 | ND | ND |

A series of derivatives of compound 14c were synthesized and evaluated for their effects on LnCap and 22rv1 cell lines. First, the effect of different electron donating and withdrawing substituents at various position of phenyl ring was evaluated (see Table 2).

TABLE 2

Effect of Synthesized Compounds 15a-15x, 16a-16k, and 17a-17o on LnCap and 22rv1 cell lines.

Structure

| Compds. | Code | R = | % Cell Viability of LnCap cells at 1 μM | % Cell Viability of 22rv1 at 0.5 μM |
|---|---|---|---|---|
| 15a | SS02084 | 4-F benzyl | 72.8 % (B-3, 69.2%) | ND |
| 15b | SS05131 | 3-F benzyl | ND | ND |
| 15c | SS05129 | 2-F benzyl | ND | ND |

TABLE 2-continued

Effect of Synthesized Compounds 15a-15x, 16a-16k, and 17a-17o on LnCap and 22rv1 cell lines.

Structure

R = [quinoline-phenyl-benzamide core with 8-OH quinoline, linked to phenyl, then C(=O)NH-R]

| Compds. | Code | R = | % Cell Viability of LnCap cells at 1 μM | % Cell Viability of 22rv1 at 0.5 μM |
|---|---|---|---|---|
| 15d | SS05185 | 4-hydroxybenzyl | ND | ND |
| 15e | SS02181 | 3-hydroxybenzyl | 87.9 (B-3, 14.3) | ND |
| 15f | SS02179 | 2-hydroxybenzyl | 56.9 (B-3, 14.3) | ND |
| 15g | SS02083 | 4-methoxybenzyl | 68.4% (B-3, 69.2%) | ND |
| 15h | SS02148 | 3-methoxybenzyl | 88.5% (B-3, ND) | ND |
| 15i | SS02146 | 2-methoxybenzyl | ND | ND |
| 15j | SS02075 | 2,4-dimethoxybenzyl | ND | ND |
| 15k | SS02140 | 3,4,5-trimethoxybenzyl | 98.1 (B-3, ND) | |

TABLE 2-continued

Effect of Synthesized Compounds 15a-15x, 16a-16k, and 17a-17o on LnCap and 22rv1 cell lines.

Structure R = [quinoline-OH core with biphenyl-carboxamide-NR substituent]

| Compds. | Code | R | % Cell Viability of LnCap cells at 1 µM | % Cell Viability of 22rv1 at 0.5 µM |
|---|---|---|---|---|
| 15l | SS02138 | 3,4-diOMe-benzyl | 75.7 (B-3, ND) | |
| 15m | SS02165 | 4-CF₃-benzyl | 67.7% (B-3, 67.8) | ND |
| 15n | SS02159 | 3-CF₃-benzyl | 75.4% (B-3, 67.8%) | ND |
| 15o | SS02161 | 2-CF₃-benzyl | 94.5 (B-3, 67.8) | ND |
| 15p | SS02177 | 3,5-diCF₃-benzyl | 62.5 (B-3, 67.8) | ND |
| 15q | SS04159 | 4-F, 2-CF₃-benzyl | ND | ND |
| 15r | SS02163 | 4-CF₃, 2-F-benzyl | 101 (B-3, 67.8) | ND |
| 15s | SS02106 | 4-CN-benzyl | 52.8% (B-3, ND) | |

TABLE 2-continued

Effect of Synthesized Compounds 15a-15x, 16a-16k, and 17a-17o on LnCap and 22rv1 cell lines.

Structure

R =

| Compds. | Code | R = | % Cell Viability of LnCap cells at 1 µM | % Cell Viability of 22rv1 at 0.5 µM |
|---|---|---|---|---|
| 15t | SS02095 | 4-(dimethylamino)benzyl | 66.3% (B-3, 69.2%) | 19.6% (B-3, 63.6%) |
| 15u | SS02085 | 4-pyridylmethyl | 70.9 (B-3, 69.2) | ND |
| 15v | SS02074 | 2-thienylmethyl | 79.8% (B-3, 71.9%) | ND |
| 15w | SS02087 | cyclopropylmethyl | 60.7% (B-3, 71.9%) | ND |
| 15x | SS02097 | cyclohexylmethyl | 104% (B-3, ND) | ND |
| 16a | SS03152 | 4-phenoxybenzyl | ND | 29.5% (B-3, 42.5%) at 1 µM |
| 16b | SS03154 | 4-(4-chlorophenoxy)benzyl | ND | 33.2% (B-3, 42.5%) at 1 µM |
| 16c | SS03156 | 4-(2-chlorophenoxy)benzyl | ND | 38.1% (B-3, 42.5%) at 1 µM |
| 16d | SS03158 | 4-(4-fluorophenoxy)benzyl | ND | 35.1% (B-3, 42.5%) at 1 µM |

TABLE 2-continued

Effect of Synthesized Compounds 15a-15x, 16a-16k, and 17a-17o on LnCap and 22rv1 cell lines.

Structure

R =

[Structure: 8-hydroxyquinoline-6-yl linked to benzamide with N-R group]

| Compds. | Code | Structure | % Cell Viability of LnCap cells at 1 μM | % Cell Viability of 22rv1 at 0.5 μM |
|---|---|---|---|---|
| 16e | SS02086 | [biphenyl-CH2-] | 48.3% (B-3, 71.9%) | 9.2% (B-3, 63.6%) |
| 16f | SS03018 | [4'-CF3-biphenyl-CH2-] | 44.2% (B-3, 14.3%) | ND |
| 16g | SS03026 | [4-(2-methyl-2,3-dihydrobenzofuran-6-yl)phenyl-CH2-] | 30.0% (B-3, 14.3%) | ND |
| 16h | SS03022 | [3-phenyl-phenyl-CH2-] | 21.8% (B-3, 14.3%) | 26.9 % (B-3, 63.6%) |
| 16i | SS03028 | [3-(4-fluorophenyl)phenyl-CH2-] | 17.3% (B-3, 14.3%) | 42.01 (B-3, 63.6%) |
| 16j | SS03020 | [2-(4-(2-oxopyrrolidin-1-ylmethyl)phenyl)phenyl-CH2-] | 10.9% (B-3, 14.3) % | 14.3 (B-3, 63.6%) |

TABLE 2-continued

Effect of Synthesized Compounds 15a-15x, 16a-16k, and 17a-17o on LnCap and 22rv1 cell lines.

Structure

R = [quinoline-benzamide core structure with OH group]

| Compds. | Code | R = | % Cell Viability of LnCap cells at 1 μM | % Cell Viability of 22rv1 at 0.5 μM |
|---|---|---|---|---|
| 16k | SS02132 (SS-74) | [4-(phenylcarbonyl)phenyl] | 26.7 (B-3, ND) | 6.4% (B-3, 63.6%) |
| 17a | SS02191 | [4-carboxyphenyl] | 97.5 (B-3, 67.8) | ND |
| 17b | SS04141 | [4-carbamoylphenyl] | ND | 78.4% (B-3, 63.6%) |
| 17c | SS02183 (SS04087) | [4-(methoxycarbonyl)phenyl] | 47.9% (B-3, 67.8%) | 12.9% (B-3, 63.6%) |
| 17d | SS04109 | [4-(ethoxycarbonyl)phenyl] | ND | 22.7% (B-3, 63.6%) |
| 17e | SS04111 (SS-67) | [4-(propoxycarbonyl)phenyl] | ND | 7.9% (B-3, 63.6%) |
| 17f | SS-58 SS05039 | [4-(isobutylcarbamoyl)phenyl] | ND | 41.0% (B-3, 63.6%) |

TABLE 2-continued

Effect of Synthesized Compounds 15a-15x, 16a-16k, and 17a-17o on LnCap and 22rv1 cell lines.

Structure

R = [quinoline-phenyl-C(=O)NH-R core structure with OH on quinoline]

| Compds. | Code | R = | % Cell Viability of LnCap cells at 1 μM | % Cell Viability of 22rv1 at 0.5 μM |
|---|---|---|---|---|
| 17g | SS-59 SS05041 | [4-(isopropylcarbamoyl)benzyl] | ND | 41.0% (B-3, 63.6%) |
| 17h | SS05187 | [4-(cyclobutylcarbamoyl)benzyl] | ND | ND |
| 17i | SS04125 (SS-39) | [4-(cyclopentylcarbamoyl)benzyl] | ND | 29.8% (B-3, 63.6%) |
| 17j | SS04105 (SS-33) | [4-(cyclohexylcarbamoyl)benzyl] | ND | 5.0% (B-3, 63.6%) |
| 17k | SS05053 (SS-40) | [4-(cycloheptylcarbamoyl)benzyl] | ND | 10.8% (B-3, 63.6%) |
| 17l | SS02208 (SS-12) | [4-((4-(trifluoromethyl)cyclohexyl)carbamoyl)benzyl] | 24.2% (B-3, 14.3%) | |
| 17m | SS05111, SS05173 (SS-81) | [4-((trans-4-(trifluoromethyl)cyclohexyl)carbamoyl)benzyl] | 24.2% (B-3, 14.3%) | |

TABLE 2-continued

Effect of Synthesized Compounds 15a-15x, 16a-16k, and 17a-17o on LnCap and 22rv1 cell lines.

| Compds. | Code | Structure R = | % Cell Viability of LnCap cells at 1 µM | % Cell Viability of 22rv1 at 0.5 µM |
|---|---|---|---|---|
| 17n | SS05109 | | | |
| 17o | SS05119 | | | |

Thus, from the SAR study, compounds 16j and 17l emerged as lead compounds and were selected for further studies of their activity and selectivity against KDM4 enzymes.

In general, compounds containing electron withdrawing groups like $CF_3$ showed better activities over compounds containing electron donating groups such as OMe and OH. Compounds containing functional groups at the para position of the phenyl ring showed better activities over compounds with same functional groups at the ortho and meta positions. Some di- and tri-substituted derivatives were also synthesized and all showed a good to moderate range of activities. Replacement of the benzene ring with heterocyclic rings such as pyridine and thiophene was fruitful (see compounds 15u-15v). Further, replacing aromatic rings with aliphatic rings such as cyclohexyl and cyclopropyl did not result in improvement of activity (compounds 15w-15x).

Next, some hydrophobic and bulky substituents were placed at the para position to assess toleration versus smaller functional groups. Compound 16a with a phenoxy group at the para position displayed significant improvement of activity over B-3. Any further functionalization on the phenoxy group was not well-tolerated as evident from the activities of compounds 16b-16d. Removal of the oxygen from compound 16a also resulted in restoration of activity (compound 16e). Any substitution on biphenyl ring did not give better results than compound 16e except compound 16j which inhibited 22rv1 cells much better than B-3.

Interestingly, replacing oxygen of compound 16a with carbonyl compounds showed significant improvement in activity (compound 16e). From this results it appeared that a carbonyl group at $4^{th}$ position of benzyl amine may have significant role; therefore some ester and amide based compounds containing carbonyl group at the $4^{th}$ position of benzyl group were synthesized. Compounds 17a and 17b containing a free carboxylic acid and primary amide, respectively showed lower activity than B-3 against 22rv1 and Lncap cell lines. Interestingly, the methyl ester of compound 17a greatly increased the potency which may be due to its prodrug nature (compound 17c). Changing methyl to ethyl ester resulted in deterioration of activity but an increase of activity was observed with the propyl ester. In fact the activity with propyl ester was better than compound 17c containing methyl ester (compound 17e). On the other hand, converting the acid group of 17a to amides also proved useful as evident from the activities of compounds 17f and 17g containing isobutyl and isopropyl groups, respectively. Synthesizing an amide of 17a with a cyclohexyl amine showed significant jump in activity compared to B-3 (compound 17j. Decreasing the ring size to butyl or pentyl or increasing to heptyl resulted in loss of activity (compounds 17i and 17k).

Activity of 17a improved further on placing a $CF_3$ group at the $4^{th}$ position (compound 17l). The absolute configuration of reactant 4-trifluoromethylcyclohexyl amine used in the preparation of compound 17l was not specified by the vendor, and the absolute configuration of the isolated compound 17l was not experimentally determined. In order to see if absolute configuration of 4-(trifluoromethyl)cyclohexylamine have any role on activity of compound 17l cis and trans isomers 4-(trifluoromethyl)cyclohexylamine were purchased and compound 17m and 17n were synthesized, respectively. Interestingly 17m (trans isomer) was much more active than compound 17n (cis isomer). The NMR spectra and activities of compound 17m and 17l were similar indicating the trans configuration compound 17l as well. Furthermore, the compound 17o in which the cyclohexyl ring was replaced by an aromatic ring was synthesized. Compound 17o showed significantly lower activities compared to compounds 17l and 17m.

In some aspects, the SAR studies suggest that compounds 16j and 17l are potential lead compounds based on their activity and selectivity against KDM4 enzymes.

Example 4

In Vitro Studies of the Synthesized Quinoline Derivatives

Relative cell growth can be assessed using the MTT (3-(4,5-dimethylthiazol-2-yl)-2,5-diphenyltetrazolium bromide) assay, a colorimetric assay for assessing cell metabolic activity. Cells (1000 to 2000 cells/well) in 150 µL culture medium were seeded in wells of a 96-well plate one day before various concentrations of drugs were added. After continuing culture in the presence of the drugs for the indicated time (3-4 days), 20 µL of 5 mg/mL MTT solution (Sigma-Aldrich) was added into each well. After incubation at 37° C. for 30 min, the culture medium was removed and 100 µL of DMSO was added to dissolve MTT crystals. Plates were shaken for 15 min at room temperature and absorbance at $OD_{590}$ was read by plate reader. Results of MTT assays for compounds disclosed herein can be found in FIGS. 1, 2A-2C, 3, 4, 5, 6, 7, 8, 9, 10A-10C, and 11A-11C.

Example 5

In Vivo Studies of the Synthesized Quinoline Derivatives

Figure 12A:
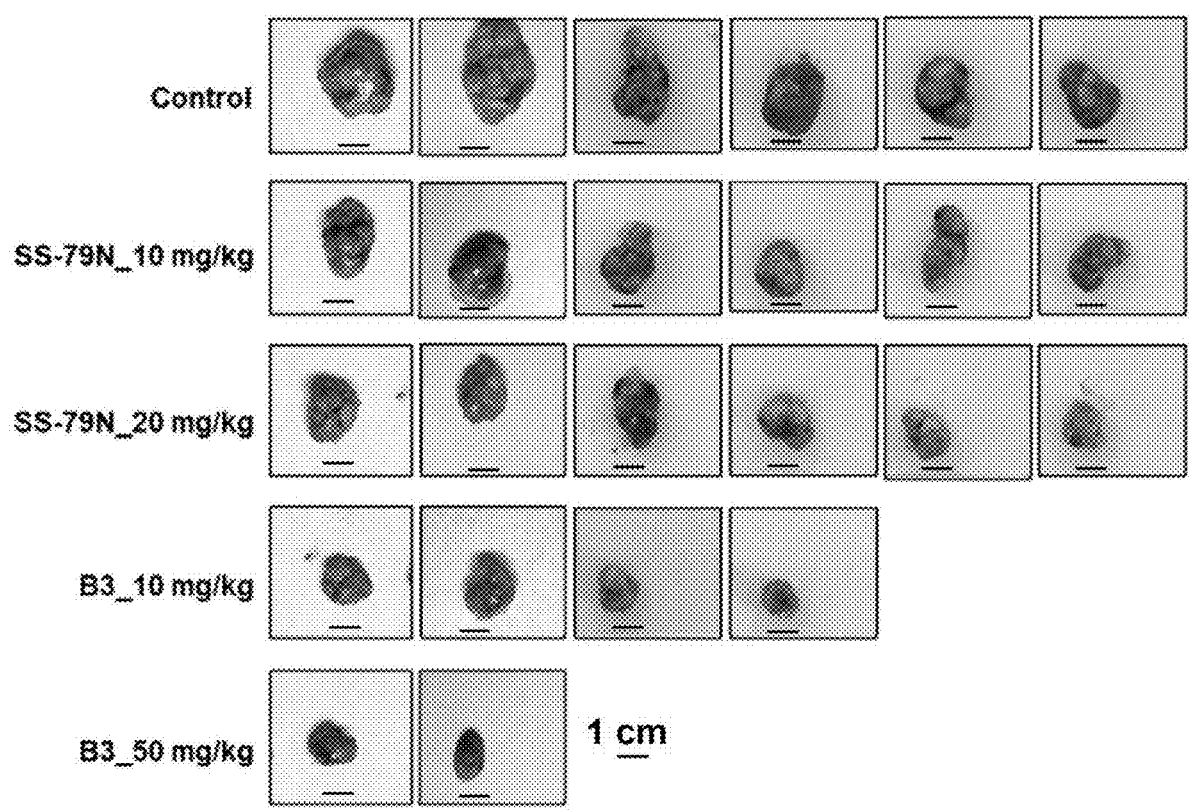
FIGS. 12A-12B show tumor size change (castration resistant prostate cancer cell line 22RV1 in mice) for DMSO controls, compound SS-79N disclosed herein, and B3 (a previously disclosed 8-hydroxyquinoline-containing compound).
Figure 12B:
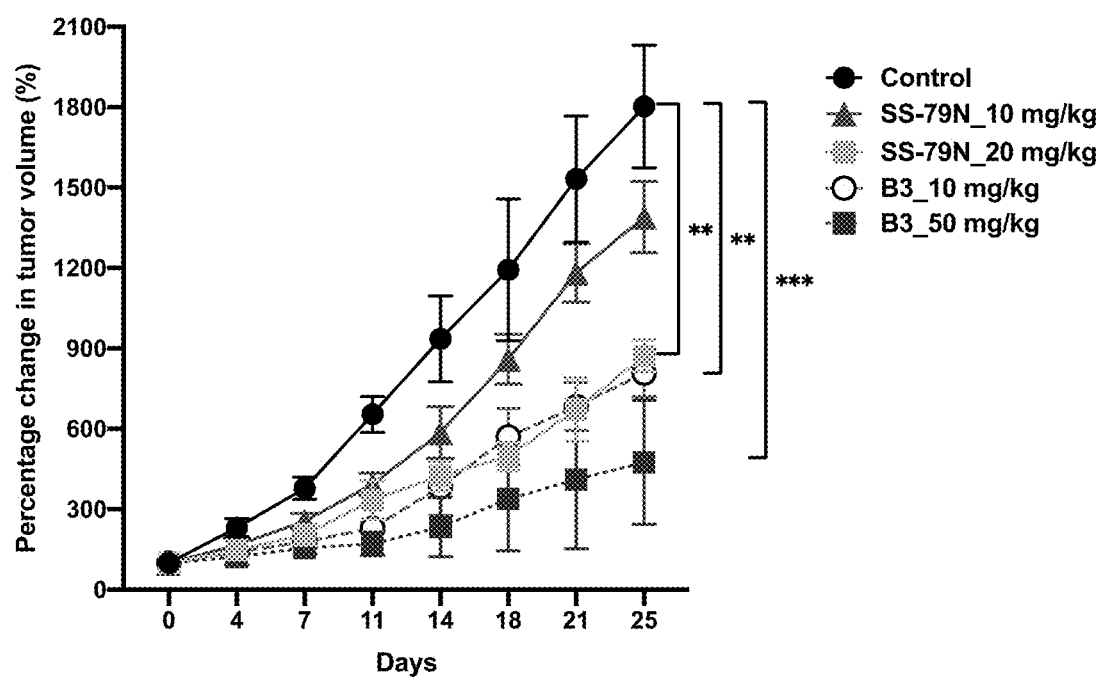

All animal work was approved by the Institutional Animal Care and Use Committee. NOD/SCID mice (6-8 weeks old) were subcutaneously injected in the flank region with castration resistant prostate cancer cell line 22RV1 ($1 \times 10^6$ cells/site) mixed with 50% Matrigel (BD Biosciences). When tumor volumes reached 50-100 mm$^3$ in size, animals were randomly divided into 5 groups: control (DMSO); B3 (50 or 10 mg/kg in DMSO); SS-79N (20 or 10 mg/kg in DMSO). Each group included six mice. Tumor volume (cubic millimeters) was measured by caliper twice a week and calculated by using the ellipsoid formula ($\pi/6 \times$length$\times$width$\times$depth, see FIGS. 12A-12B).

REFERENCES 1)(a) Fukagawa, T. Critical histone post-translational modifications for centromere function and propagation. *Cell Cycle*, 2017, 16, 1259-1265; (b) Nadal, S.; Raj, R.; Mohammed, S.; Davis, B. G. Synthetic post-translational modification of histones. *Current Opinion in Chemical Biology*, 2018, 45, 35-47.
2) Lin, H.; Li, Q.; Li, Q.; Zhu, J.; Gu, K.; Jiang, X.; Hu, Q.; Feng, F.; Qu, W.; Chen, Y.; Sun, H. Small molecule KDM4s inhibitors as anti-cancer agents. *J. Enzyme Inhib. Med. Chem.* 2018, 33,777-793.
3) Kaniskan, H. Ü.; Martini, M. L.; Jin, J. Inhibitors of Protein Methyltransferases and Demethylases. *Chem. Rev.*, 2018, 118, 989-1068.
4) Binda, C.; Valente, S.; Romanenghi, M.; Pilotto, S.; Cirilli, R.; Karytinos, A.; Ciossani, G.; Botrugno, O. A.; Forneris, F.; Tardugno, M.; Edmondson, D. E.; Minucci, S.; Mattevi, A.; Ma, A. Biochemical, Structural, and Biological Evaluation of Tranylcypromine Derivatives as Inhibitors of Histone Demethylases LSD1 and LSD2. *J. Am. Chem. Soc.* 2010, 132, 6827-6833.
5) Markolovic, S.; Leissing, T. M.; Chowdhury, R.; Wilkins, S. E.; Lu, X.; Schofield, C. J. Structure-Function Relationships of Human JmjC Oxygenases-Demethylases versus Hydroxylases. *Curr. Opin. Struct. Biol.* 2016, 41, 62-72.
6)(a) Guerra-Calderas, L.; González-Barrios, R.; Herrera, L. A.; de León, D. C.; Soto-Reyes, E. The role of the histone demethylase KDM4A in cancer. *Cancer Genet* 2015, 208, 215-224; (b) Berry, W. L.; Janknecht, R. KDM4/JMJD2 histone demethylases: epigenetic regulators in cancer cells. *Cancer Res* 2013; 73, 2936-42.
7)(a) Chu, C. H.; Wang, L. Y.; Hsu, K. C.; Chen, C. C.; Cheng, H. H.; Wang, S. M.; Wu, C. M.; Chen, T. J.; Li, L. T.; Liu, R.; Hung, C. L.; Yang, J. M.; Kung, H. J.; Wang, W. C. KDM4B as a target for prostate cancer: structural analysis and selective inhibition by a novel inhibitor. *J. Med. Chem.* 2014, 57, 5975-5985; (b) Kawazu, M.; Saso, K.; Tong, K. I.; McQuire, T.; Goto, K.; Son, D. O.; Wakeham, A.; Miyagishi, M.; Mak, T. W. Hitoshi Okada Histone demethylase JMJD2B functions as a co-factor of estrogen receptor in breast cancer proliferation and mammary gland development. *PLoS One* 2011, 6, e17830; (c) Berry, W. L.; Shin, S.; Lightfoot, S. A.; Janknecht, R. Oncogenic features of the JMJD2A histone demethylase in breast cancer. *Int. J. Oncol.* 2012, 41, 1701-1706.
8)(a) King, O. N. F.; Li, X. S.; Sakurai, M.; Kawamura, A.; Rose, N. R.; Ng, S. S.; Quinn, A. M.; Rai, G.; Mott, B. T.; Beswick, P.; Klose, R. J.; Oppermann, U.; Jadhav, A.; Heightman, T. D.; Maloney, D. J.; Schofield, C. J.; Simeonov, A. Quantitative high-throughput screening identifies 8-hydroxyquinolines as cell-active histone demethylase inhibitors. *PLoS One* 2010, 5, e15535; (b) Hopkinson, R. J.; Tumber A, Yapp C, et al. 5-Carboxy-8-hydroxyquinoline is a broad spectrum 2-oxoglutarate oxygenase inhibitor which causes iron translocation. *Chem. Sci.* 2013, 4, 3110-3117; (c) Schiller, R.; Scozzafava, G.; Tumber, A.; Wickens, J. R.; Bush, J. T.; Rai, G.; Lejeune, C.; Choi, H.; Yeh, T. L.; Chan, M. C.; Mott, B. T.; McCullagh, J. S. O.; Maloney, D. J.; Schofield, C. J.; Kawamura, A. A cell-permeable ester derivative of the JmjC histone demethylase inhibitor IOX1. *ChemMedChem.* 2014, 9, 566-71; (d) Carter, D. M.; Specker, E.; Przygodda, J.; Neuenschwander, M.; von Kries, J. P.; Heinemann, U.; Nazaré, M.; Gohlke, U. Identification of a novel benzimidazole pyrazolone scaffold that inhibits KDM4 lysine demethylases and reduces proliferation of prostate cancer cells. SLAS Discov 2017, 22, 801-12; (e) Thalhammer, A.; Mecinović, J.; Loenarz, C.; Tumber, A.; Rose, N. R.; Heightman, T. D.; Schofield, C. J. Inhibition of the histone demethylase JMJD2E by 3-substituted pyridine 2,4-dicarboxylates. *Org. Biomol. Chem.* 2011, 9, 127-35; (f) Wang, L.; Chang, J.; Varghese, D.; Dellinger, M.; Kumar, S.; Best, A. M.; Ruiz, J.; Bruick, R.; Peña-Llopis, S.; Xu, J.; Babinski, D. J.; Frantz, D. E.; Brekken, R. A. Quinn, A. M.; Simeonov, A.; Easmon, J.; Martinez, E. D. A small molecule modulates Jumonji histone demethylase activity and selectively inhibits cancer growth. *Nat. Commun.* 2013, 4, 2035; (g) Roatsch, M.; Robaa, D.; Pippel, M.; Nettleship, J. E.; Reddivari, Y.; Bird, L. E.; Hoffmann, I.; Franz, H.; Owens, R. J.; Schüe, R.; Flaig, R.; Sippl, W.; Jung, M. Substituted 2-(2-aminopyrimidin-4-yl)pyridine-4-carboxylates as potent inhibitors of JumonjiC domain-containing histone demethylases. *Future Med. Chem.* 2016, 8, 1553-1571; (h) England, K. S.; Tumber, A.; Krojer, T.; Scozzafava, G.; Ng, S. S.; Daniel, M.; Szykowska, A.; Che, K.; Delft, F. v.; Burgess-Brown, N. A.; Kawamura, A.; Schofield, C. J.; Brennan, P. E. Optimisation of a triazolopyridine based histone demethylase inhibitor yields a potent and selective KDM2A (FBXL11) inhibitor. Medchemcomm 2014, 5, 1879-86; (i) Bavetsias, V.; Lanigan, R. M.; Ruda, G. F et al. 8-Substituted pyrido[3,4-d]pyrimidin-4(3H)-one derivatives as potent, cell permeable, KDM4 (JMJD2) and KDM5 (JARID1) histone lysine demethylase inhibitors. J. Med. Chem. 2016, 59, 1388-1409; (j) Westaway, S. M.; Preston, A. G.; Barker, M. D et al. Cell penetrant inhibitors of the KDM4 and KDM5 families of histone lysine demethylases. 1. 3-Amino-4-pyridine carboxylate derivatives. J. Med. Chem. 2016, 59, 1357-69; (k) Westaway, S. M.; Preston, A. G.; Barker, M. D et al. Cell penetrant inhibitors of the KDM4 and KDM5 families of histone lysine demethylases. 2. Pyrido[3,4-d]pyrimidin-4 (3H)-one derivatives. J. Med. Chem. 2016, 59, 1370-87; (l) Fang, Z.; Wang, T. Q.; Li, H.; Zhang, G.; Wu, X. A.; Yang, L.; Peng, Y. L.; Zou, J.; Li, L. L.; Xiang, R.; Yang, S. Y. Discovery of pyrazolo[1,5-a]pyrimidine-3-carbonitrile derivatives as a new class of histone lysine demethylase 4D (KDM4D) inhibitors. Bioorg. Med. Chem. Lett. 2017, 27, 3201-3204; (m) Chen, Y. K.; Bonaldi, T.; Cuomo, A et al. Design of KDM4 inhibitors with anti-proliferative effects in cancer models. ACS Med. Chem. Lett. 2017, 8, 869-874; (n) Metzger, E.; Stepputtis, S. S.; Strietz, J. et al. KDM4 inhibition targets breast cancer stem-like cells. Cancer Res. 2017, 77, 5900-5912.

9) Duan, L.; Rai, G.; Roggero, C.; Zhang, Q. J.; Wei, Q.; Ma, S. H.; Zhou, Y.; Santoyo, J.; Martinez, E. D.; Xiao, G.; Raj, G. V.; Jadhav, A.; Simeonov, A.; Maloney, D. J.; Rizo, J.; Hsieh, J. T.; Liu, Z. P. KDM4/JMJD2 Histone Demethylase Inhibitors Block Prostate Tumor Growth by Suppressing the Expression of AR and BMYB-Regulated Genes. Chemistry & Biology 2015, 22, 1185-1196.

10) Duan et al. el., Histone Lysine Demethylase KDM4B Regulates the Alternative Splicing of the Androgen Receptor in Response to Androgen Deprivation, Nucleic Acids Res., 2019, 47:11623-11636.

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

What is claimed is:

1. A histone demethylase inhibitor, or a pharmaceutically acceptable salt thereof, having a structure given by the formula:

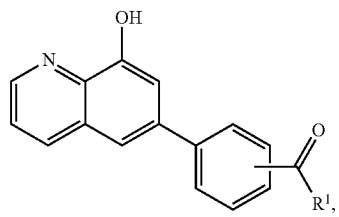

where $R^1$ is a group having a structure selected from the formulas:

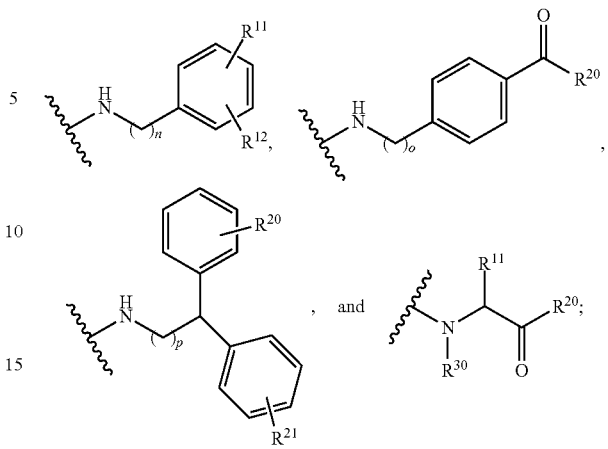

where n is from 0 to 10;
where o is from 0 to 10;
where p is from 0 to 10;
where each of $R^{11}$ and $R^{12}$, when present, is independently selected from hydrogen, halogen, hydroxy, thiol, cyano, amino, nitro, C1-C10 alkylamide, carbonyl, carboxylic acid, C1-C20 alkyl, C2-C20 alkenyl, C2-C20 alkynyl, C3-C20 cycloalkyl, C3-C20 heterocycloalkyl, aryl, heteroaryl, arylalkyl, and alkylaryl, and where each occurrence of C1-C10 alkylamide, C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl is optionally substituted with halogen, hydroxy, alkoxy, thiol, thioether, cyano, amino, carboxylic acid, ester, amide, carbamate, urea, guanidine, aryl substituted organic hydrazone, lactam substituted aryl group, nitro, —O—($C_1$-$C_6$ alkyl), —$NR^{40}R^{41}$ $C_1$-$C_6$ alkylhydroxyl, $C_1$-$C_6$ haloalkyl, $C_1$-$C_6$ cycloalkyl, $C_1$-$C_6$ alkylamino, —$OR^{40}$, —$COR^{40}$, —$CO_2R^{40}$, aryl, and —$CONR^{40}R^{41}$;
where each of $R^{20}$ and $R^{21}$, when present, is selected from hydrogen, C1-C20 alkyl, C2-C20 alkenyl, C2-C20 alkynyl, C3-C20 cycloalkyl, C3-C20 heterocycloalkyl, aryl, heteroaryl, $C_1$-C20 alkylheteroaryl, alkylaryl, —P(=O)(OH)$R^{40}R^{41}$, —$SR^{40}$, —S(=O)$2R^{40}R^{41}$, and —$NR^{40}R^{41}$ and where each occurrence of C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl is optionally substituted with halogen, hydroxy, thiol, cyano, amino, carboxylic acid, ester, amide, carbamate, urea, guanidine, nitro, —O—($C_1$-$C_6$ alkyl), —$NR^{40}R^{41}$, $C_1$-$C_6$ alkylhydroxyl, $C_1$-$C_6$ haloalkyl, $C_1$-$C_6$ alkylamino, C1-C6 cycloalkyl, C3-C20 heterocycloalkyl, —$COR^{40}$, —$CO_2R^{40}$, aryl, or —$CONR^{40}R^{41}$;
where $R^{30}$, when present, is selected from hydrogen, C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl where each occurrence of C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl is optionally substituted with halogen, hydroxy, thiol, cyano, amino, nitro, —O—($C_1$-$C_6$ alkyl), carboxylic acid, ester, amide, carbamate, urea, guanidine; and
where each occurrence of $R^{40}$ and $R^{41}$ is independently selected from hydrogen, C1-C20 alkyl, C2-C20 alkenyl, C2-C20 alkynyl, C3-C20 cycloalkyl, C3-C20 heterocycloalkyl, aryl, heteroaryl, and arylalkyl, alkylaryl where each occurrence of C1-C20 alkyl, C2-C20 alkenyl, C2-C20 alkynyl, C3-C20 cycloalkyl, C3-C20 heterocycloalkyl, aryl, heteroaryl, arylalkyl, or alkylaryl is optionally substituted with halogen, hydroxy, thiol, cyano, amino, nitro, —O—($C_1$-$C_6$ alkyl), halogen-substituted-O—($C_1$-$C_6$ alkyl), —O—($C_1$-$C_6$ aryl), halogen-substituted-O—($C_1$-$C_6$ aryl), carboxylic acid, ester, amide, carbamate, urea, guanidine, $C_1$-$C_4$ linear or branched alkyl or haloalkyl, or $C_3$-$C_6$ cycloalkyl optionally substituted with a $C_1$-$C_3$ alkyl group or a C6 aryl group;

and provided that the compound does not have a structure given by the formula:

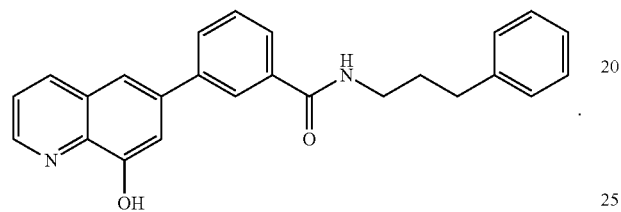

2. The histone demethylase inhibitor or pharmaceutically acceptable salt thereof of claim 1, wherein $R^1$ is

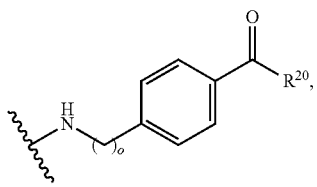

o is 1, $R^{20}$ is $NR^{40}R^{41}$, $R^{40}$ is hydrogen, and $R^{41}$ is C1-C20 alkyl substituted with $C_3$-$C_6$ cycloalkyl optionally substituted with a $C_1$-$C_3$ alkyl group, a C6 aryl group, or a $C_1$-$C_4$ linear or branched alkyl or haloalkyl group.

3. The histone demethylase inhibitor or pharmaceutically acceptable salt thereof of claim 1, wherein $R^1$ is

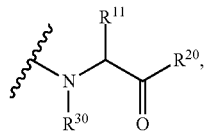

$R^{30}$ is hydrogen, $R^{11}$ is alkyl, hydrogen, alkylthioether, alkyl amide, hydroxy substituted alkyl aryl, or hydroxy substituted alkyl, $R^{20}$ is $NR^{40}R^{41}$, $R^{40}$ is hydrogen, and $R^{41}$ is alkylaryl.

4. The histone demethylase inhibitor or pharmaceutically acceptable salt thereof of claim 1, wherein $R^1$ is

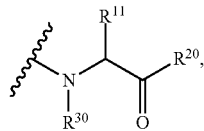

$R^{30}$ is H, $R^{11}$ is alkyl heteroaryl, $R^{20}$ is $NR^{40}R^{41}$, $R^{40}$ is hydrogen, and $R^{41}$ is substituted or unsubstituted alkylaryl.

5. The histone demethylase inhibitor or pharmaceutically acceptable salt thereof of claim 1, wherein $R^1$ is

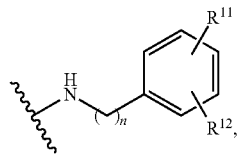

n is from 0 to 4, and $R^{11}$ and $R^{12}$ are hydrogen.

6. The histone demethylase inhibitor or pharmaceutically acceptable salt thereof of claim 1, wherein $R^1$ is

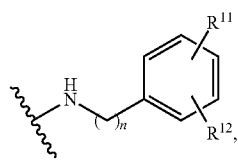

n is 1, $R^{11}$ is hydrogen or alkoxy, $R^{12}$ is cyano, alkoxy, substituted amine, $COR^{40}$, or $OR^{40}$, and $R^{40}$ is aryl, heteroaryl, or aryl substituted with a halogen.

7. The histone demethylase inhibitor or pharmaceutically acceptable salt thereof of claim 1, wherein $R^1$ is

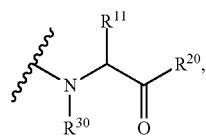

$R^{30}$ is hydrogen, $R^{11}$ is methyl, $R^{20}$ is $NR^{40}R^{41}$, $R^{40}$ is hydrogen, and $R^{41}$ is unsubstituted or substituted alkylaryl.

8. The histone demethylase inhibitor or pharmaceutically acceptable salt thereof of claim 1, wherein $R^1$ is

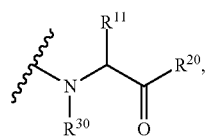

$R^{30}$ is hydrogen, $R^{20}$ is $NR^{40}R^{41}$, $R^{40}$ is hydrogen, $R^{41}$ is alkylaryl, and $R^{11}$ is alkylamide substituted with a cycloalkyl or aryl group.

9. The histone demethylase inhibitor or pharmaceutically acceptable salt thereof of claim 1, wherein $R^1$ is

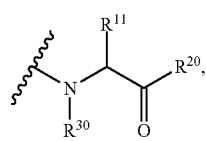

$R^{30}$ is hydrogen, $R^{11}$ is alkylheteroaryl, $R^{20}$ is $NR^{40}R^{41}$, $R^{40}$ is hydrogen, and $R^{41}$ is aryl or heteroaryl.

10. The histone demethylase inhibitor or pharmaceutically acceptable salt thereof of claim 1, wherein $R^1$ is

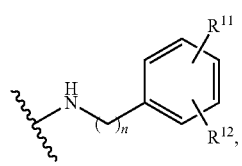

n is 0 or 1, $R^{11}$ is halogen, substituted or unsubstituted arylalkyl, ester, or $COR^{40}$, $R^{12}$ is hydrogen or halogen, and $R^{40}$ is aryl.

11. The histone demethylase inhibitor or pharmaceutically acceptable salt thereof of claim 1, wherein $R^1$ is

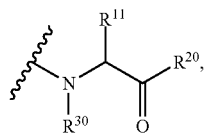

$R^{11}$ is alkyl, alkyl thioether, hydroxyl substituted alkyl aryl, hydroxyl substituted alkyl, or alkylheteroaryl, $R^{30}$ is hydrogen, $R^{20}$ is $NR^{40}R^{41}$, $R^{40}$ is hydrogen, and $R^{41}$ is alkylaryl optionally substituted with halogen or aryl.

12. The histone demethylase inhibitor or pharmaceutically acceptable salt thereof of claim 1, wherein $R^1$ is

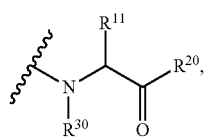

$R^{30}$ is hydrogen, $R^{11}$ is alkylaryl or alkylheteroaryl, $R^{20}$ is $NR^{40}R^{41}$, $R^{40}$ is hydrogen, and $R^{41}$ is alkyl aryl or aryl heterocycloalkyl.

13. The histone demethylase inhibitor or pharmaceutically acceptable salt thereof of claim 1, wherein $R^1$ is

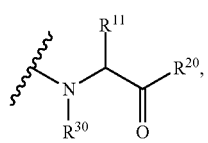

$R^{30}$ is hydrogen, $R^{11}$ is alkylaryl, $R^{20}$ is $NR^{40}R^{41}$, $R^{40}$ is hydrogen, and $R^{41}$ is alkyl substituted with a cycloalkyl group.

14. The histone demethylase inhibitor or pharmaceutically acceptable salt thereof of claim 1, wherein $R^1$ is

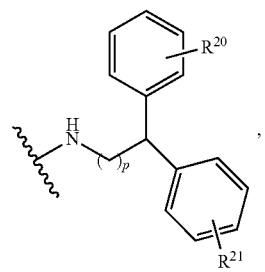

p is 2, $R^{20}$ is halogen, and $R^{21}$ is alkyl substituted with halogen.

15. A pharmaceutical composition comprising at least one compound or pharmaceutically acceptable salt thereof of claim 1 and at least one pharmaceutically acceptable excipient.

16. The pharmaceutical composition of claim 15, wherein the at least one pharmaceutically acceptable excipient comprises an α-cyclodextrin, a β-cyclodextrin, a γ-cyclodextrin, liposomes, a surfactant, glycerol, a polyethylene glycol, a preservative, water, ethanol, a vegetable oil, saline solution, glucose solution, a phosphate buffer, mannitol, normal serum albumin, sodium chloride solution, Ringer's dextrose, lactated Ringer's, a fixed oil, a chelating agent, or a combination thereof.

17. A method for treating prostate cancer comprising administering to a patient in need of cancer treatment an effective amount of the pharmaceutical composition of claim 15.

18. The method of claim 17, wherein the effective amount comprises from about 10 mg of the compound to about 20 mg of the compound per kg of patient body weight.

19. The histone demethylase inhibitor or pharmaceutically acceptable salt thereof of claim 1, wherein the histone demethylase inhibitor or pharmaceutically acceptable salt thereof has the formula:

(SS30)

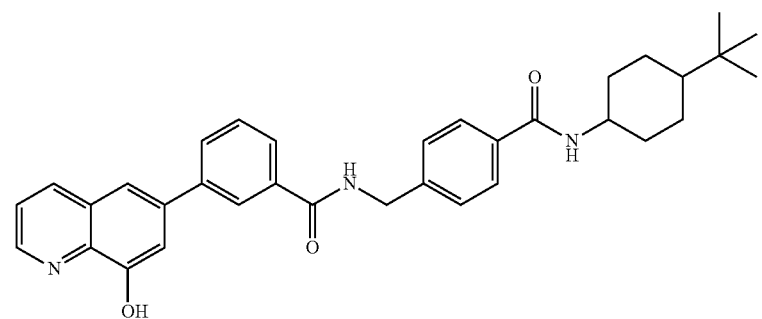

-continued
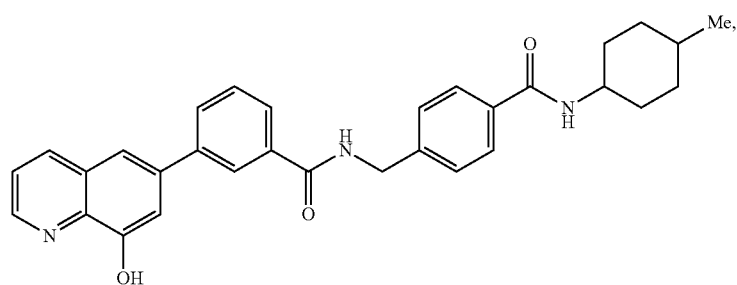
(SS31)
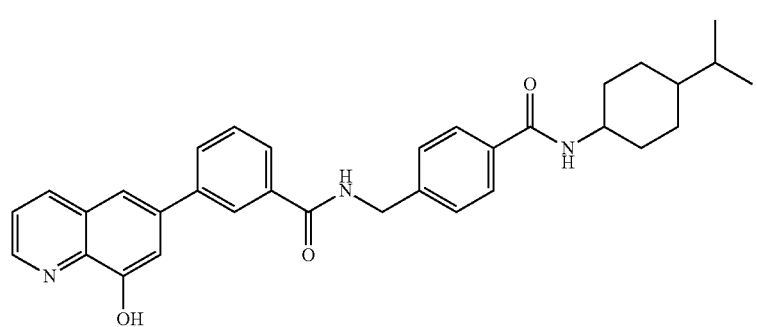
(SS32)
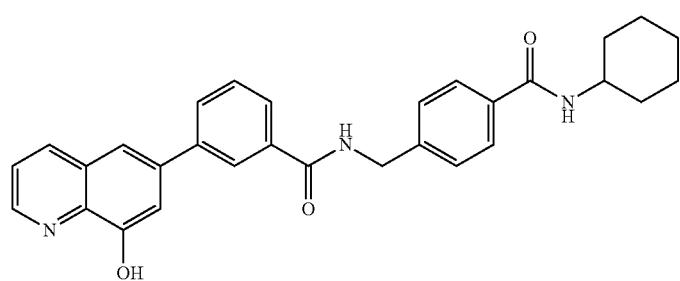
(SS33)
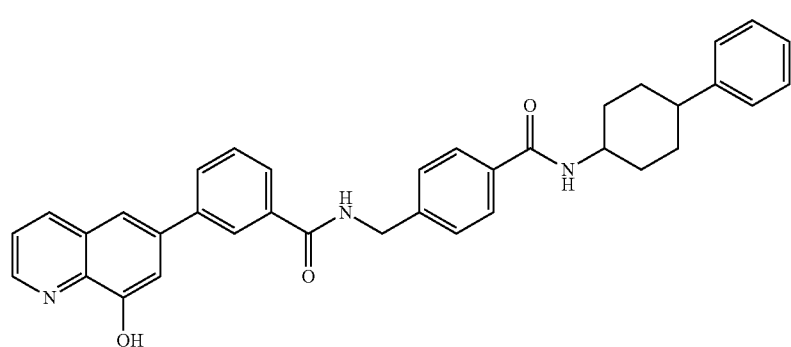
(SS34)
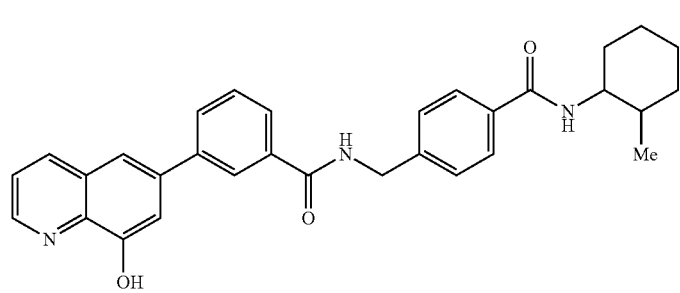
(SS35)

-continued
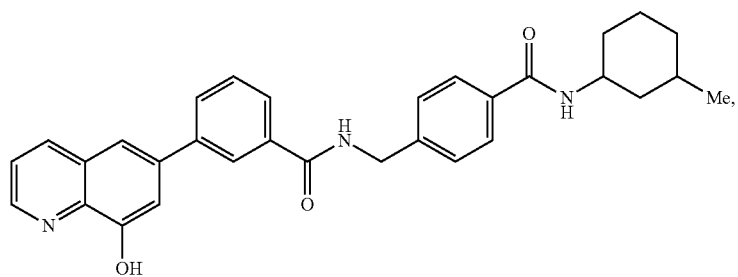
(SS36)
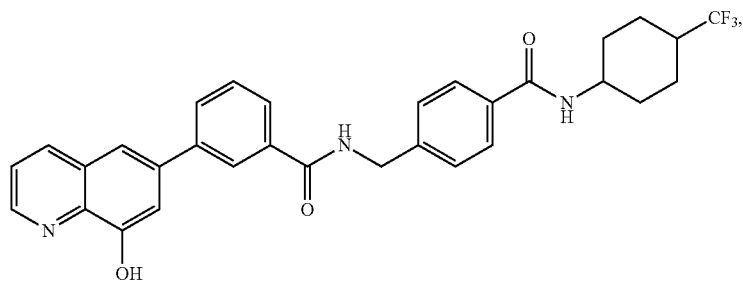
(SS27, oSS12, SS02208, SS79, SS79N, SS81, 17l)
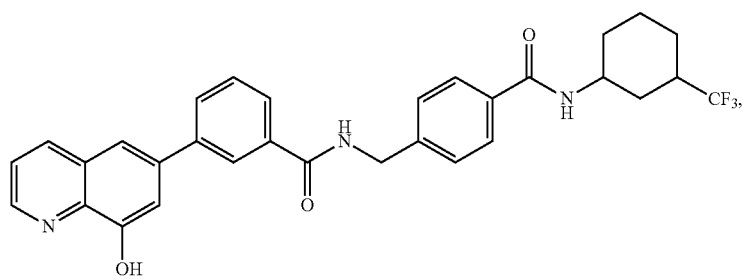
(SS46)
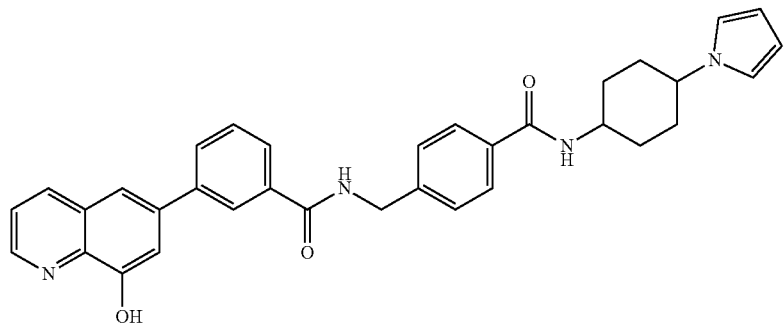
(SS48)
,
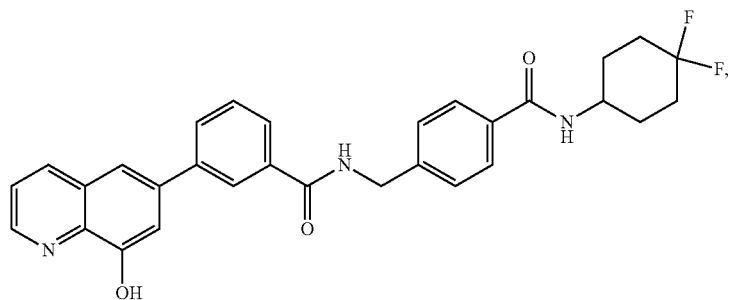
(SS49)

-continued
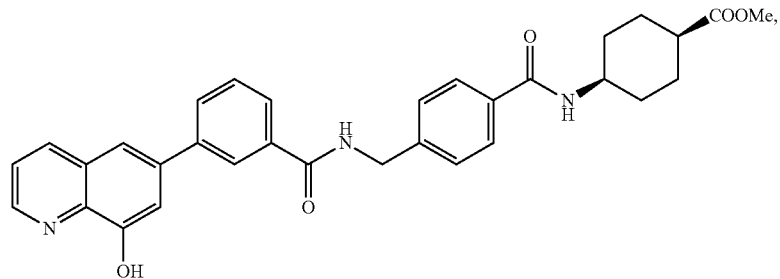 (SS51)
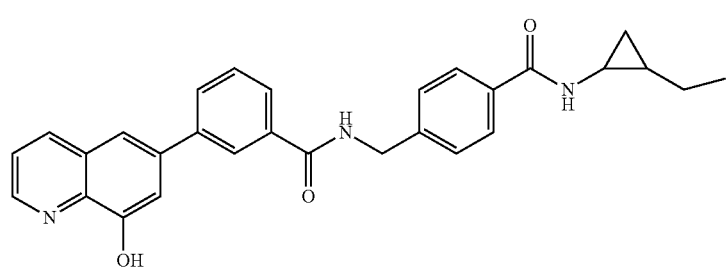 (SS54)
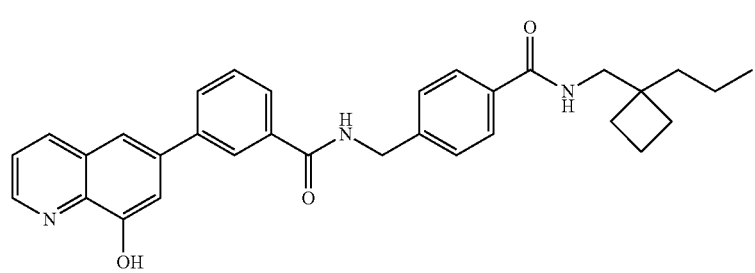 (SS55)
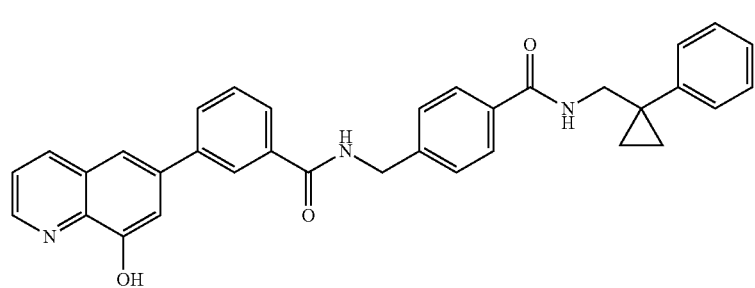 (SS56)
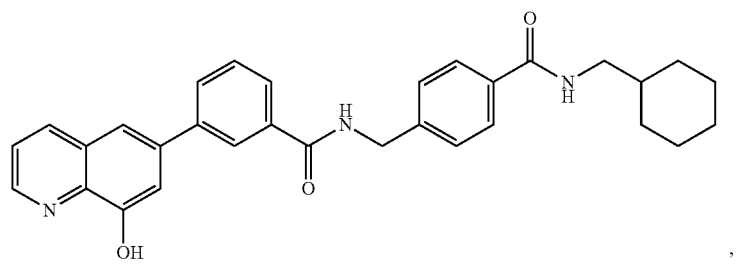 (SS37 or SS2097)

-continued
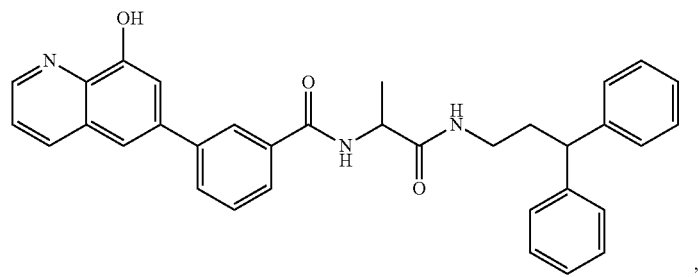
(3028-5)
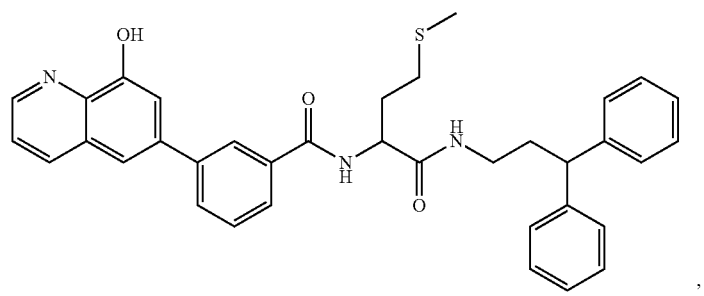
(3028-6)
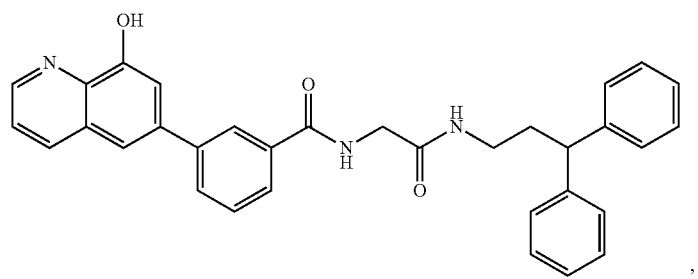
(3029-3)
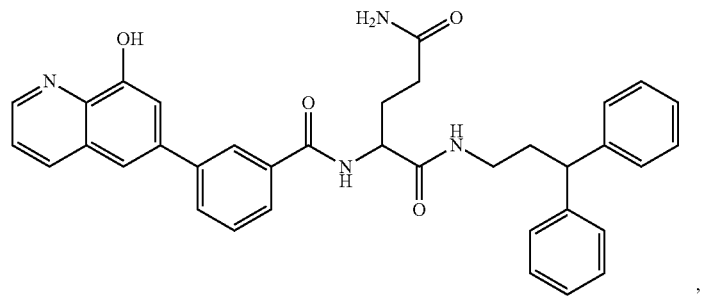
(3029-5)
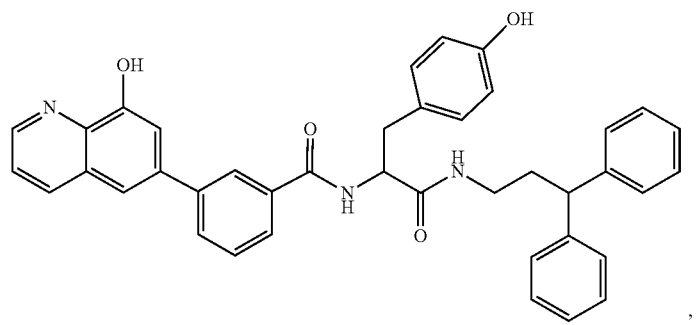
(3029-6)

(3030-3)
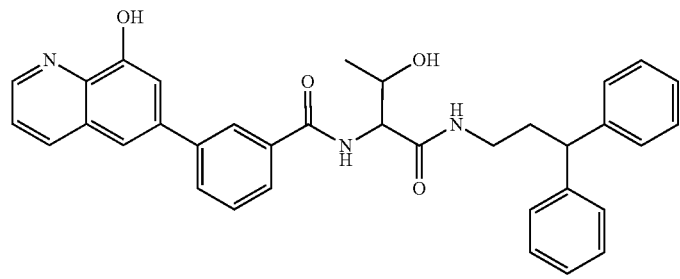
(3025-1)
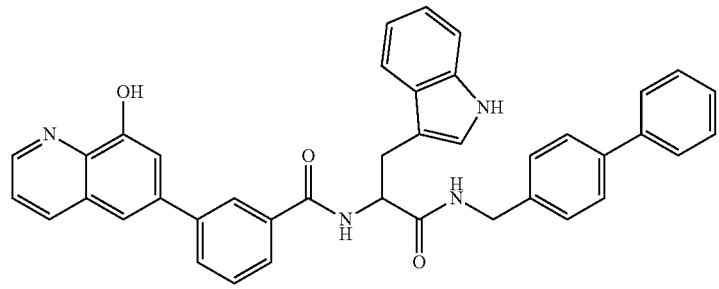
(3025-2)
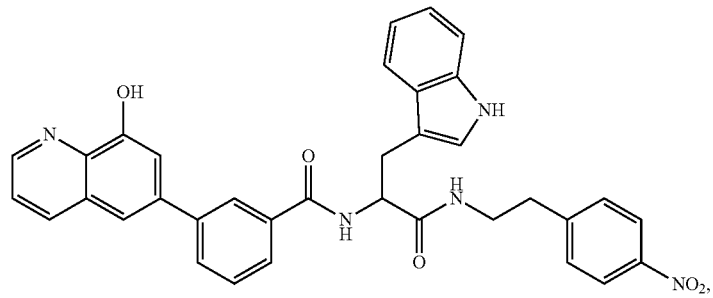
(3025-3)
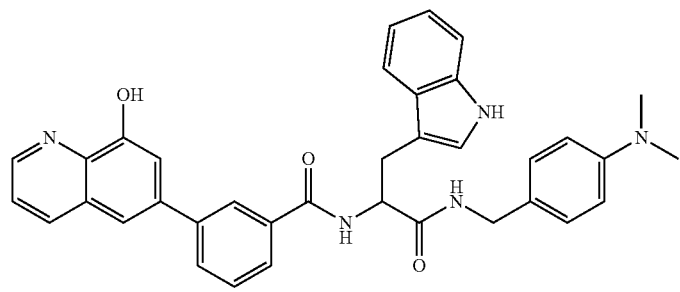
(3025-6)
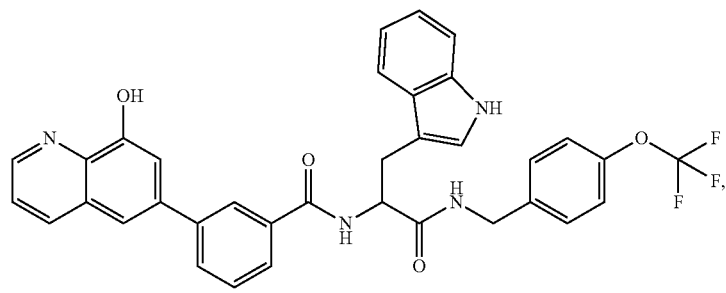

-continued
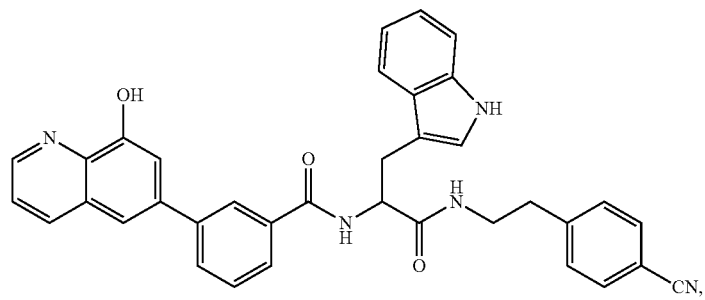
(3026-3)
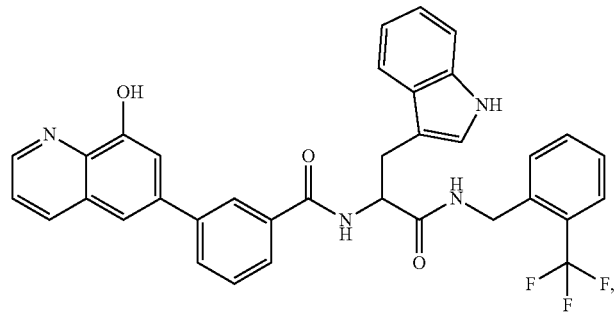
(3026-6)
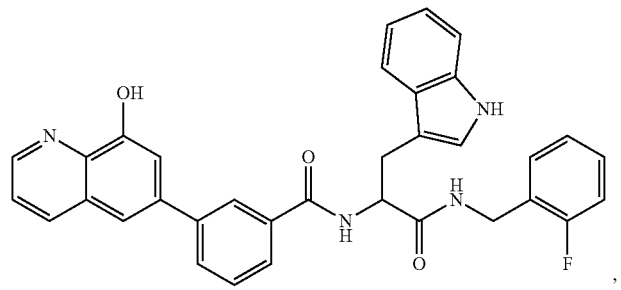
(3027-1)
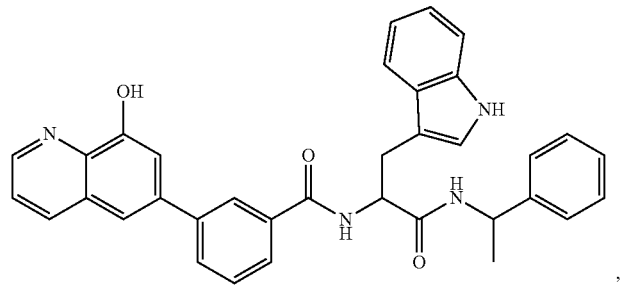
(3027-2)
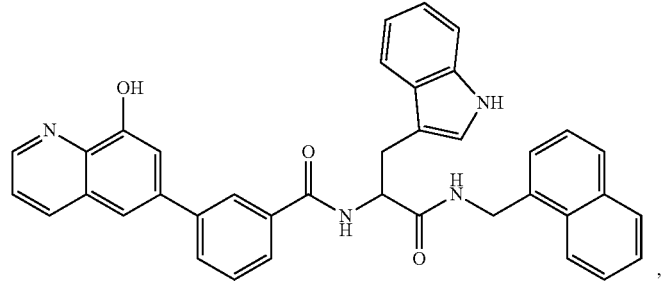
(3027-3)

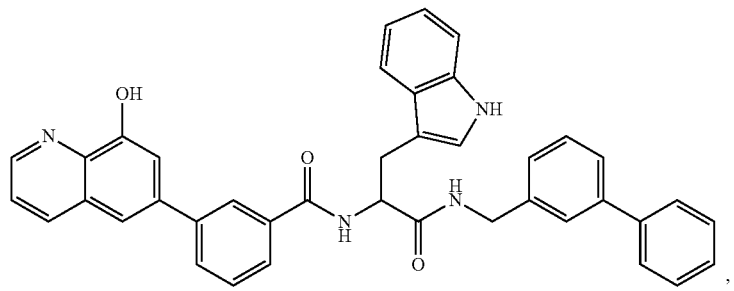
(3027-4)
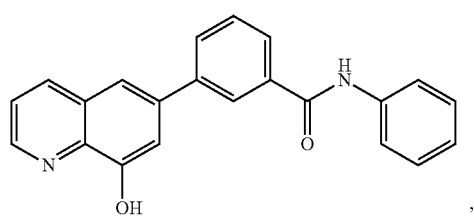
(SS04190 or SS-61)
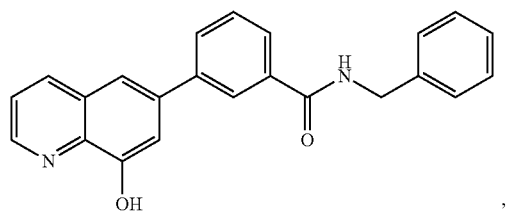
(SS04191 or SS-62)
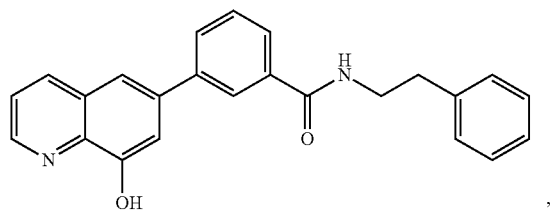
(SS04194 or SS-64)
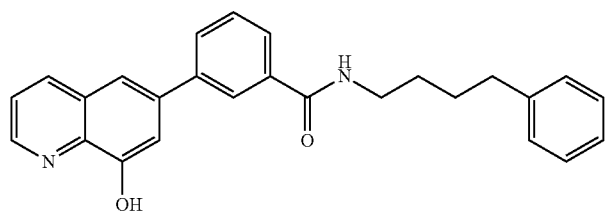
(SS04193 or SS-63)
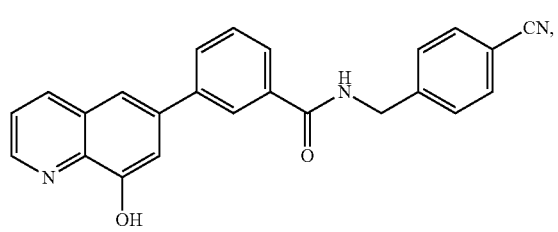
(SS02106)

-continued
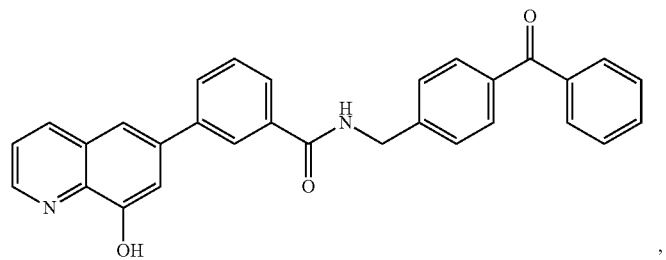
(SS74 or SS02132)
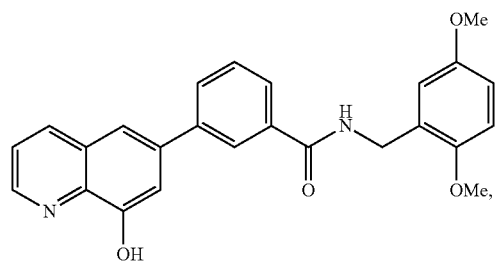
(SS02075)
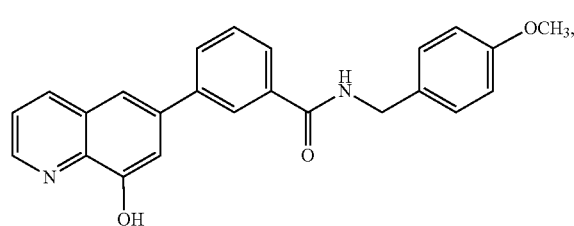
(SS02083)
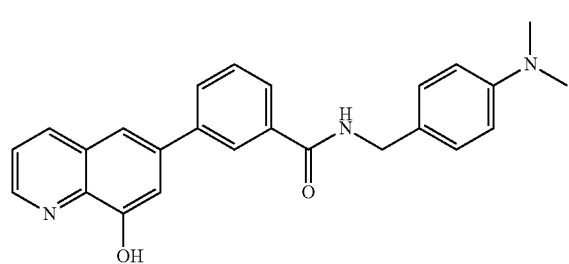
(SS02095)
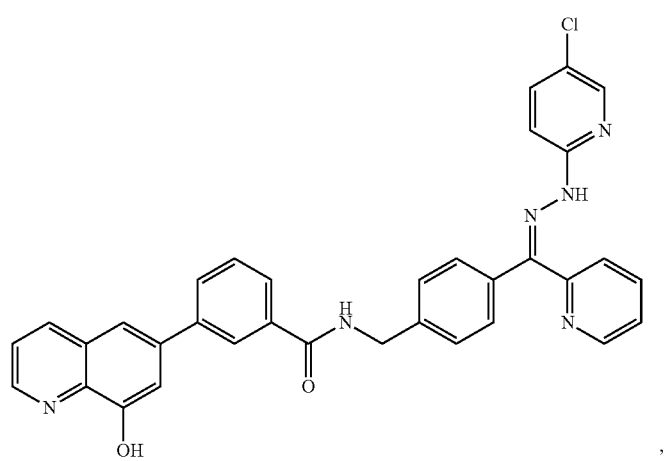
(SS1)

-continued
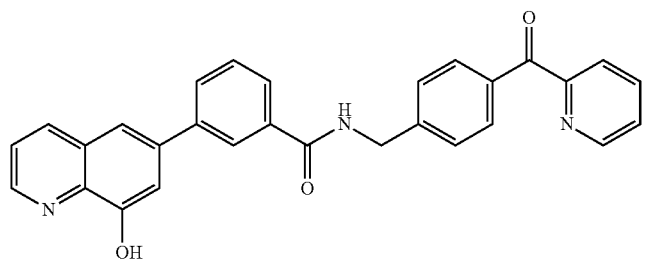
(SS2)
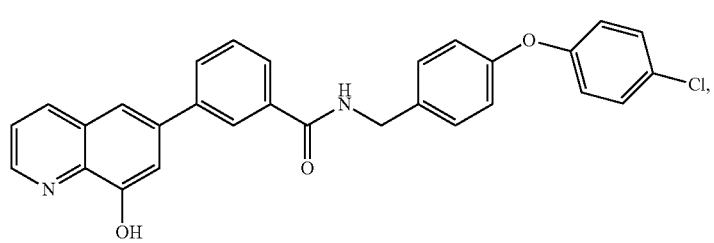
(SS12 or SS03154)
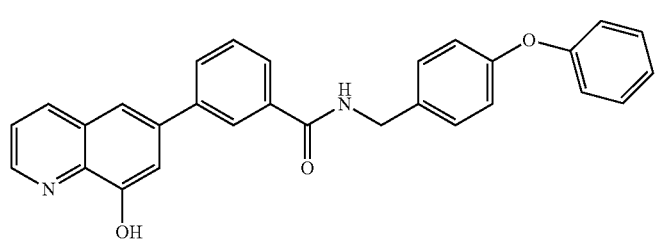
(SS13 or SS03152)
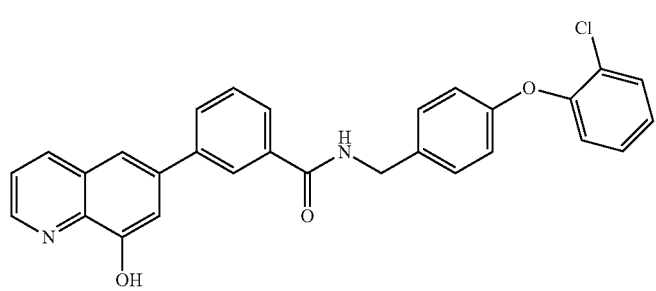
(SS14 or SS03156)
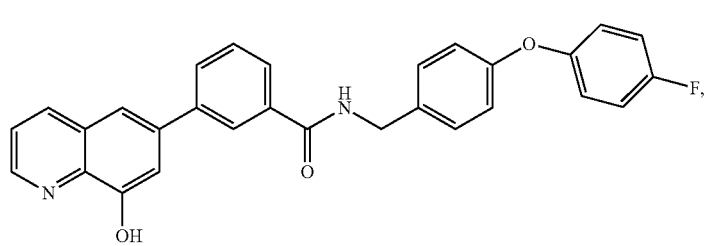
(SS15 or SS03158)
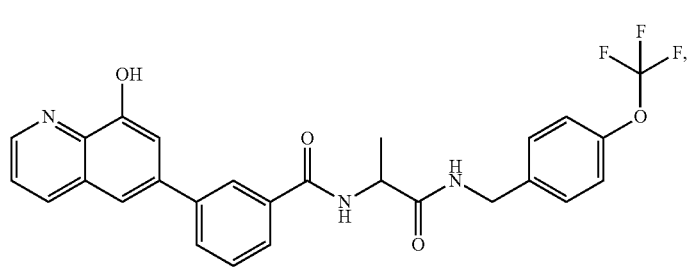
(3009-3)

-continued
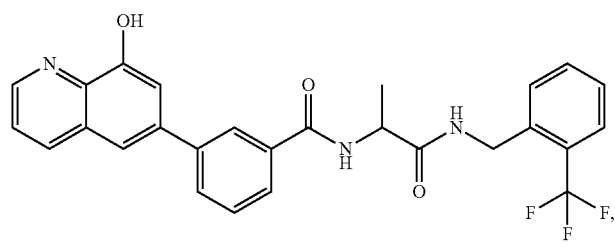
(3009-4)
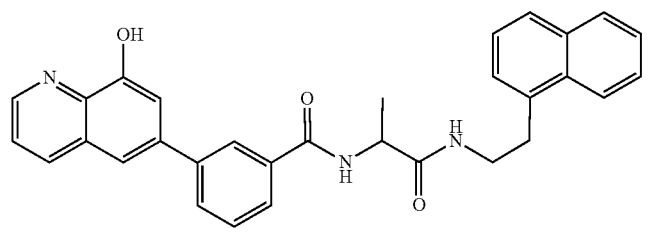
(3009-6)
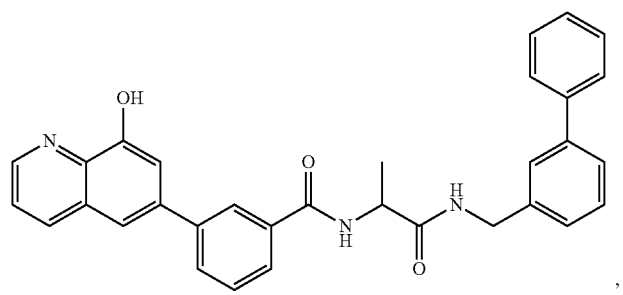
(3010-1)
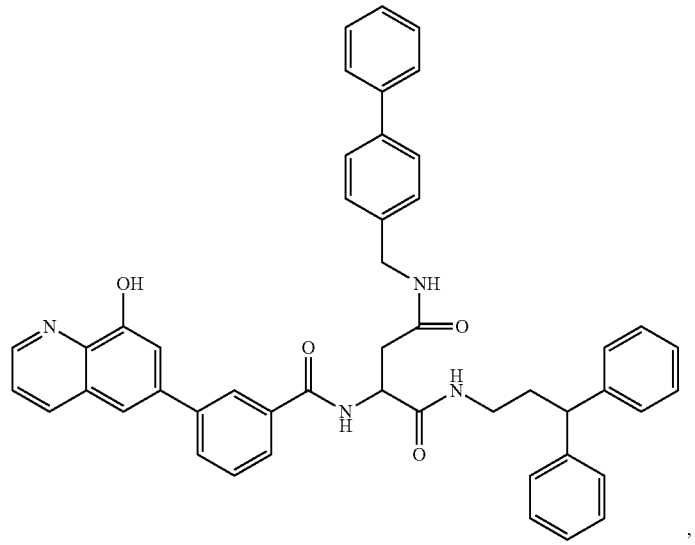
(3033-3)

-continued
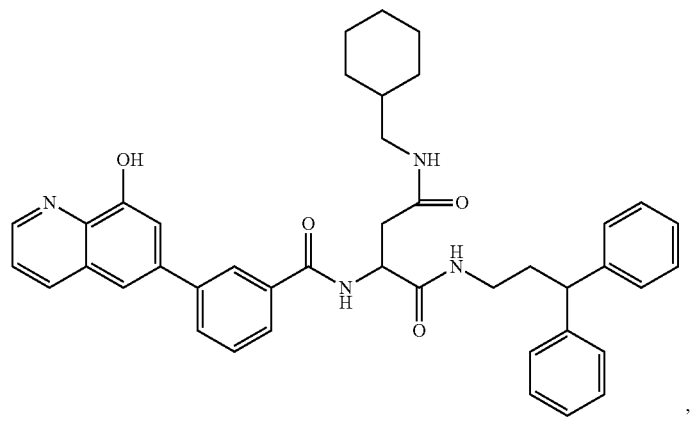
(3033-5)
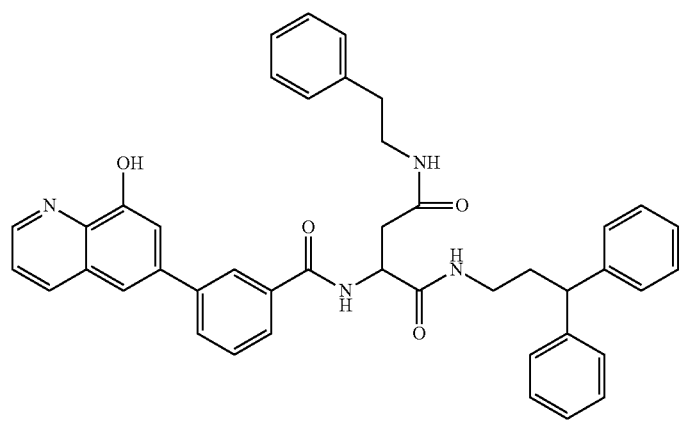
(3033-6)
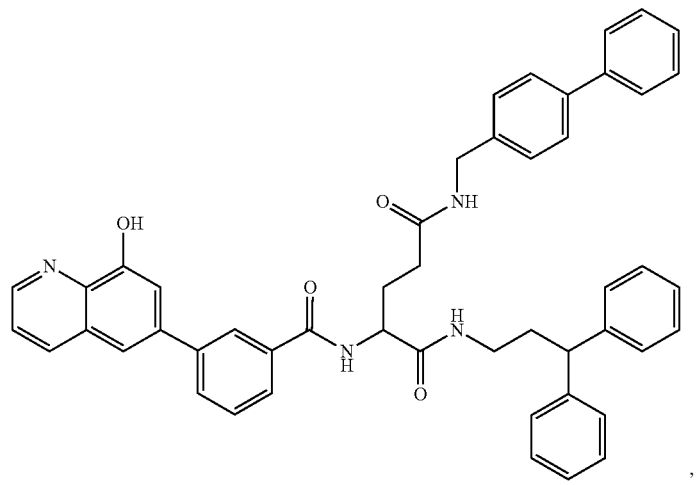
(3034-3)
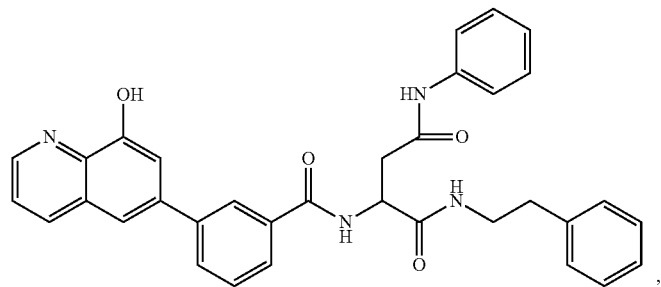
(3013-6)

-continued
(3031-3)
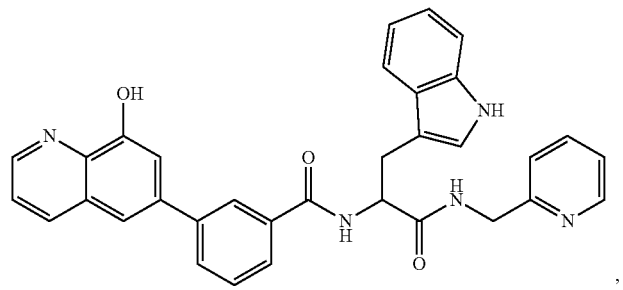
(3031-4)
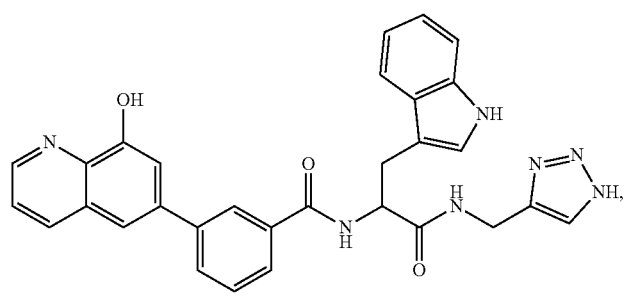
(3031-5)
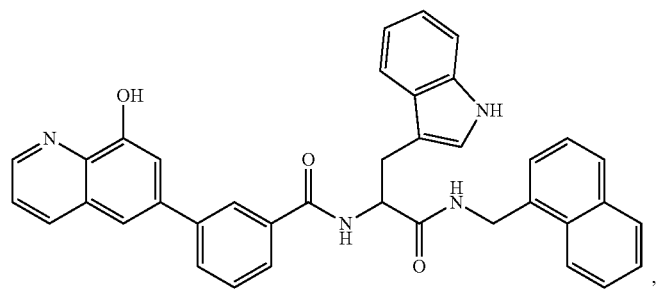
(3031-6)
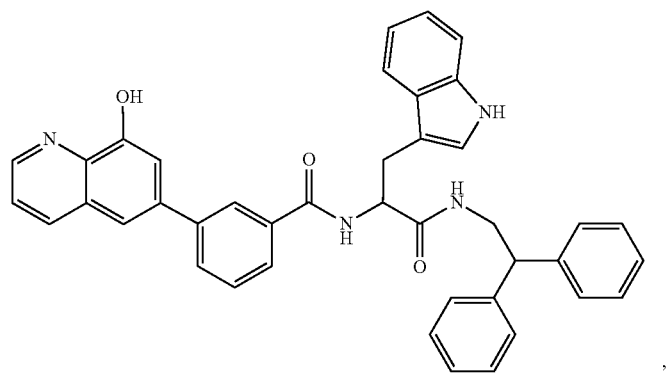
(oSS2)
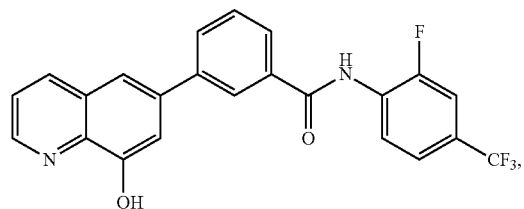

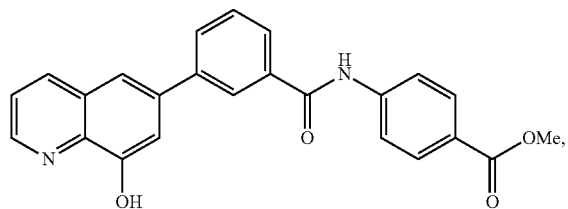
(oSS5 or SS02183)
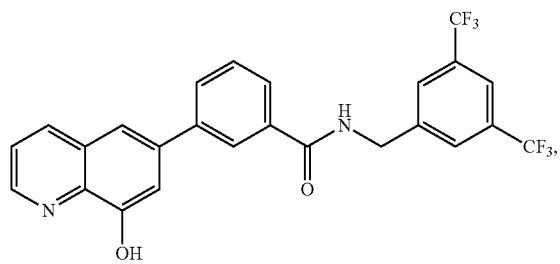
(oSS8 or SS02177)
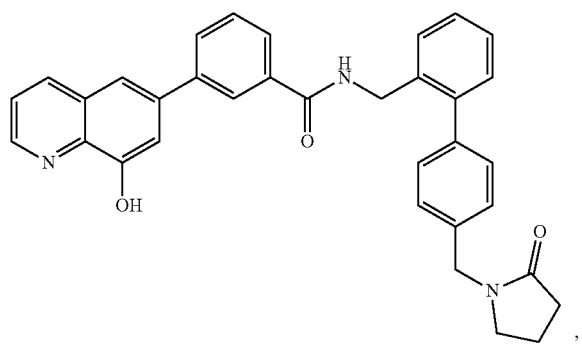
(oSS18 or SS03020)
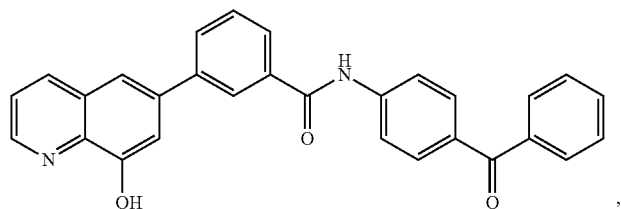
(oSS28)
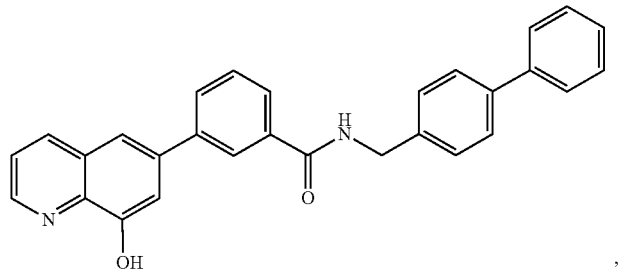
(SS72 or SS0286)
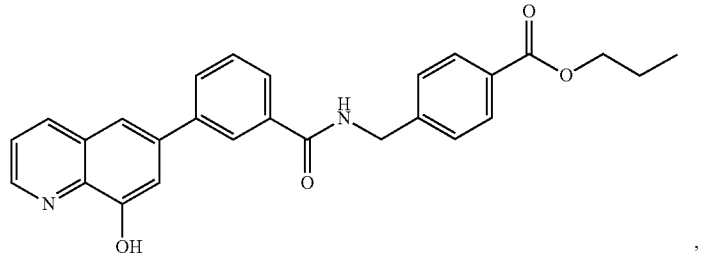
(SS67 or SS04111)

-continued
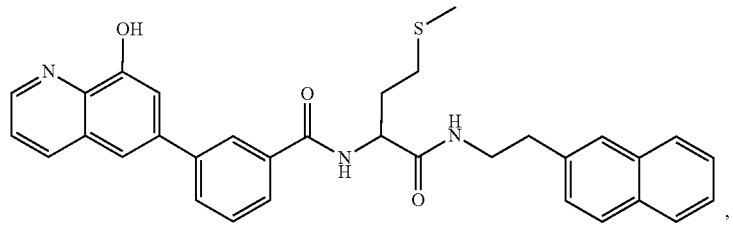
(3023-3)
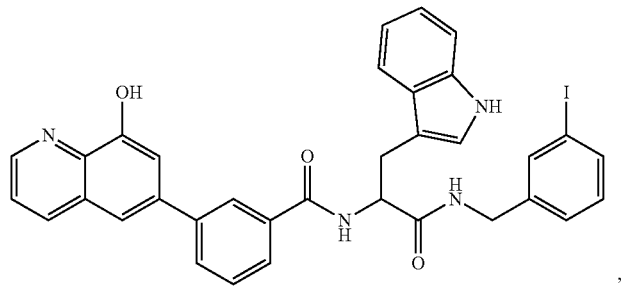
(3001-1)
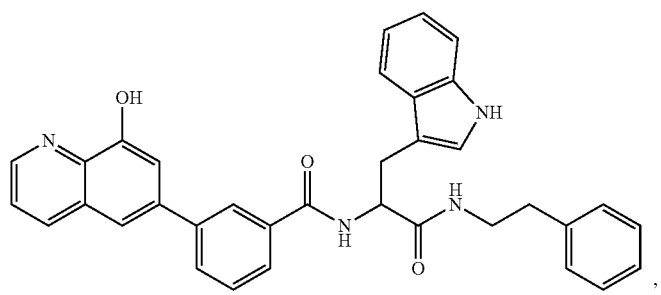
(3001-2)
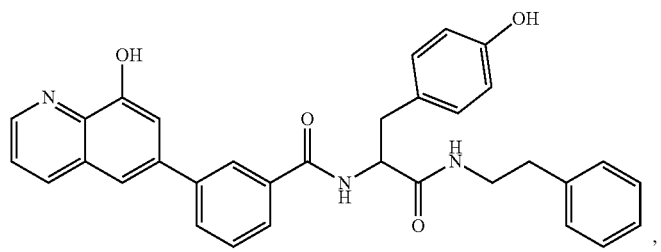
(3001-3)
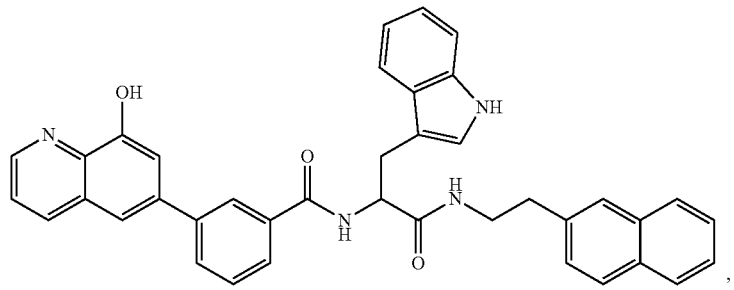
(3001-4)
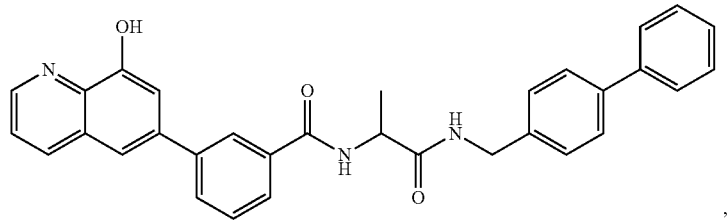
(3003-1)

(3003-2)
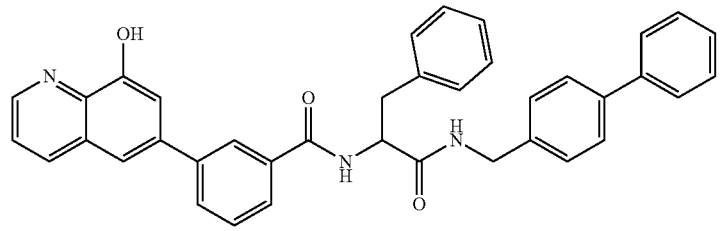
(3003-4)
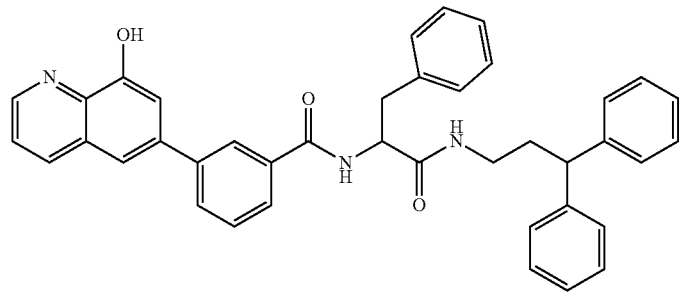
(3003-5)
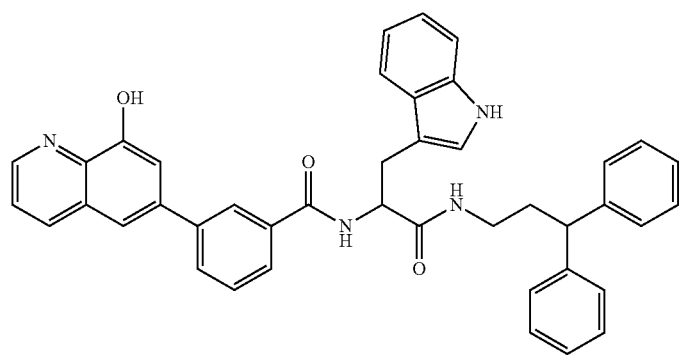
(3029-4)
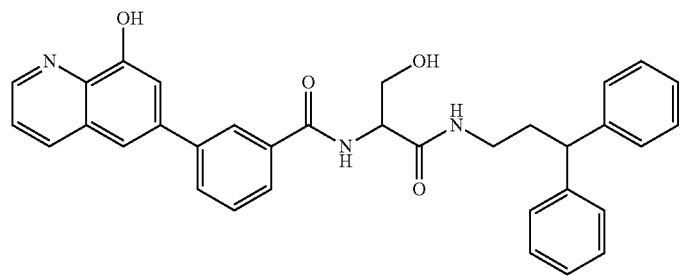
(3024-1)
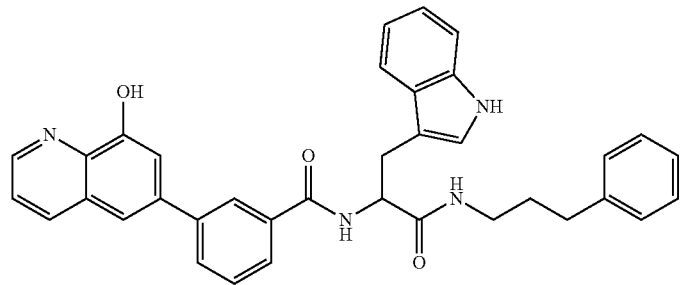

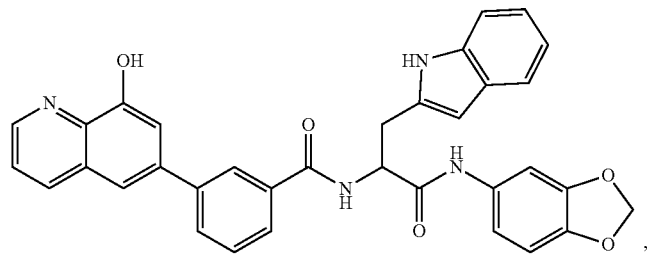
(3008-1 or D37)
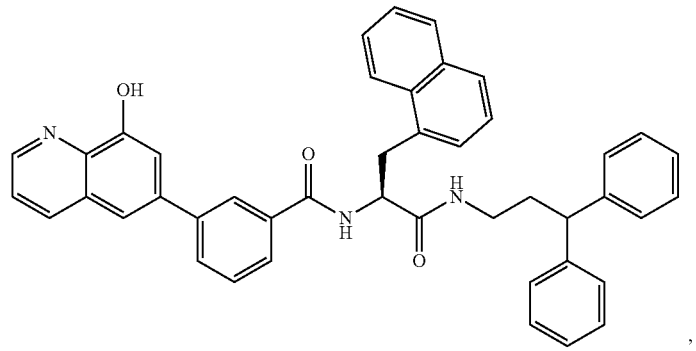
(3030-6)
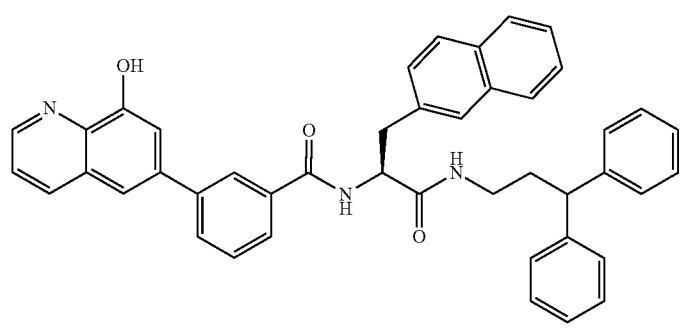
(3031-1)
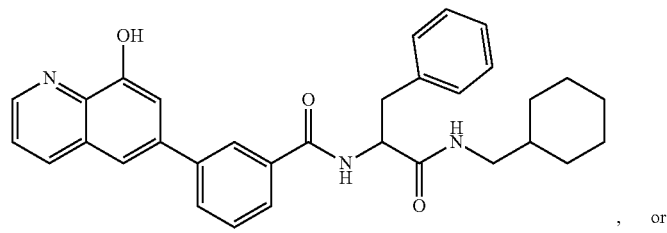
, or
(3004-4)
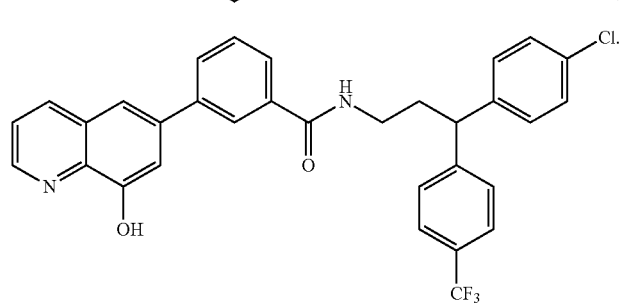
(SS18)
* * * * *